US011820828B2

(12) United States Patent
Demarest et al.

(10) Patent No.: US 11,820,828 B2
(45) Date of Patent: Nov. 21, 2023

(54) METHODS FOR PRODUCING FABS AND IGG BISPECIFIC ANTIBODIES

(71) Applicants: Eli Lilly and Company, Indianapolis, IN (US); The University of North Carolina at Chapel Hill, Chapel Hill, NC (US)

(72) Inventors: Stephen John Demarest, San Diego, CA (US); Karen Jean Froning, Escondido, CA (US); Brian Arthur Kuhlman, Chapel Hill, NC (US); Andrew Philip Leaver-Fay, Carrboro, NC (US)

(73) Assignees: Eli Lilly and Company, Indianapolis, IN (US); The University of North Carolina at Chapel Hill, Chapel Hill, NC (US)

( * ) Notice: Subject to any disclaimer, the term of this patent is extended or adjusted under 35 U.S.C. 154(b) by 320 days.

(21) Appl. No.: 16/465,689

(22) PCT Filed: Dec. 14, 2017

(86) PCT No.: PCT/US2017/066296
§ 371 (c)(1),
(2) Date: May 31, 2019

(87) PCT Pub. No.: WO2018/118616
PCT Pub. Date: Jun. 28, 2018

(65) Prior Publication Data
US 2019/0292268 A1 Sep. 26, 2019

Related U.S. Application Data

(60) Provisional application No. 62/437,740, filed on Dec. 22, 2016.

(51) Int. Cl.
*C07K 16/28* (2006.01)
*C07K 16/32* (2006.01)
*C07K 16/46* (2006.01)

(52) U.S. Cl.
CPC ...... *C07K 16/2878* (2013.01); *C07K 16/2863* (2013.01); *C07K 16/32* (2013.01); *C07K 16/468* (2013.01); *C07K 2317/21* (2013.01); *C07K 2317/31* (2013.01); *C07K 2317/41* (2013.01); *C07K 2317/522* (2013.01); *C07K 2317/526* (2013.01); *C07K 2317/64* (2013.01); *C07K 2317/92* (2013.01); *C07K 2317/94* (2013.01); *C07K 2319/00* (2013.01)

(58) Field of Classification Search
CPC ............ C07K 16/468; C07K 2317/522; C07K 2317/51; C07K 2317/55; C07K 2317/56
USPC .......................................... 424/133.1, 136.1
See application file for complete search history.

(56) References Cited

U.S. PATENT DOCUMENTS

2014/0154254 A1 6/2014 Kannan et al.
2017/0204199 A1* 7/2017 Sanches ................. C07K 16/32

FOREIGN PATENT DOCUMENTS

WO 2010/115553 A1 10/2010
WO 2014/150973 A1 9/2014
WO 2016/118742 A1 7/2016

OTHER PUBLICATIONS

Toughiri et al. (MAbs. Oct. 2016; 8(7): 1276-1285).*
EP 17826058 (Communication from the Examining Division; pp. 1-2; Mar. 10, 2023).*
Leaver-Fay, et al. Structure. 24: 641-651 (2016).
Lewis, et al., Nat. Biotechnol., 32; 191-198 (2014).
Carter, et al., J. Immunol. Methods; 248; 7-15 (2001).
Gunasekaran, et al., J. Biol. Chem; 285; 19637-19646 (2010).
Zhu et al., Protein Sci.; 6: 781-788 (1997).
Igawa et al., Protein Eng. Des. Sel.; 23; 667-677 (2010).
"Written Opinion of the International Search Authority," Date of completion of this opinion as per Form PCT/ISA/210: Date of the actual completion of the International search Jan. 30, 2018, international search report dated Feb. 6, 2018.

* cited by examiner

*Primary Examiner* — Lynn A Bristol
(74) *Attorney, Agent, or Firm* — Nielsen IP Law LLC

(57) ABSTRACT

Methods for producing Fabs and IgG bi-specific antibodies comprising expressing nucleic acids encoding designed residues in the CH1/CL interface are provided. Also provided are Fabs and IgG bi-specific antibodies produced according to the provided methods as well as nucleic acids, vectors and host cells encoding the same.

34 Claims, 1 Drawing Sheet
Specification includes a Sequence Listing.

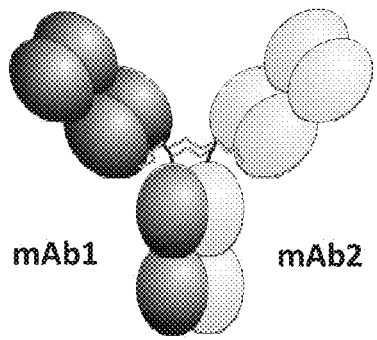

1A.

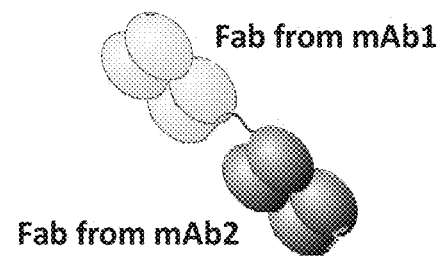

1B.

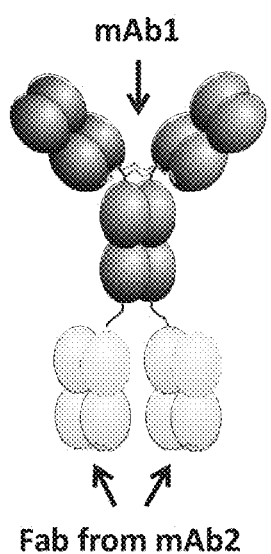 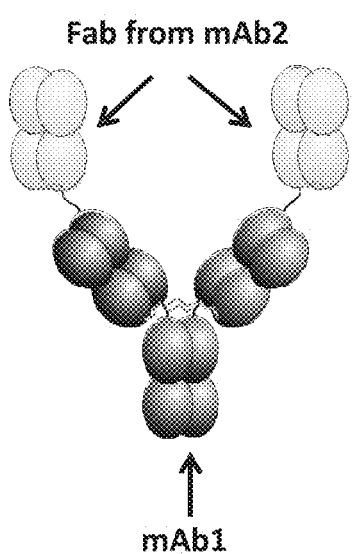 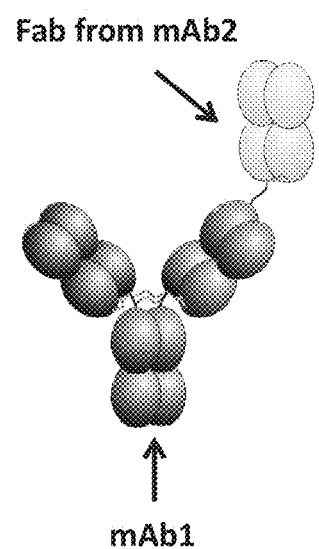

1C.

1A. Full IgG bispecific antibody comprising a HC and LC from a first mAb (denoted mAb1) targeting one antigen and a HC and LC from a second mAb (denoted mAb2) recognizing a different antigen.

1B. Fab-Fab construct comprising a Fab from first mAb (mAb1) and a Fab from second mAb (mAb2).

1C. Alternate bispecific constructs comprising a first mAb (mAb1) and Fab fragments from a second mAb (mAb2).

METHODS FOR PRODUCING FABS AND IGG BISPECIFIC ANTIBODIES

CROSS-REFERENCE TO RELATED PATENT APPLICATIONS

This application is a U.S. national stage entry under 35 U.S.C. 371 of PCT/US2017/066296, filed on Dec. 14, 2017, which claims the benefit of priority to U.S. provisional patent application 62/437,740, filed on Dec. 22, 2016.

REFERENCE TO A SEQUENCE LISTING SUBMITTED VIA EFS-WEB

The Sequence Listing associated with this application was filed in electronic format via EFS-Web at the time the application was filed on May 13, 2019 and forms part of the Specification. The name of the text file containing the Sequence Listing is "X20936SequenceListing." The size of the text file is 210,000 bytes, and the text file was created on May 13, 2019.

BACKGROUND

Bispecific antibodies integrate the binding properties of two distinct antigen binding proteins into a single molecule. Bispecific antibodies represent an alternative to the co-formulation and/or co-administration of separate antibody agents or fragments, when the therapeutic targeting of multiple antigens or epitopes is desired. In addition, bispecific antibodies may elicit synergistic activities beyond that of an antibody combination. For example, bispecific antibodies could be used to bridge different cell types through binding of distinct cell surface receptors, thus facilitating, for example, the targeting of immune cells to tumor cells. Alternately, bispecific antibodies could cross-link and/or cluster separate cell surface signaling receptors to elicit novel mechanisms of action.

The archetypical IgG antibody is a hetero-tetramer comprised of two identical heavy chains (HC) and two identical light chains (LC). Each HC associates with a separate LC to form two identical antigen binding fragments (Fabs) via assembly interfaces between the HC and LC variable domains (the $V_H/V_L$ interface) and the HC constant $C_H1$ and LC constant domains (the $C_H1/C_L$ interface.) Once formed, each Fab directs the binding of the IgG antibody to the same antigenic determinant. As a consequence of their modular nature, numerous formats have been proposed for generating IgG-derived bispecific antibodies. Examples include, diabodies, IgG-single chain variable fragments (IgG-scFv), dual variable domain-IgG (DVD-IgG), Fab-Fab, and IgG-Fab. However, many of these formats alter the native IgG antibody geometry and its resulting stability and solubility, and/or require extensive engineering to stabilize component variable domains outside of the native Fab context.

Recently, methods have been described for generating bispecific antibodies retaining the full IgG antibody architecture by co-expressing nucleic acids encoding two distinct HC-LC pairs containing designed mutations in the $C_H1/C_L$ and/or $V_H/V_L$ interfaces which, when expressed, provide improved assembly of a fully IgG antibody comprising two distinct Fabs. (See Lewis, et al. (2014), Nat. Biotechnol., 32; 191-198; and Published PCT Applications WO2014/150973 and WO2014/0154254) In addition, procedures for directing assembly of particular HC-HC pairs by introducing modifications into regions of the HC-HC interface to promote improved HC heterodimerization have also been disclosed in the art (See Leaver-Fay A., et al. (2016), Structure; 24; 641-651; Klein et al., mAbs; 4(6); 1-11 (2012); Carter et al., J. Immunol. Methods; 248; 7-15 (2001); Gunasekaran, et al., J. Biol. Chem.; 285; 19637-19646 (2010); Zhu et al., Protein Sci.; 6: 781-788 (1997); and Igawa et al., Protein Eng. Des. Sel.; 23; 667-677 (2010)). However, there yet remains a need for alternative methods for generating fully IgG BsAbs.

SUMMARY

In accordance with the present invention, further methods have been identified for achieving assembly of distinct Fabs by co-expressing nucleic acids encoding particular HC-LC pairs which contain designed residues in the $C_H1/C_L$ interface. More particularly, the methods of the present invention achieve improved correct assembly and good stability of particular Fabs containing kappa LC constant domains (Cκ). Even more particular, the methods of the present invention allow the binding activities of Fabs of two distinct therapeutic antibodies to be combined in a single fully IgG bi-specific antibody compound. Further, the designs and methods of the present invention may be combined with other known methods for improving HC-LC specific assembly, and/or HC-HC heterodimerization, thus further facilitating assembly of fully IgG BsAbs.

Thus, the present invention provides a method for producing a first and second fragment, antigen binding (Fab) comprising: (1) co-expressing in a host cell: (a) a first nucleic acid sequence encoding both a first heavy chain variable domain and a first human IgG heavy chain constant $C_H1$ domain, wherein said first human IgG heavy chain constant $C_H1$ domain comprises an alanine substituted at (or an alanine at) residue 145; (b) a second nucleic acid sequence encoding both a first light chain variable domain and a first human light chain kappa constant domain, wherein said first human light chain kappa constant domain comprises an arginine substituted at (or an arginine at) residue 131; (c) a third nucleic acid encoding both a second heavy chain variable domain and a second human IgG heavy chain constant $C_H1$ domain, wherein said second human IgG heavy chain constant $C_H1$ domain is the WT sequence; and (d) a fourth nucleic acid encoding both a second light chain variable domain and a second human light chain kappa constant domain, wherein said second human light chain kappa constant domain is the WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and human IgG $C_H1$ constant domains and said first and second light chain variable and human kappa constant domains are produced; and (3) recovering from said host cell a first and second Fab wherein said first Fab comprises said first heavy chain variable and human IgG constant $C_H1$ domains and said first light chain variable and human kappa constant domains, and said second Fab comprises said second heavy chain variable and human IgG constant $C_H1$ domains and said second light chain variable and human kappa constant domains. More particular to this embodiment, the present invention provides a method wherein said first human IgG heavy chain constant $C_H1$ domain further comprises a glutamic acid substituted at (or a glutamic acid at) residue 221 and said first human light chain kappa constant domain further comprises a lysine substituted at (or a lysine at) residue 123. Even more particular to either of the afore-mentioned embodiments, the present invention provides a method wherein, said first human IgG heavy chain constant $C_H1$ domain further comprises an alanine or glycine substituted at (or an alanine or glycine at) residue 188 and said first human light chain kappa constant domain further comprises an isoleucine substituted at (or an isoleucine at) residue 176.

As another embodiment, the present invention provides a method for producing a first and second fragment, antigen binding (Fab) comprising: (1) co-expressing in a host cell: (a) a first nucleic acid sequence encoding both a first heavy chain variable domain and a first human IgG heavy chain constant CHI domain, wherein said first human IgG heavy chain constant $C_H1$ domain comprises an alanine substituted at (or an alanine at) residue 145 and an alanine or glycine substituted at (or an alanine or glycine at) residue 188; (b) a second nucleic acid sequence encoding both a first light chain variable domain and a first human light chain kappa constant domain, wherein said first human light chain kappa constant domain comprises an arginine substituted at (or an arginine at) residue 131 and an isoleucine substituted at (or an isoleucine at) residue 176; (c) a third nucleic acid encoding both a second heavy chain variable domain and a second human IgG heavy chain constant $C_H1$ domain, wherein said second human IgG heavy chain constant CHI domain comprises a glutamic acid substituted at (or a glutamic acid at) residue 221; and (d) a fourth nucleic acid encoding both a second light chain variable domain and a second human light chain kappa constant domain, wherein said second human light chain kappa constant domain comprises a lysine substituted at (or a lysine at) residue 123, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and human IgG CHI constant domains and said first and second light chain variable and human kappa constant domains are produced; and (3) recovering from said host cell a first and second Fab wherein said first Fab comprises said first heavy chain variable and human IgG constant $C_H1$ domains and said first light chain variable and human kappa constant domains, and said second Fab comprises said second heavy chain variable and human IgG constant $C_H1$ domains and said second light chain variable and human kappa constant domains.

The $C_H1/C\kappa$ interface designs of the methods as described above may also be combined with designs in $V_H/V_L$ interface as described in Lewis et al. (2014) and WO2014/150973. Thus, as another particular embodiment, the present invention provides any of the afore-mentioned methods wherein: (a) said first heavy chain variable domain comprises a glutamic acid substituted at (or a glutamic acid at) the residue which is four amino acids upstream of the first residue of HFR3 according to Kabat Numbering and a lysine substituted at (or a lysine at) residue 39; (b) said first light chain variable domain is kappa isotype and comprises an arginine substituted at (or an arginine at) residue 1 and an aspartic acid substituted at (or an aspartic acid at) residue 38; (c) said second heavy chain variable domain comprises a tyrosine substituted at (or a tyrosine at) residue 39 and an arginine substituted at (or an arginine at) residue 105; and (d) said second light chain variable domain is kappa isotype and comprises an arginine substituted at (or an arginine at) residue 38 and an aspartic acid substituted at (or an aspartic acid at) residue 42. Alternately, the present invention provides any of the afore-mentioned methods wherein: (a) said first heavy chain variable domain comprises a tyrosine substituted at (or a tyrosine at) residue 39 and an arginine substituted at (or an arginine at) residue 105; (b) said first light chain variable domain is kappa isotype and comprises an arginine substituted at (or an arginine at) residue 38 and an aspartic acid substituted at (or an aspartic acid at) residue 42; (c) said second heavy chain variable domain comprises a glutamic acid substituted at (or a glutamic acid at) the residue which is four amino acids upstream of the first residue of HFR3 according to Kabat Numbering and a lysine substituted at (or a lysine at) residue 39; and (d) said second light chain variable domain is kappa isotype and comprises an arginine substituted at (or an arginine at) residue 1 and an aspartic acid substituted at (or an aspartic acid at) residue 38.

Even more particular, the present invention provides any of the afore-mentioned methods wherein each of said first and second human IgG heavy chain constant CHI domains are individually IgG1 or IgG4 isotype. The present invention also provides any of the afore-mentioned methods wherein each of said first and second human IgG heavy chain constant $C_H1$ domains are IgG1 isotype. The present invention also provides any of the afore-mentioned methods wherein each of said first and second human IgG heavy chain constant $C_H1$ domains are IgG4 isotype.

Further still, the present invention provides any of the afore-mentioned methods wherein: (a) said first human IgG heavy chain constant $C_H1$ domain amino acid sequence is (SEQ ID NO:67), said first human light chain kappa constant domain amino acid sequence is (SEQ ID NO:57), said second human IgG heavy chain constant $C_H1$ domain amino acid sequence is (SEQ ID NO:66), and said second human light chain kappa constant domain amino acid sequence is (SEQ ID NO:2); or (b) said first human IgG heavy chain constant $C_H1$ domain amino acid sequence is (SEQ ID NO:68), said first human light chain kappa constant domain amino acid sequence is (SEQ ID NO:59), said second human IgG heavy chain constant $C_H1$ domain amino acid sequence is (SEQ ID NO:69), and said second human light chain kappa constant domain amino acid sequence is (SEQ ID NO:61); or (c) said first human IgG heavy chain constant $C_H1$ domain amino acid sequence is (SEQ ID NO:70), said first human light chain kappa constant domain amino acid sequence is (SEQ ID NO:59), said second human IgG heavy chain constant $C_H1$ domain amino acid sequence is (SEQ ID NO:69), and said second human light chain kappa constant domain amino acid sequence is (SEQ ID NO:61); or (d) said first human IgG heavy chain constant $C_H1$ domain amino acid sequence is (SEQ ID NO:71), said first human light chain kappa constant domain amino acid sequence is (SEQ ID NO:64), said second human IgG heavy chain constant $C_H1$ domain amino acid sequence is (SEQ ID NO:66), and said second human light chain kappa constant domain amino acid sequence is (SEQ ID NO:2); or (e) said first human IgG heavy chain constant $C_H1$ domain amino acid sequence is (SEQ ID NO:72), said first human light chain kappa constant domain amino acid sequence is (SEQ ID NO:64), said second human IgG heavy chain constant $C_H1$ domain amino acid sequence is (SEQ ID NO:66), and said second human light chain kappa constant domain amino acid sequence is (SEQ ID NO:2).

Further, the present invention provides any of the afore-mentioned methods wherein each of said first and second light chain variable domains is human kappa isotype.

The present invention also provides a method for producing an IgG bispecific antibody comprising: (1) co-expressing in a host cell: (a) a first nucleic acid sequence encoding both a first heavy chain variable domain and a first human IgG heavy chain constant region, wherein said first human IgG heavy chain constant region comprises a $C_H1$ constant domain comprising an alanine substituted at (or an alanine at) residue 145; (b) a second nucleic acid sequence encoding both a first light chain variable domain and a first human light chain kappa constant domain, wherein said first human light chain kappa constant domain comprises an arginine substituted at (or an arginine at) residue 131; (c) a third nucleic acid encoding both a second heavy chain variable domain and a second human IgG heavy chain constant region, wherein said second human IgG heavy chain constant region comprises a $C_H1$ constant domain that is the WT sequence; and (d) a fourth nucleic acid encoding both a second light chain variable domain and a second human light chain kappa constant domain, wherein said second human light chain kappa constant domain is the WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and human IgG $C_H1$ constant domains and said first and second light chain variable and human kappa constant domains are produced; and (3) recovering from said host cell an IgG bispecific antibody comprising a first and second fragment, antigen binding (Fab) wherein said first Fab comprises said first heavy chain variable and human IgG constant $C_H1$ domains and said first light chain variable and human kappa constant domains, and said second Fab comprises said second heavy chain variable and human IgG constant $C_H1$ domains and said second light chain variable and human kappa constant domains. More particular to this embodiment, the present invention provides a method for producing an IgG bispecific antibody wherein said first human IgG heavy chain constant $C_H1$ domain further comprises a glutamic acid substituted at (or a glutamic acid at) residue 221 and said first human light chain kappa constant domain further comprises a lysine substituted at (or a lysine at) residue 123. Even more particular to either of the afore-mentioned embodiments, the present invention provides a method for producing an IgG bispecific antibody wherein, said first human IgG heavy chain constant $C_H1$ domain further comprises an alanine or glycine substituted at (or an alanine or glycine at) residue 188 and said first human light chain kappa constant domain further comprises an isoleucine substituted at (or an isoleucine at) residue 176.

As another embodiment, the present invention provides a method for producing an IgG bispecific antibody comprising: (1) co-expressing in a host cell: (a) a first nucleic acid sequence encoding both a first heavy chain variable domain and a first human IgG heavy chain constant region, wherein said first human IgG heavy chain constant region comprises a $C_H1$ constant domain comprising an alanine substituted at (or an alanine at) residue 145 and an alanine or glycine substituted at (or an alanine or glycine at) residue 188; (b) a second nucleic acid sequence encoding both a first light chain variable domain and a first human light chain kappa constant domain, wherein said first human light chain kappa constant domain comprises an arginine substituted at (or an arginine at) residue 131 and an isoleucine substituted at (or an isoleucine at) residue 176; (c) a third nucleic acid encoding both a second heavy chain variable domain and a second human IgG heavy chain constant region, wherein said second IgG heavy chain constant region comprises a $C_H1$ domain comprising a glutamic acid substituted at (or a glutamic acid at) residue 221; and (d) a fourth nucleic acid encoding both a second light chain variable domain and a second human light chain kappa constant domain, wherein said second human light chain kappa comprises a lysine substituted at (or a lysine at) residue 123, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and human IgG $C_H1$ constant domains and said first and second light chain variable and human kappa constant domains are produced; and (3) recovering from said host cell an IgG bispecific antibody comprising a first and second Fab wherein said first Fab comprises said first heavy chain variable and human IgG constant $C_H1$ domains and said first light chain variable and human kappa constant domains, and said second Fab comprises said second heavy chain variable and human IgG constant $C_H1$ domains and said second light chain variable and human kappa constant domains.

The $C_H1/C\kappa$ interface designs of the methods for producing an IgG bispecific antibody, as described above, may also be combined with designs in $V_H/V_L$ interface as described in Lewis el al. (2014) and WO2014/150973. Thus, as another embodiment, the present invention provides any of the afore-mentioned methods for producing an IgG bispecifc antibody wherein: (a) said first heavy chain variable domain comprises a glutamic acid substituted at (or a glutamic acid at) the residue which is four amino acids upstream of the first residue of HFR3 according to Kabat Numbering and a lysine substituted at (or a lysine at) residue 39; (b) said first light chain variable domain is kappa isotype and comprises an arginine substituted at (or an arginine at) residue 1 and an aspartic acid substituted at (or an aspartic acid at) residue 38; (c) said second heavy chain variable domain comprises a tyrosine substituted at (or a tyrosine at) residue 39 and an arginine substituted at (or an arginine at) residue 105; and (d) said second light chain variable domain is kappa isotype and comprises an arginine substituted at (or an arginine at) residue 38 and an aspartic acid substituted at (or an aspartic acid at) residue 42. Alternately, the present invention provides any of the afore-mentioned methods for producing an IgG bispecifc antibody wherein: (a) said first heavy chain variable domain comprises a tyrosine substituted at (or a tyrosine at) residue 39 and an arginine substituted at (or an arginine at) residue 105; (b) said first light chain variable domain is kappa isotype and comprises an arginine substituted at (or an arginine at) residue 38 and an aspartic acid substituted at (or an aspartic acid at) residue 42; (c) said second heavy chain variable domain comprises a glutamic acid substituted at (or a glutamic acid at) the residue which is four amino acids upstream of the first residue of HFR3 according to Kabat Numbering and a lysine substituted at (or a lysine at) residue 39; and (d) said second light chain variable domain is kappa isotype and comprises an arginine substituted at (or an arginine at) residue 1 and an aspartic acid substituted at (or an aspartic acid at) residue 38.

The $C_H1/C\kappa$ interface designs of the methods for producing an IgG bispecific antibody, as described above, may also be combined with designs in $C_H3/C_H3$ interface as described in Leaver-Fay A., et al. (2016), Structure; 24; 641-651 and WO 2016/118742 A1. Thus, as a further particular embodiment, the present invention provides any of the afore-mentioned methods for producing an IgG bispecific antibody wherein: (a) one of said first or second human IgG constant regions comprises a $C_H3$ domain comprising an alanine substituted at (or an alanine at) residue 407; and the other of said first or second human IgG constant regions comprises a $C_H3$ domain comprising a valine substituted at (or a valine at) residue 366 and a valine substituted at (or a valine at) residue 409; or (b) one of said first or second human IgG constant regions comprises a $C_H3$ domain comprising an alanine substituted at (or an alanine at) residue 407 and a methionine substituted at (or a methionine at) residue 399; and the other of said first or second human IgG constant regions comprises a $C_H3$ domain comprising a valine substituted at (or a valine at) residue 366 and a valine substituted at (or a valine at) residue 409; or (c) one of said first or second human IgG constant regions comprises a $C_H3$ domain comprising an alanine substituted at (or an alanine at) residue 407, a methionine substituted at (or a methionine at) residue 399, and an aspartic acid substituted at (or an aspartic acid at) residue 360; and the other of said first or second human IgG constant regions comprises a $C_H3$ domain comprising a valine substituted at (or a valine at) residue 366, a valine substituted at (or a valine at) residue 409, and an arginine substituted at (or an arginine at) residues 345 and 347; or (d) one of said first or second human IgG constant regions comprises a $C_H3$ domain comprising an alanine substituted at (or an alanine at) residue 407, an aspartic acid substituted at (or an aspartic acid at) residue 357, and a glutamine substituted at (or a glutamine at) residue 364; and the other of said first or second human IgG constant regions comprises a $C_H^3$ domain comprising a valine substituted at (or a valine at) residue 366, a valine substituted at (or a valine at) residue 409, a serine substituted at (or a serine at) residue 349, and a tyrosine substituted at (or a tyrosine at) residue 370; or (e) one of said first or second human IgG constant regions comprises a $C_H3$ domain comprising an alanine substituted at (or an alanine at) residue 407, an aspartic acid substituted at (or an aspartic acid at) residue 357, and a glutamine substituted at (or a glutamine at) residue 364; and the other of said first or second human IgG constant regions comprises a $C_H3$ domain comprising a methionine substituted at (or a methionine at) residue 366, a valine substituted at (or a valine at) residue 409, a serine substituted at (or a serine at) residue 349, and a tyrosine substituted at (or a tyrosine at) residue 370; or (f) one of said first or second human IgG constant regions comprises a $C_H3$ domain comprising an alanine substituted at (or an alanine at) residue 407, an aspartic acid substituted at (or an aspartic acid at) residue 357, and an arginine substituted at (or an arginine at) residue 364; and the other of said first or second human IgG constant regions comprises a $C_H3$ domain comprising a valine substituted at (or a valine at) residue 366, a valine substituted at (or a valine at) residue 409, a serine substituted at (or a serine at) residue 349, and a tyrosine substituted at (or a tyrosine at) residue 370; or (g) one of said first or second human IgG constant regions comprises a $C_H3$ domain comprising an alanine substituted at (or an alanine at) residue 407, a glycine substituted at (or a glycine at) residue 356, an aspartic acid substituted at (or an aspartic acid at) residue 357, and a glutamine substituted at (or a glutamine at) residue 364; and the other of said first or second human IgG constant regions comprises a $C_H3$ domain comprising a valine substituted at (or a valine at) residue 366, a valine substituted at (or a valine at) residue 409, a serine substituted at (or a serine at) residue 349, and a tyrosine substituted at (or a tyrosine at) residue 370; or (h) one of said first or second human IgG constant regions comprises a $C_H3$ domain comprising an alanine substituted at (or an alanine at) residue 407, a glycine substituted at (or a glycine at) residue 356, an aspartic acid substituted at (or an aspartic acid at) residue 357, and a glutamine substituted at (or a glutamine at) residue 364; and the other of said first or second human IgG constant regions comprises a $C_H3$ domain comprising a methionine substituted at (or a methionine at) residue 366, a valine substituted at (or a valine at) residue 409, a serine substituted at (or a serine at) residue 349, and a tyrosine substituted at (or a tyrosine at) residue 370; or (i) one of said first or second human IgG constant regions comprises a $C_H^3$ domain comprising an alanine substituted at (or an alanine at) residue 407, an aspartic acid substituted at (or an aspartic acid at) residue 357, and an arginine substituted at (or an arginine at) residue 364; and the other of said first or second human IgG constant regions comprises a $C_H3$ domain comprising a methionine substituted at (or a methionine at) residue 366, a valine substituted at (or a valine at) residue 409, a serine substituted at (or a serine at) residue 349, and a tyrosine substituted at (or a tyrosine at) residue 370.

As yet another embodiment, the present invention provides any of the afore-mentioned methods for producing an IgG bispecifc antibody wherein each of said first and second human IgG heavy chain constant regions are individually IgG1 or IgG4 isotype, and more particularly each are IgG1, or each are IgG4.

Further still, the present invention provides any of the afore-mentioned methods for producing an IgG bispecifc antibody wherein: (a) said first human IgG heavy chain constant $C_H1$ domain amino acid sequence is (SEQ ID NO:67), said first human light chain kappa constant domain amino acid sequence is (SEQ ID NO:57), said second human IgG heavy chain constant $C_H1$ domain amino acid sequence is (SEQ ID NO:66), and said second human light chain kappa constant domain amino acid sequence is (SEQ ID NO:2); or (b) said first human IgG heavy chain constant CHI domain amino acid sequence is (SEQ ID NO:68), said first human light chain kappa constant domain amino acid sequence is (SEQ ID NO:59), said second human IgG heavy chain constant $C_H1$ domain amino acid sequence is (SEQ ID NO:69), and said second human light chain kappa constant domain amino acid sequence is (SEQ ID NO:61); or (c) said first human IgG heavy chain constant $C_H1$ domain amino acid sequence is (SEQ ID NO:70), said first human light chain kappa constant domain amino acid sequence is (SEQ ID NO:59), said second human IgG heavy chain constant CHI domain amino acid sequence is (SEQ ID NO:69), and said second human light chain kappa constant domain amino acid sequence is (SEQ ID NO:61); or (d) said first human IgG heavy chain constant CHI domain amino acid sequence is (SEQ ID NO:71), said first human light chain kappa constant domain amino acid sequence is (SEQ ID NO:64), said second human IgG heavy chain constant $C_H1$ domain amino acid sequence is (SEQ ID NO:66), and said second human light chain kappa constant domain amino acid sequence is (SEQ ID NO:2); or (e) said first human IgG heavy chain constant CHI domain amino acid sequence is (SEQ ID NO:72), said first human light chain kappa constant domain amino acid sequence is (SEQ ID NO:64), said second human IgG heavy chain constant $C_H1$ domain amino acid sequence is (SEQ ID NO:66), and said second human light chain kappa constant domain amino acid sequence is (SEQ ID NO:2).

As a further particular embodiment, the present invention provides any of the afore-mentioned methods for producing an IgG bispecific antibody wherein: (a) one of said first or second human IgG constant regions comprises an Fc domain amino acid sequence that is (SEQ ID NO:83); and the other of said first or second human IgG constant regions comprises an Fc domain amino acid sequence that is (SEQ ID NO:78); or (b) one of said first or second human IgG constant regions comprises an Fc domain amino acid sequence that is (SEQ ID NO:74); and the other of said first or second human IgG constant regions comprises an Fc domain amino acid sequence that is (SEQ ID NO:78); or (c) one of said first or second human IgG constant regions comprises an Fc domain amino acid sequence that is (SEQ ID NO:75); and the other of said first or second human IgG constant regions comprises an Fc domain amino acid sequence that is (SEQ ID NO:79); or (d) one of said first or second human IgG constant regions comprises an Fc domain amino acid sequence that is (SEQ ID NO:76); and the other of said first or second human IgG constant regions comprises an Fc domain amino acid sequence that is (SEQ ID NO:80); or (e) one of said first or second human IgG constant regions comprises an Fc domain amino acid sequence that is (SEQ ID NO:77); and the other of said first or second human IgG constant regions comprises an Fc domain amino acid sequence that is (SEQ ID NO:80); or (f) one of said first or second human IgG constant regions comprises an Fc domain amino acid sequence that is (SEQ ID NO:76); and the other of said first or second human IgG constant regions comprises an Fc domain amino acid sequence that is (SEQ ID NO:82); or (g) one of said first or second human IgG constant regions comprises an Fc domain amino acid sequence that is (SEQ ID NO:76); and the other of said first or second human IgG constant regions comprises an Fc domain amino acid sequence that is (SEQ ID NO:81); or (h) one of said first or second human IgG constant regions comprises an FEc domain amino acid sequence that is (SEQ ID NO:77); and the other of said first or second human IgG constant regions comprises an Fc domain amino acid sequence that is (SEQ ID NO:81); or (i) one of said first or second human IgG constant regions comprises an Fc domain amino acid sequence that is (SEQ ID NO:77); and the other of said first or second human IgG constant regions comprises an Fc domain amino acid sequence that is (SEQ ID NO:82).

Further, the present invention provides any of the afore-mentioned methods for producing an IgG bispecifc antibody wherein each of said first and second light chain variable domains is human kappa isotype.

The present invention also provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an alanine substituted at (or an alanine at) residue 145 of the $C_H1$ domain; (b) a first light chain, wherein said first light chain comprises a first variable domain ($V_L$) and a first human light chain kappa constant domain ($C_K$), wherein said first human light chain kappa constant domain comprises an arginine substituted at (or an arginine at) residue 131; (c) a second heavy chain, wherein said second heavy chain comprises a second variable domain (Vg) and a second human IgG1 or IgG4 constant region, wherein said second human IgG1 or IgG4 heavy chain constant region comprises a $C_H1$ constant domain that is the WT sequence; and (d) a second light chain, wherein said second light chain comprises a second variable domain ($V_L$) and a second human light chain kappa constant domain ($C_K$), wherein said second human light chain kappa constant domain is the WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen. More particular to this embodiment, the present invention provides an IgG bispecific antibody wherein said first human IgG1 or IgG4 heavy chain constant region $C_H1$ domain further comprises a glutamic acid substituted at (or a glutamic acid at) residue 221 and said first human light chain kappa constant domain further comprises a lysine substituted at (or a lysine at) residue 123. Even more particular to either of the afore-mentioned embodiments, the present invention provides an IgG bispecific antibody wherein said first human IgG1 or IgG4 heavy chain constant region $C_H1$ domain further comprises an alanine or glycine substituted at (or an alanine or glycine at) residue 188 and said first human light chain kappa constant domain further comprises an isoleucine substituted at (or an isoleucine at) residue 176.

The present invention also provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an alanine substituted at (or an alanine at) residue 145 and an alanine or glycine substituted at (or an alanine or glycine at) residue 188 of the CHI domain; (b) a first light chain, wherein said first light chain comprises a first variable domain ($V_L$) and a first human light chain kappa constant domain ($C_K$), wherein said first human light chain kappa constant domain comprises an arginine substituted at (or an arginine at) residue 131 and an isoleucine substituted at (or an isoleucine at) residue 176; (c) a second heavy chain, wherein said second heavy chain comprises a second variable domain ($V_H$) and a second human IgG1 or IgG4 constant region, wherein said second human IgG1 or IgG4 heavy chain constant region comprises a glutamic acid substituted at (or a glutamic acid at) residue 221 of the $C_H1$ constant domain; and (d) a second light chain, wherein said second light chain comprises a second variable domain ($V_L$) and a second human light chain kappa constant domain ($C_K$), wherein said second human light chain kappa constant domain comprises a lysine substituted at (or a lysine at) residue 123, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen.

The $C_H1$/Cκ interface designs of the IgG bispecific antibodies as described above may also be combined with designs in $V_H/V_L$ interface as described in Lewis et al. (2014) and WO2014/150973. Thus, as another embodiment, the present invention provides any of the afore-mentioned IgG bispecifc antibodies wherein: (a) said first heavy chain variable domain comprises a glutamic acid substituted at (or a glutamic acid at) the residue which is four amino acids upstream of the first residue of HFR3 according to Kabat Numbering and a lysine substituted at (or a lysine at) residue 39; (b) said first light chain variable domain is kappa isotype and comprises an arginine substituted at (or an arginine at) residue 1 and an aspartic acid substituted at (or an aspartic acid at) residue 38; (c) said second heavy chain variable domain comprises a tyrosine substituted at (or a tyrosine at) residue 39 and an arginine substituted at (or an arginine at) residue 105; and (d) said second light chain variable domain is kappa isotype and comprises an arginine substituted at (or an arginine at) residue 38 and an aspartic acid substituted at (or an aspartic acid at) residue 42. Alternately, the present invention provides any of the afore-mentioned IgG bispecifc antibodies wherein: (a) said first heavy chain variable domain comprises a tyrosine substituted at (or a tyrosine at) residue 39 and an arginine substituted at (or an arginine at) residue 105; (b) said first light chain variable domain is kappa isotype and comprises an arginine substituted at (or an arginine at) residue 38 and an aspartic acid substituted at (or an aspartic acid at) residue 42; (c) said second heavy chain variable domain comprises a glutamic acid substituted at (or a glutamic acid at) the residue which is four amino acids upstream of the first residue of HFR3 according to Kabat Numbering and a lysine substituted at (or a lysine at) residue 39; and (d) said second light chain variable domain is kappa isotype and comprises an arginine substituted at (or an arginine at) residue 1 and an aspartic acid substituted at (or an aspartic acid at) residue 38.

The $C_H1/C\kappa$ interface designs of the IgG bispecific antibodies, as described above, may also be combined with designs in $C_H3/C_H3$ interface as described in Leaver-Fay A., et al. (2016), Structure; 24; 641-651 and WO 2016/118742 A1. Thus, as a further particular embodiment, the present invention provides any of the afore-mentioned IgG bispecific antibodies wherein: (a) one of said first or second human IgG1 or IgG4 constant regions comprises a $C_H3$ domain comprising an alanine substituted at (or an alanine at) residue 407; and the other of said first or second human IgG1 or IgG4 constant regions comprises a $C_H3$ domain comprising a valine substituted at (or a valine at) residue 366 and a valine substituted at (or a valine at) residue 409; or (b) one of said first or second human IgG1 or IgG4 constant regions comprises a $C_H3$ domain comprising an alanine substituted at (or an alanine at) residue 407 and a methionine substituted at (or a methionine at) residue 399; and the other of said first or second human IgG1 or IgG4 constant regions comprises a $C_H^3$ domain comprising a valine substituted at (or a valine at) residue 366 and a valine substituted at (or a valine at) residue 409; or (c) one of said first or second human IgG1 or IgG4 constant regions comprises a $C_H^3$ domain comprising an alanine substituted at (or an alanine at) residue 407, a methionine substituted at (or a methionine at) residue 399, and an aspartic acid substituted at (or an aspartic acid at) residue 360; and the other of said first or second human IgG1 or IgG4 constant regions comprises a $C_H3$ domain comprising a valine substituted at (or a valine at) residue 366, a valine substituted at (or a valine at) residue 409, and an arginine substituted at (or an arginine at) residues 345 and 347; or (d) one of said first or second human IgG1 or IgG4 constant regions comprises a $C_H3$ domain comprising an alanine substituted at (or an alanine at) residue 407, an aspartic acid substituted at (or an aspartic acid at) residue 357, and a glutamine substituted at (or a glutamine at) residue 364; and the other of said first or second human IgG1 or IgG4 constant regions comprises a $C_H3$ domain comprising a valine substituted at (or a valine at) residue 366, a valine substituted at (or a valine at) residue 409, a serine substituted at (or a serine at) residue 349, and a tyrosine substituted at (or a tyrosine at) residue 370; or (e) one of said first or second human IgG1 or IgG4 constant regions comprises a $C_H3$ domain comprising an alanine substituted at (or an alanine at) residue 407, an aspartic acid substituted at (or an aspartic acid at) residue 357, and a glutamine substituted at (or a glutamine at) residue 364; and the other of said first or second human IgG1 or IgG4 constant regions comprises a $C_H3$ domain comprising a methionine substituted at (or a methionine at) residue 366, a valine substituted at (or a valine at) residue 409, a serine substituted at (or a serine at) residue 349, and a tyrosine substituted at (or a tyrosine at) residue 370; or (f) one of said first or second human IgG1 or IgG4 constant regions comprises a $C_H3$ domain comprising an alanine substituted at (or an alanine at) residue 407, an aspartic acid substituted at (or an aspartic acid at) residue 357, and an arginine substituted at (or an arginine at) residue 364; and the other of said first or second human IgG1 or IgG4 constant regions comprises a $C_H^3$ domain comprising a valine substituted at (or a valine at) residue 366, a valine substituted at (or a valine at) residue 409, a serine substituted at (or a serine at) residue 349, and a tyrosine substituted at (or a tyrosine at) residue 370; or (g) one of said first or second human IgG1 or IgG4 constant regions comprises a $C_H^3$ domain comprising an alanine substituted at (or an alanine at) residue 407, a glycine substituted at (or a glycine at) residue 356, an aspartic acid substituted at (or an aspartic acid at) residue 357, and a glutamine substituted at (or a glutamine at) residue 364; and the other of said first or second human IgG1 or IgG4 constant regions comprises a $C_H3$ domain comprising a valine substituted at (or a valine at) residue 366, a valine substituted at (or a valine at) residue 409, a serine substituted at (or a serine at) residue 349, and a tyrosine substituted at (or a tyrosine at) residue 370; or (h) one of said first or second human IgG1 or IgG4 constant regions comprises a $C_H3$ domain comprising an alanine substituted at (or an alanine at) residue 407, a glycine substituted at (or a glycine at) residue 356, an aspartic acid substituted at (or an aspartic acid at) residue 357, and a glutamine substituted at (or a glutamine at) residue 364; and the other of said first or second human IgG1 or IgG4 constant regions comprises a $C_H3$ domain comprising a methionine substituted at (or a methionine at) residue 366, a valine substituted at (or a valine at) residue 409, a serine substituted at (or a serine at) residue 349, and a tyrosine substituted at (or a tyrosine at) residue 370; or (i) one of said first or second human IgG1 or IgG4 constant regions comprises a $C_H3$ domain comprising an alanine substituted at (or an alanine at) residue 407, an aspartic acid substituted at (or an aspartic acid at) residue 357, and an arginine substituted at (or an arginine at) residue 364; and the other of said first or second human IgG1 or IgG4 constant regions comprises a $C_H3$ domain comprising a methionine substituted at (or a methionine at) residue 366, a valine substituted at (or a valine at) residue 409, a serine substituted at (or a serine at) residue 349, and a tyrosine substituted at (or a tyrosine at) residue 370.

Even more particular, the present invention provides any of the afore-mentioned IgG bispecifc antibodies wherein one of said first or second human IgG1 or IgG4 heavy chain constant regions is IgG1 isotype and the other of said first or second human IgG1 or IgG4 heavy chain constant regions is IgG4 isotype. The present invention also provides any of the afore-mentioned IgG bispecifc antibodies wherein each of said first and second human IgG1 or IgG4 heavy chain constant regions are IgG1 isotype. The present invention also provides any of the afore-mentioned IgG bispecifc antibodies wherein each of said first and second human IgG1 or IgG4 heavy chain constant regions are IgG4 isotype.

Further still, the present invention provides any of the afore-mentioned IgG bispecifc antibodies wherein: (a) said first human IgG heavy chain constant region comprises a $C_H1$ domain amino acid sequence that is (SEQ ID NO:67), said first human light chain kappa constant domain amino acid sequence is (SEQ ID NO:57), said second human IgG heavy chain constant region comprises a $C_H1$ domain amino acid sequence that is (SEQ ID NO:66), and said second human light chain kappa constant domain amino acid sequence is (SEQ ID NO:2); or (b) said first human IgG heavy chain constant region comprises a $C_H1$ domain amino acid sequence that is (SEQ ID NO:68), said first human light chain kappa constant domain amino acid sequence is (SEQ ID NO:59), said second human IgG heavy chain constant region comprises a $C_H1$ domain amino acid sequence that is (SEQ ID NO:69), and said second human light chain kappa constant domain amino acid sequence is (SEQ ID NO:61); or (c) said first human IgG heavy chain constant region comprises a $C_H1$ domain amino acid sequence that is (SEQ ID NO:70), said first human light chain kappa constant domain amino acid sequence is (SEQ ID NO:59), said second human IgG heavy chain constant region comprises a $C_H1$ domain amino acid sequence that is (SEQ ID NO:69), and said second human light chain kappa constant domain amino acid sequence is (SEQ ID NO:61); or (d) said first human IgG heavy chain constant region comprises a $C_H1$ domain amino acid sequence that is (SEQ ID NO:71), said first human light chain kappa constant domain amino acid sequence is (SEQ ID NO:64), said second human IgG heavy chain constant region comprises a $C_H1$ domain amino acid sequence that is (SEQ ID NO:66), and said second human light chain kappa constant domain amino acid sequence is (SEQ ID NO:2); or (e) said first human IgG heavy chain constant region comprises a $C_H1$ domain amino acid sequence that is (SEQ ID NO:72), said first human light chain kappa constant domain amino acid sequence is (SEQ ID NO:64), said second human IgG heavy chain constant region comprises a CHI domain amino acid sequence that is (SEQ ID NO:66), and said second human light chain kappa constant domain amino acid sequence is (SEQ ID NO:2).

As a further particular embodiment, the present invention provides any of the afore-mentioned IgG bispecific antibodies wherein: (a) one of said first or second human IgG constant regions comprises an Fc domain amino acid sequence that is (SEQ ID NO:83); and the other of said first or second human IgG constant regions comprises an Fc domain amino acid sequence that is (SEQ ID NO:78); or (b) one of said first or second human IgG constant regions comprises an Fc domain amino acid sequence that is (SEQ ID NO:74); and the other of said first or second human IgG constant regions comprises an Fc domain amino acid sequence that is (SEQ ID NO:78); or (c) one of said first or second human IgG constant regions comprises an Fc domain amino acid sequence that is (SEQ ID NO:75); and the other of said first or second human IgG constant regions comprises an Fc domain amino acid sequence that is (SEQ ID NO:79); or (d) one of said first or second human IgG constant regions comprises an Fc domain amino acid sequence that is (SEQ ID NO:76); and the other of said first or second human IgG constant regions comprises an Fc domain amino acid sequence that is (SEQ ID NO:80); or (e) one of said first or second human IgG constant regions comprises an Fc domain amino acid sequence that is (SEQ ID NO:77); and the other of said first or second human IgG constant regions comprises an Fc domain amino acid sequence that is (SEQ ID NO:80); or (f) one of said first or second human IgG constant regions comprises an Fc domain amino acid sequence that is (SEQ ID NO:76); and the other of said first or second human IgG constant regions comprises an Fc domain amino acid sequence that is (SEQ ID NO:82); or (g) one of said first or second human IgG constant regions comprises an Fc domain amino acid sequence that is (SEQ ID NO:76); and the other of said first or second human IgG constant regions comprises an Fc domain amino acid sequence that is (SEQ ID NO:81); or (h) one of said first or second human IgG constant regions comprises an Fc domain amino acid sequence that is (SEQ ID NO:77); and the other of said first or second human IgG constant regions comprises an Fc domain amino acid sequence that is (SEQ ID NO:81); or (i) one of said first or second human IgG constant regions comprises an Fc domain amino acid sequence that is (SEQ ID NO:77); and the other of said first or second human IgG constant regions comprises an Fc domain amino acid sequence that is (SEQ ID NO:82).

Further, the present invention provides any of the afore-mentioned IgG bispecifc antibodies wherein each of said first and second light chain variable domains is human kappa isotype.

The present invention further provides a first and second Fab, or an IgG bispecfic antibody produced accord to any one of the processes of the present invention. In addition to the preparation of Fabs and fully IgG BsAbs, the methods described herein may also be employed in the preparation of other multi-valent antigen binding compounds. FIG. 1, included herein, provides a schematic diagram of a Fully IgG BsAb, as well as other antigen binding compounds that one of skill in the art could prepare using the $C_H1/C\kappa$ domain designs, or the $C_H/C\kappa$ domain designs plus Fab designs, or the $C_H1/C\kappa$ domain designs plus Fab and $C_H3$ designs as described herein.

The present invention further provides nucleic acid sequences encoding the first and second heavy chains and the first and second light chains of any of the Fabs or IgG BsAbs of the present invention. In addition, the present invention also provides vectors comprising nucleic acid sequences encoding the first heavy chain, the first light chain, the second heavy chain and/or the second light chain of any of the Fabs or IgG BsAbs of the present invention. Further still, the present invention provides host cells comprising nucleic acid sequences encoding the first heavy chain, the first light chain, the second heavy chain and the second light chain of any of the Fabs or IgG BsAbs of the present invention.

BRIEF DESCRIPTION OF FIGURES

FIG. 1 provides a schematic diagram of antigen binding compounds that may be prepared using the $C_H1/C\kappa$ domain designs, methods or procedures of the present invention. FIG. 1A provides full IgG bispecfic antibody comprising a HC and LC from a first mAb (denoted mAb1) targeting one antigen and a HC and LC from a second mAb (denoted mAb2) recognizing a different antigen. FIG. 1B provides Fab-Fab construct comprising a Fab from first mAb (mAb1) and a Fab from second mAb (mAb2). FIG. 1C provides alternate bispecific constructs comprising a first mAb (mAb1) and Fab fragments from a second mAb (mAb2).

DETAILED DESCRIPTION

The general structure of an "IgG antibody" is very well-known. A wild type (WT) antibody of the IgG type is hetero-tetramer of four polypeptide chains (two identical "heavy" chains and two identical "light" chains) that are cross-linked via intra- and inter-chain disulfide bonds. Each heavy chain (HC) is comprised of an N-terminal heavy chain variable region ("$V_H$") and a heavy chain constant region. The heavy chain constant region is comprised of three domains ($C_H1$, $C_H2$, and $C_H3$) as well as a hinge region ("hinge") between the CH1 and $C_H2$ domains. Each light chain (LC) is comprised of an N-terminal light chain variable region ("$V_L$") and a light chain constant region ("$C_L$"). The $V_L$ and $C_L$ regions may be of the kappa ("κ") or lambda ("λ") isotypes ("$C_K$" or "$C_λ$", respectively). Each heavy chain associates with one light chain via interfaces between the heavy chain and light chain variable domains (the $V_H/V_L$ interface) and the heavy chain constant $C_H1$ and light chain constant domains (the $C_H1/C_L$ interface). The association between each of the $V_H$-$C_H1$ and $V_L$-$C_L$ segments forms two identical antigen binding fragments (Fabs) which direct antibody binding to the same antigen or antigenic determinant. Each heavy chain associates with the other heavy chain via interfaces between the hinge-$C_H2$-$C_H3$ segments of each heavy chain, with the association between the two $C_H2$-$C_H3$ segments forming the Fc region of the antibody. Together, each Fab and the Fc form the characteristic "Y-shaped" architecture of IgG antibodies, with each Fab representing the "arms" of the "Y." IgG antibodies can be further divided into subtypes, e.g., IgG1, IgG2, IgG3, and IgG4 which differ by the length of the hinge regions, the number and location of inter- and intra-chain disulfide bonds and the amino acid sequences of the respective HC constant regions.

The variable regions of each heavy chain-light chain pair associate to form binding sites. The heavy chain variable region ($V_H$) and the light chain variable region ($V_L$) can be subdivided into regions of hypervariability, termed complementarity determining regions ("CDRs"), interspersed with regions that are more conserved, termed framework regions ("FR"). Each $V_H$ and $V_L$ is composed of three CDRs and four FRs, arranged from amino-terminus to carboxy-terminus in the following order: FR1, CDR1, FR2, CDR2, FR3, CDR3, FR4. CDRs of the heavy chain may be referred to as "CDRH1, CDRH2, and CDRH3" and the 3 CDRs of the light chain may be referred to as "CDRL1, CDRL2 and CDRL3." The FRs of the heavy chain may be referred to as HFR1, HFR2, HFR3 and HFR4 whereas the FRs of the light chain may be referred to as LFR1, LFR2, LFR3 and LFR4. The CDRs contain most of the residues which form specific interactions with the antigen. As used herein, "antigen" or "antigenic determinant" refers to a target protein to which an IgG antibody binds, or to a particular epitope (on a target protein) to which an IgG antibody binds.

As used herein, the terms "IgG bispecific antibody", "IgG BsAb", "fully IgG bispecific antibody" or "fully IgG BsAb" refer to an antibody of the typical IgG architecture comprising two distinct Fabs, each of which direct binding to a separate antigen or antigenic determinant (i.e., different target proteins or different epitopes on the same target protein), and composed of two distinct IgG heavy chains and two distinct light chains. The $V_H$-$C_H1$ segment of one heavy chain associates with the $V_L$-$C_L$ segment of one light chain to form a "first" Fab, wherein the $V_H$ and $V_L$ domains each comprise 3 CDRs which direct binding to a first antigen. The $V_H$-$C_H1$ segment of the second heavy chain associates with the $V_L$-$C_L$ segment of the second light chain to form a "second" Fab, wherein the $V_H$ and $V_L$ domains each comprise 3 CDRs which direct binding to a second antigen that is different than the first. More particularly, the terms "IgG bispecific antibody", "IgG BsAb", "fully IgG bispecific antibody" or "fully IgG BsAb" refer to antibodies wherein the HC constant regions are composed of $C_H1$, $C_H2$, and $C_H3$ domains of the IgG1, IgG2 or IgG4 subtype, and particularly the human IgG1, human IgG2 or human IgG4. Even more particular, the terms refer to antibodies wherein the HC constant regions are composed of $C_H1$, $C_H2$, and $C_H3$ domains of the IgG1 or IgG4 subtype, and most particularly the human IgG1 or human IgG4 subtype. In addition, as used herein, the terms "IgG bispecific antibody", "IgG BsAb", "fully IgG bispecific antibody" and "fully IgG BsAb" refer to an antibody wherein the constant regions of each individual HC of the antibody are all of the same subtype (for example, each of the $C_H1$, $C_H2$, and $C_H3$ domains of a HC are all of the human IgG1 subtype, or each of the $C_H1$, $C_H2$, and $C_H3$ domains of a HC are all of the IgG2 subtype, or each of the $C_H1$, $C_H2$, and $C_H3$ domains of a HC are all of the IgG4 subtype.) Even more particular, the term refers to an antibody wherein the constant regions of both HCs are all of the same subtype (for example, both HCs have $C_H1$, $C_H2$, and $C_H3$ domains of the human IgG1 subtype, or both HCs have $C_H1$, $C_H2$, and $C_H3$ domains of the human IgG2 subtype, or both HCs have $C_H1$, $C_H2$, and $C_H3$ domains of the human IgG4 subtype.)

The processes and compounds of the present invention comprise designed amino acid modifications at particular residues within the constant and variable regions of heavy chain and light chain polypeptides. As one of ordinary skill in the art will appreciate, various numbering conventions may be employed for designating particular amino acid residues within IgG constant and variable region sequences. Commonly used numbering conventions include the "Kabat Numbering" and "EU Index Numbering" systems. "Kabat Numbering" or "Kabat Numbering system", as used herein, refers to the numbering system devised and set forth by the authors in Kabat et al., *Sequences of Proteins of Immunological Interest*, 5th Ed, Public Health Service, National Institutes of Health, Bethesda, Md. (1991) for designating amino acid residues in both variable and constant domains of antibody heavy chains and light chains. "EU Index Numbering" or "EU Index Numbering system", as used herein, refers to the numbering convention for designating amino acid residues in antibody heavy chain constant domains, and is also set forth in Kabat et al.(1991). Other conventions that include corrections or alternate numbering systems for variable domains include Chothia (Chothia C, Lesk AM (1987), *J Mol Biol* 196: 901-917; Chothia, et al. (1989), *Nature* 342: 877-883), IMGT (Lefranc, et al. (2003), *Dev Comp Immunol* 27: 55-77), and AHo (Honegger A, Pluckthun A (2001) *J Mol Biol* 309: 657-670). These references provide amino acid sequence numbering schemes for immunoglobulin variable regions that define the location of variable region amino acid residues of antibody sequences. Unless otherwise expressly stated herein, all references to immunoglobulin heavy chain variable region (i.e., $V_H$), constant region $C_H1$ and hinge amino acid residues (i.e. numbers) appearing in the Examples and Claims are based on the Kabat Numbering system, as are all references to the light chain $V_L$ and $C_L$ residues. All references to immunoglobulin heavy chain constant region $C_H2$ and $C_H3$ residues (i.e., numbers) are based on the EU Index Numbering system. Thus, as used herein, the phrase "(according to Kabat Numbering)" indicates that the recited amino acid residue number (or position) is numbered in accordance with the Kabat Numbering system, whereas the phrase "(according to EU Index Numbering)" indicates that the recited amino acid residue number (or position) is numbered in accordance with the EU Index Numbering system. With knowledge of the residue number according to Kabat Numbering or EU Index Numbering, one of ordinary skill can apply the teachings of the art to identify amino acid sequence modifications within the present invention, according to any commonly used numbering convention. Note, while the Examples and Claims of the present invention employ Kabat Numbering or EU Index Numbering to identify particular amino acid residues, it is understood that the SEQ ID NOs appearing in the Examples and Sequence Listing accompanying the present application, as generated by Patent In Version 3.5, provide sequential numbering of amino acids within a given polypeptide and, thus, do not conform to the corresponding amino acid residue numbers as provided by Kabat Numbering or EU Index Numbering.

However, as one of skill in the art will also appreciate, CDR sequence length may vary between individual IgG molecules and, further, the numbering of individual residues within a CDR may vary depending on the numbering convention applied. Thus, to reduce ambiguity in the designation of amino acid residues within CDRs, such amino acid residues may be identified by first employing Kabat Numbering to identify the N-terminal (first) amino acid residue of a reference FR (e.g., HFR3). The residue comprising the recited amino acid of the designs may then be denoted as being a fixed number of residues upstream (i.e. in the N-terminal direction) from the first amino acid residue in the reference FR (e.g., HFR3). For example, a Fab design used in combination with the $C_H1/C\kappa$ domain designs of the present invention comprises the placement of a glutamic acid (E) in HCDR2 of a particular HC (i.e., Fab Design "AB" comprising glutamic acid at residue 62 (Kabat Numbering) as described in Lewis, et al. (2014)). The recited glutamic acid is located at the residue position four amino acids upstream of the first amino acid of HFR3, as determined according to Kabat Numbering. In the Kabat Numbering system, amino acid residue X66 is the most N-terminal (first) amino acid residue of variable region heavy chain framework three (HFR3). One of ordinary skill can employ such a strategy to identify the first amino acid residue (most N-terminal) of heavy chain framework three (HFR3) from any human IgG1, IgG2 or IgG4 antibody variable region. Once this landmark is identified, one can then locate the amino acid residue four residues upstream (N-terminal) to this location and replace that amino acid (using standard insertion/deletion methods) with a glutamic acid (E) to achieve the design of the invention. Thus, given any parental immunoglobulin heavy chain amino acid query sequence of interest to use in the processes of the invention, one of ordinary skill in the art of antibody engineering would be able to locate the N-terminal HFR3 residue (according to Kabat Numbering) in said query sequence and then count four amino acid residues upstream therefrom to arrive at the location in HCDR2 that should be a glutamic acid (E).

As used herein, the phrase " . . . a/an [amino acid name] substituted at residue . . . ", in reference to a heavy chain or light chain polypeptide, refers to substitution of the parental amino acid with the indicated amino acid. By way of example, a heavy chain comprising "a lysine substituted at residue 39" refers to a heavy chain wherein the parental amino acid sequence has been mutated to contain a lysine at residue number 39 in place of the parental amino acid. Such mutations may also be represented by denoting a particular amino acid residue number, preceded by the parental amino acid and followed by the replacement amino acid. For example, "Q39K" refers to a replacement of a glutamine at residue 39 with a lysine. Similarly, "39K" refers to replacement of a parental amino acid with a lysine. One of skill in the art will appreciate, however, that as a result of the interface design modifications of the present invention, Fab pairs and fully IgG BsAbs (and processes for their preparation) are therefore provided wherein the component HC and LC amino acid sequences comprise the resulting or "replacement" amino acid at the designated residue. Thus, for example, a heavy chain which "comprises a lysine substituted at residue 39" may alternatively be denoted simply as a heavy chain which "comprises a lysine at residue 39."

As used herein, the phrase "WT" or "WT sequence", in reference to a HC or LC amino acid residue or polypeptide chain, refers to the wild-type or native amino acid or sequence of amino acids that naturally occupies the residue or residues of the polypeptide chain indicated.

Preferably, an IgG BsAb (or Fab pair) of the present invention exists in a homogeneous or substantially homogeneous population. In an embodiment, the IgG BsAb, Fab, or a nucleic acid encoding a component polypeptide sequence of the IgG BsAb or Fab, is provided in "isolated" form. As used herein, the term "isolated" refers to a protein, polypeptide or nucleic acid which is free or substantially free from other macromolecular species found in a cellular environment.

An IgG BsAb or Fab pair of the present invention can be produced using techniques well known in the art, such as recombinant expression in mammalian or yeast cells. In particular, the methods and procedures of the Examples herein may be readily employed. In addition, the IgG BsAbs or Fabs of the present invention may be further engineered to comprise framework regions derived from fully human frameworks. A variety of different human framework sequences may be used in carrying out embodiments of the present invention. As a particular embodiment, the framework regions employed in the processes, as well as the IgG BsAbs and Fab pairs of the present invention are of human origin or are substantially human (at least 95%, 97% or 99% of human origin.) The sequences of framework regions of human origin are known in the art and may be obtained from *The Immunoglobulin Factsbook*, by Marie-Paule Lefranc, Gerard Lefranc, Academic Press 2001, ISBN 012441351.

Expression vectors capable of directing expression of genes to which they are operably linked are well known in the art. Expression vectors contain appropriate control sequences such as promoter sequences and replication initiation sites. They may also encode suitable selection markers as well as signal peptides that facilitate secretion of the desired polypeptide product(s) from a host cell. The signal peptide can be an immunoglobulin signal peptide or a heterologous signal peptide. Nucleic acids encoding desired polypeptides, for example the components of the IgG BsAbs of Fabs prepared according to the processes of the present invention, may be expressed independently using different promoters to which they are operably linked in a single vector or, alternatively, the nucleic acids encoding the desired products may be expressed independently using different promoters to which they are operably linked in separate vectors. In addition, nucleic acids encoding a particular HC/LC pair of the IgG BsAbs or Fabs of the present invention may expressed from a first vector, while the other HC/LC pair is expressed from a second vector. Single expression vectors encoding both HC and both LC components of the IgG BsAbs and Fabs of the present invention may be prepared using standard methods. By way of example, a pE vector encoding a particular HC/LC pair may be engineered to contain a NaeI site 5 prime of a unique SalT site, outside of the HC/LC expression cassette. The vector may then be modified to contain an AscI site 5 prime of the SalT site using standard techniques. For example, the NaeT to SalT region may be PCR amplified using a 3' primer containing the AscI site adjacent to the SalI site, and the resulting fragment cloned into the recipient pE vector. The expression cassette encoding a second HC/LC pair, may then be isolated from a second (donor) vector by digesting the vector at suitable restriction sites. For example, the donor vector may be engineered with MluI and SalI sites to permit isolation of the second expression cassette. This cassette may then be ligated into the recipient vector previously digested at the AscI and SalI sites (as AscI and MluI restriction sites have the same overlapping ends.)

As used herein, a "host cell" refers to a cell that is stably or transiently transfected, transformed, transduced or infected with nucleotide sequences encoding a desired polypeptide product or products. Creation and isolation of host cell lines producing an IgG BsAb or Fab pair of the present invention can be accomplished using standard techniques known in the art.

Mammalian cells are preferred host cells for expression of the IgG BsAb and Fab compounds according to the present invention. Particular mammalian cells include HEK293, NS0, DG-44, and CHO cells. Preferably, assembled proteins are secreted into the medium in which the host cells are cultured, from which the proteins can be recovered and isolated. Medium into which a protein has been secreted may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, hydroxyapatite or mixed modal chromatography. Recovered products may be immediately frozen, for example at −70° C., or may be lyophilized. As one of skill in the art will appreciate, when expressed in certain biological systems, e.g. mammalian cell lines, antibodies are glycosylated in the Fc region unless mutations are introduced in the Fc to reduce glycosylation. In addition, antibodies may be glycosylated at other positions as well.

The object of the present invention is to provide orthogonal interfaces which promote the correct pairing of particular heavy chain Fab fragments (denoted, for example as HC_"A" and HC_"B") with their cognate light chain Fab fragments (i.e., LC_"a" and LC_"b") by introducing particular mutations into heavy chain $C_H$i/light chain $C_K$ domain pairs. As a result of the present invention, increased correct assembly of "Aa" and "Bb" dimers is achieved, relative to the incorrectly assembled "Ab" or "Ba" dimers, when the individual heavy chain and light chain monomers (i.e., "A", "B", "a" and "b" chains) are concomitantly expressed in a host cell. The following Examples further illustrate the invention and provide typical methods and procedures for carrying out various particular embodiments of the present invention. However, it is understood that the Examples are set forth the by way of illustration and not limitation, and that various modifications may be made by one of ordinary skill in the art.

Example 1: Computational and Rational Design of Modifications of $C_H1/C_K$ Interface The identification and design of the particular $C_H1/C_K$ residue mutations resulted from an iterative combination of computational and rational approaches. Starting from the high resolution crystal structure of the human IgG1 $C_H1/C_K$ interface (PDB ID 4NZU from which variable domains are removed) heavy chain residues 122, 124, 139, 141, 143, 145, 174, 188, and 190 and light chain residues 116, 118, 124, 131, 133, 135, and 176 (all according to Kabat Numbering) are selected for initial mutation, allowing substitution to all amino acids except cysteine. Using the Rosetta multistate design (MSD) protocol, and related modeling applications, the resulting sequences are imposed on each of the four dimer and four monomer species to computationally identify potential modifications that favor correct "Aa" and "Bb" dimer formation.

Briefly, the MSD protocol in Rosetta explores sequence space, and for each sequence, calculates an energy for each of several "states" treating phenomena such as van der Waals force and hydrogen bonding forces. The "states" represent different combinations and/or conformations of the various species being modeled. MSD optimizes the sequence side chain conformations, without changing backbone conformations, and aggregates the energies into a fitness metric that reflects how well particular sequences meet design objectives. The fitness values then guide the search through sequence space, and sequences with improved fitness scores can be identified from the simulation. To facilitate the present designs, a fitness function is chosen that favors the binding energies of the correctly paired "Aa" and "Bb" dimers, while disfavoring the binding energies of the mis-paired "Ab" and "Ba" dimers.

To remove an artifact of the fixed-backbone simulation, the weight given to the destabilization of the mis-paired interactions is capped in the fitness function employed in the present methods. The fixed-backbone simulation has a limitation in that it blinds MSD to the possibility that collisions introduced across the interface for mis-paired interactions can be resolved by moving the backbone slightly. Such slight motions can be approximated, however, by using a repertoire of alternate conformations for the mis-paired interactions. A repertoire of alternate backbone conformations is generated by running MSD with only the backbone conformation from the 4NZU crystal structure to identify additional sequences, then feeding these sequences into rigid-body docking using RosettaDock (See Gray, J. J. et al. (2003), J. Mol. Biol.; 331; 281-299). Low-energy backbone conformations identified by rigid-body docking using the Rosetta Interface Analyzer tool. (See Lewis, S. M. & Kuhlman, B. A. (2011), PLoS One 6; e20872 and Stranges, P. B. & Kuhlman, B. A (2013), Protein Sci.; 22; 74-82) are then selected for the repertoire of alternate conformations. This process is iterated multiple times until the difference in measured binding energies following MSD simulation and rigid-body docking is small. After building a repertoire of alternate conformation, several hundred MSD simulations followed by several thousand rigid-body docking runs are performed to create a pool of sequences.

Sequences are selected for further analysis by the total energies and binding energies of the correctly paired interactions and the difference in binding energies between the correctly-paired and mis-paired interactions. These sequences are manually examined to identify frequently occurring pairs of mutations as well as other mutations that often accompany. The identified mutations are divided into multiple families, and within each family, all combinations of possible alternative mutations are enumerated. For each of these sequences, all four dimers are then run through Rosetta's "fast relax" protocol (See Tyka, M. D. et al. (2011), J. Mol. Biol.; 405; 607-618 and Khatib, F. et al. (2011), Proc. Natl. Acad. Sci.; 108; 18949-18953), which allows backbone flexibility as it tries to find low-energy conformations. More than twenty fast relax trajectories are run for each dimer for each sequence and the lowest energy conformation for each dimer is identified. On the basis of the relax simulations, thirty two design pairs (i.e., Aa/Bb pairs) are chosen for an initial round of experimental characterization (Table 1).

TABLE 1

Initial Designs for Experimental Characterization[a]

| Design Name | HC_A ($C_H1$) | LC_a (Cκ) | HC_B ($C_H1$) | LC_b (Cκ) |
|---|---|---|---|---|
| 1.3 | S188G | S176I | — | — |
| 1.4 | S188G | S176I | S188T | — |
| 1.5 | S188A | S176M | — | — |
| 1.6 | S188A | S176M | S188T | — |
| 1.7 | S188G | S176M | — | — |
| 1.8 | S188G | S176M | S188T | — |
| 1.12 | S188G | S176I | S188I | S176G |
| 1.13 | S188A | S176M | S188M | S176A |
| 1.15 | S188I | S176A | — | — |
| 1.18 | S188G | S176I | S188I | S176A |
| 2.3 | K145A | S131R | — | — |
| 2.4 | K145A | S131K | — | — |
| 2.7 | K145S | S131R | — | — |
| 2.8 | K145S | S131K | — | — |
| 3.14 | L143A S188M | V133F | — | — |
| 3.15 | L143A S188M | V133F | S188T | — |
| 3.18 | L143A K145A | S131G V133Y | — | — |
| 3.19 | L143A K145A | S131G V133Y | S188T | — |
| 5.1 | A139L V190G | F118I L135F | — | — |
| 5.2 | A139L V190G | F118V L135F | — | — |
| 6.1 | K145G S188Q | S131R | — | — |
| 6.1 + 1.5inv | K145G S188Q | S131R | S188A | S176M |
| 6.1 + 1.7inv | K145G S188Q | S131R | S188G | S176M |
| 6.2 | F122Y K145G S188Q | S131R | — | — |
| 6.3 | K145G S188Q | S131K | — | — |
| 6.4 | F122Y K145G S188Q | S131K | — | — |
| 7.15 | F174Y V190I | L135V T164V | — | — |
| 7.16 | F174Y V190I | L135V T164V | — | T164S S174V |
| 7.17 | F174Y V190I | L135V T164V | — | T164A S174V |
| 10.1 | K145A S131K | Q124A L143H K145A | F122G | Q124Y S131F |
| 10.9 | K145A S131K | Q124A L143H K145A | F122G | Q124Y S131Y |
| 11.16 | F122G L143Y K145A | Q124F S131W | F122Y S186I V177S | T178I |

[a]All residues numbered according to Kabat Numbering.

Additionally, through visual inspection of the interface, pairs of residues are identified where electrostatic (charge-charge) repulsion mutations could be inserted across the mis-paired interface. Sets of charge mutations were made at these positions and run through Rosetta's fast-relax protocol to ensure that these mutations did not destabilize the correctly-paired interactions. Following these simulations, a set of four candidate mutations (Table 2) are selected for further experimental characterization.

TABLE 2

Manually-identified, charge-pair mutations aimed at destabilizing mis-paired interactions[a]

| Design | HC_A ($C_H1$) | LC_a (Cκ) | HC_B ($C_H1$) | LC_b (Cκ) |
|---|---|---|---|---|
| 12.1 | K221E | E123K | — | — |
| 12.2 | K221E | E123Q | — | — |
| 13.1 | — | T129K | D146K | T129E |
| 13.2 | K145E | T129K/T180K | D146K | T129E/T180E |

[a]All residues numbered according to Kabat Numbering.

After experimental validation of the initial designs using 2D UPLC (as described in the methods of Example 2, below), combinations of mutations from Design families 1 and 2 (Table 1) are also relaxed to identify designs that appear to destabilize both mis-paired interactions. Nine designs, (depicted in Table 3) are selected for experimental characterization.

TABLE 3

Combinations of Initial Designs for Characterization[a]

| Family 1 Design | Family 2 Design | HC_A ($C_H1$) | LC_a (Cκ) | HC_B ($C_H1$) | LC_b (Cκ) |
|---|---|---|---|---|---|
| 1.3 | 2.3 | K145A S188G | S131R S176I | — | — |
| 1.4 | 2.3 | K145A S188G | S131R S176I | S188T | — |
| 1.5 | 2.3 | K145A S188A | S131R S176M | — | — |
| 1.6 | 2.3 | K145A S188A | S131R S176M | S188T | — |
| 1.7 | 2.3 | K145A S188G | S131R S176M | — | — |
| 1.8 | 2.3 | K145A S188G | S131R S176M | S188T | — |
| 1.12 | 2.3 | K145A S188G | S131R S176I | S188I | S176G |
| 1.18 | 2.3 | K145A S188G | S131R S176I | S188I | S176A |
| 1.18 | 2.4 | K145A S188G | S131K S176I | S188I | S176A |

[a]All residues numbered according to Kabat Numbering.

Example 2: Synthesis and Characterization of Constructs Containing $C_H1/C\kappa$ Designs (Lacking Variable Domains)

A. Cloning of Wild-Type $C_H1$-Fc/Cκ Constructs and Incorporation of Designs for Specificity and Stability Screening.

To interrogate the ability of select $C_H1$/Cκ designs (i.e., as described in Example 1) to provide a specific interface that discriminates from wild-type (WT) or alternately designed $C_H1$/Cκ interfaces, it is useful to remove the variable domains to observe $C_H1$/Cκ-specific pairing strengths as previous work in the field showed that the variable domain interface also influences HC/LC pairing specificity. (Lewis et al., 2014 Nature Biotechnol. 32: 191-198) Additionally, two Cκ constructs are constructed (with or without an N-terminal 8×Histag) to enable charge-based separation of different Cκ proteins on a reverse phase HPLC column using using the screening methodology described below. The mutations added to the $C_H1$-Fc/Cκ constructs are designed to enable improved specific assembly of "Aa" and "Bb" HC/LC pairs, relative to the mis-paired "Ab" and "Ba" HC/LC pairs, where 'A' is a first $C_H1$-Fc, 'B' is a second $C_H1$-Fc, 'a' is a first LC Cκ construct designed to pair more specifically with 'A' relative to 'B', and 'b' is a second LC Cκ construct designed to pair more specifically with 'B' relative to 'A' (see Tables 1-3).

Thus, human IgG1 HC and kappa LC constructs lacking variable domain genes are constructed in pEHG1 and pEHK vectors (Lonza), modified in-house for general antibody HC and LC expression. The Wild-Type (no designs) pEHG1_$C_H$1-Fc plasmid is generated by direct recombinase cloning of two separate and overlapping GeneBlocks ("gBlocks", Integrated DNA Technologies (IDT)) coding for the $C_H$1/hinge region and the $C_H$2-$C_H$3, respectively, into the pEHG1 vector using HindIII and EcoRI restriction sites. The hinge-encoding region also contains a factor Xa cleavage site to allow isolation of the $C_H$1/Cκ heterodimer from the IgG1-Fc region for crystallography applications. (see SEQ ID NO:1) The Wild-Type (no designs) pEHK_Cκ (SEQ ID NO:2) and pEHK_8XHIS_Cκ (SEQ ID NO:3) plasmids are created by recombinase cloning of single gBlocks (IDT) into the pEHK vector using AgeI and EcoRI restriction sites.

The computational and rational design modifications are introduced into the pEHG1_$C_H$1-Fc, pEHK_Cκ, and pEHK_8XHIS_Cκ plasmids in one of two ways. The first procedure employs site directed primer based mutagenesis. Briefly, the site-directed mutagenesis protocol employs a supercoiled double-stranded DNA vector and two synthetic oligonucleotide primers (IDT) containing the desired mutation(s). The oligonucleotide primers, each complementary to opposite strands of the vector, are extended during thermal cycling by DNA polymerase (HotStar HiFidelity Kit, Qiagen Cat. #202602) to generate an entirely new mutated plasmid. Following temperature cycling, the product is treated with Dpn I enzyme (New England BioLabs, Cat #R0176).

The Dpn I enzyme cleaves only methylated parental DNA derived from the parental plasmid which is prepared in *E. coli*. Each newly generated mutant plasmid pool is then transformed into *E. coli* strain TOP 10 competent cells (Life Technologies). The second method employs synthesized dual or single gBlocks (IDT) containing 15 base pair 5' and 3' overlaps to allow recombinase-based cloning into pEHG1_$C_H$1-Fc plasmids using restriction sites AgeI and BamHI or cloning into pEHK_Cκ and/or pEHK_8XHIS_Cκ plasmids digested with AgeI and EcoRI. The recombinase-based cloning is performed using the In-Fusion protocol (Clontech Laboratories, Inc.) to generate the clone. The In-Fusion construct is then transformed into *E. coli* strain TOP 10 competent cells (Life Technologies). Colonies are picked and clonal DNA is produced by miniprepping according to standard procedures (Qiagen MiniPrep), and sequenced in-house. Medium and large scale plasmid purifications are performed according to the instructions within the Plasmid Plus Midiprep Kit (Qiagen Cat. #12965) and Maxiprep Plus Kit (Qiagen Cat. #12965), respectively.

B. Protein Expression in Human Embryonic Kidney Cells (HEK293) or Chinese Hamster Ovary (CHO) Cells.

To test designs for their ability to enable specific assembly of select $C_H$1/Cκ complexes, for each design an 'A' or 'B' $C_H$1-Fc construct (containing the $C_H$1 design sequence) is co-transfected with both 'a' and 'b' Cκ constructs (containing the Cκ design sequences) for mammalian cell expression and soluble protein secretion. Thus, for each design, the 'A' or 'B' $C_H$1-Fc HC protein is exposed to both LC Cκ proteins. Expressed protein is purified from the mammalian cell culture supernatants, reduced, and characterized by gradient reverse phase (RP) HPLC in a two-dimensional chromatography process (described below) to determine whether the designs induce a preference in pairing of the $C_H$1-Fc proteins with one Cκ protein over the other.

Briefly, constructs are expressed transiently either in HEK293 or CHO cells according to protocols previously described in the literature (Lewis, et al. (2014), Nat. Biotechnol., 32; 191-198 and Rajendra et al. (2015), Biotechnology and Bioengineering, 112; 977-986). To screen select designs as described in Example 1, for each design, (i) pEHG1_$C_H$1-Fc (containing 'A' or 'B' side $C_H$1 design sequence), (ii) pEHK Cκ 8XHIS, and (iii) pEHK_Cκ plasmids (all lacking variable domain genes, e.g., "$V_L$ Minus") are all transfected transiently into HEK293F or CHO cells using a 1:1.5:1.5 plasmid ratio, respectively. The "a" side Cκ design sequences (see Tables 1-3) are typically cloned into the pEHK Cκ $V_L$ Minus plasmid, while the "b" side Cκ design sequences are typically cloned into the pEHK Cκ 8XHIS $V_L$ Minus plasmid. Additionally, for each design screened, each pEHG1_$C_H$1-Fc plasmid (containing either an 'A' or 'B' side $C_H$1 design sequence) is also co-transfected with only its design counterpart pEHK Cκ $V_L$ Minus or pEHK Cκ 8XHIS $V_L$ Minus plasmid (using a 1:3 HC/LC ratio) as a control to allow identification of which peak in the reverse phase elution profile (described below) belongs to the Cκ protein versus the 8XHis_Cκ protein. Transfected cells are grown at 37° C. in a 5% $CO_2$ incubator while shaking at 125 rpm for 5 days. Secreted protein is harvested by centrifugation at 2K rpm for 5 min. and recovery of the supernatant.

C. Specificity (Correct Assembly) Screening

The specificity or percent correct assembly of the design pairs may be determined using a two-dimension UPLC (2D UPLC) purification/characterization method (tandem protein G+reverse phase-high pressure liquid chromatography (HPLC) with in-vial reduction) or by liquid chromatography/mass spectrometry (LCMS).

2D UPLC is performed using a Dionex Ultimate 3000 Dual Rapid Separation Liquid Chromatography system. Briefly, the first dimension protein G step purifies the expressed $C_H$1-Fc/Cκ protein dimer using a protein G column (POROS@ G 20 μm Column, 2.1×30 mm, 0.1 mL part #2-1002-00) equilibrated with 1× PBS prior to sample load. All flow rates are 1 mL/min except the final post elution column wash at 2 mL/min. 450 μL samples of filtered cell culture supernatant is injected onto the protein G column. After washing with 1× PBS, the column is eluted with 100 mM sodium phosphate, pH 2.2 (2 minutes). Protein G eluents are collected into vials pre-filled with 20 μL 1 M TCEP (tris(2-carboxyethyl)phosphine) in an auto sampler held at ambient temperature. Titers of expressed $C_H$1-Fc/Cκ protein dimer are determined by comparison to eluent peak areas obtained from a standard curve of an in-house human IgG protein G purification.

The second dimension is for characterization of the relative ratio of each Cκ protein ("a" side designs in Cκ OR "b" side designs in 8XHIS_Cκ, see Tables 1-3) that binds to each $C_H$1-Fc protein. The method utilizes two buffers: Buffer A being 100% $H_2O$ and 0.05% trifluoroacetic acid (TFA); Buffer B being 100% acetonitrile (CAN), 0.05% TFA. All flow rates are 1 mL/min. The method injects each purified and reduced sample onto a Waters Symmetry C18 column, 4.6×75 mm, 3.5 μm (WAT066224) equilibrated in 95% Buffer A/5% Buffer B. Once each sample is captured onto the column, a gradient is applied starting at 10% ACN and linearly going to 40% ACN in 13 minutes. The column is then flushed with up to 70% ACN for 2 minutes and re-equilibrated with 5% ACN for 2 minutes prior to the next injection. The reversed-phase profile typically includes three peaks; one for each of the Cκ and Cκ 8XHIS polypeptides, and one for the $C_H$J-Fc polypeptide. Comparisons by reversed-phase chromatography are made by overlaying the control samples (as described in Step B above) with test samples. The areas under each peak are determined to calculate percent correct assembly of the particular $C_H$1/Cκ design pair.

Alternatively, test articles may be analyzed for specific assembly by LCMS. Briefly, test articles may be purified from supernatants using the UPLC method as described above. However, instead of reducing the samples in TCEP and running the $2^{nd}$ dimension reverse phase column, the samples are submitted for LCMS characterization as generally described previously (See Lewis, et al. (2014), Nat. Biotechnol., 32; 191-198).

D. Thermal Stability Determinations

Enzyme-linked immunosorbent assays (ELISAs) or differential-scanning calorimetry (DSC) assays for the detection of thermo-challenged protein samples may be performed to compare the stability of the designed samples against the Wild-Type control proteins. For ELISAs, briefly, 96-well U-bottom high protein binding 96-well plates (Greiner bio-one, cat #650061) are coated overnight at 4° C. with 100 μL/well with 1 μg/ml of Sheep anti human IgG (Fd) (Meridian Life Science Cat. #W90075C-1) in a 0.05 M NaHCO$_3$ buffer, pH 8.3. The plates are then washed four times with PBS with 0.1% TWEEN® (PBST) and blocked for 1 hour with casein (Thermo Scientific, cat #37528) at 37° C. The plates are washed again and 100 μL/well of culture supernatants containing the "variable minus" $C_H$J-Fc proteins expressed with their cognate "variable minus" Cκ proteins (normalized to be at about 100 μg/ml) are incubated for 1 hr. at 37° C. The supernatants are pre-exposed to various temperatures for 1 hr using a Thermal cycler with a 25° C. thermal gradient window (55° C. to 80° C.). The plates are then washed and Goat-anti-human Kappa-HRP (Southern Biotech Cat. #2060-05) at 1:8000 in casein is added and incubated for 1 hr at room temperature. The plates are then washed and 1 step Ultra TMB ELISA substrate (Thermo Scientific Cat. #34208) is added at 50 μL/well. The reaction is allowed to proceed for 1-15 minutes then quenched by the addition of (50 μL) 2.5M H$_2$SO$_4$. The absorbance at 450 nm is then read using a SPECTRAMAX® 190 UV plate reader (Molecular Devices).

Alternatively, the stability of purified proteins (i.e., WT and design constructs lacking variable domains purified, for example, by FPLC using Protein A) may be characterized using differential scanning calorimetry (DSC), essentially as follows. The midpoints of the thermal unfolding transitions (denoted '$T_m$') of the $C_H$1/Cκ domains provide a measure of their relative stability. DSC is performed using an automated capillary DSC system (capDSC, GE Healthcare). Protein solutions and reference (buffer) solutions are sampled automatically from a 96-well plate using the robotic attachment. Before each protein scan, at least one buffer/buffer scan is performed to define the baseline for subtraction. All 96-well plates containing protein are stored within the instrument at 6° C. Samples are run at 1.0 mg/ml protein concentration in PBS. Scans are performed from 10 to 110° C. at 90° C./hr using the low feedback mode. Scans are analyzed using the Origin software supplied by the manufacturer. Subsequent to the subtraction of reference baseline scans, nonzero protein scan baselines are corrected using a third-order polynomial.

E. Specificity of Assembly and Thermal Stability Characterization Results

Select initial and combination designs in the Cκ/$C_H$1-Fc constructs lacking variable domains are evaluated for specificity of correct assembly as determined by reverse phase HPLC and/or LCMS according to procedures as described above. Results of specific assembly characterizations are provided in the Table 4 below.

TABLE 4

| Design | HC_A $C_H$1 | LC_a $C_κ$ | HC_B $C_H$1 | LC_b $C_κ$ | % Aa | % Ab | % Ba | % Bb |
|---|---|---|---|---|---|---|---|---|
| Initial designs evaluated using reverse phase HPLC$^a$ ||||||||||
| WT | WT | WT | WT | WT | 76.0 ± 6.6 | 23.9 ± 6.7 | 76.6 ± 2.7 | 23.3 ± 2.7 |
| 1.3 | S188G | S176I | WT | WT | 100/95 | 0/2.4 | 91.6/73 | 8.4/25 |
| 1.4 | S188G | S176I | S188T | WT | 100 | 0 | 82.2 | 17.8 |
| 1.5 | S188A | S176M | WT | WT | 96.3 | 3.7 | 92.1 | 7.9 |
| 1.6 | S188A | S176M | S188T | WT | 94.4/87.1 | 5.6/7.4 | 78.3/61.7 | 21.7/27.2 |
| 1.7 | S188G | S176M | WT | WT | 100/100 | 0/0 | 91.9/94 | 8.1 |
| 1.8 | S188G | S176M | S188T | WT | 100/96.7 | 0/0 | 77.7/94.2 | 23.3 |
| 1.12 | S188G | S176I | S188I | S176G | 94 ± 1.5 | 3.8 ± 3.6 | 67.8 ± 6.3 | 30.7 ± 4.1 |
| 1.13 | S188A | S176M | S188M | S176A | 89.4 | 10.6 | 67.8 | 32.2 |
| 1.15 | S188I | S176A | WT | WT | 72.2/68.4 | 27.8 | 0/100 | 0/0 |
| 1.18 | S188G | S176I | S188I | S176A | 98.7 ± 2.3 | 0 ± 0 | 68.2 ± 3.1 | 27.9 ± 5.2 |
| 2.3 | K145A | S131R | WT | WT | 59 ± 5.9 | 41 ± 5.9 | 1.3 ± 2.2 | 96.3 ± 3.7 |
| 2.4 | K145A | S131K | WT | WT | 61.6 | 38.4 | 0 | 100 |
| 2.7 | K145S | S131R | WT | WT | 51.8 | 48.2 | 0 | 100 |
| 2.8 | K145S | S131K | WT | WT | 34.8 | 65.2 | 7.5 | 92.5 |
| 12.1 | K221E | E123K | WT | WT | 100 | 0 | 23.8$^b$ | 76.2$^b$ |
| 12.2 | K221E | E123Q | WT | WT | 69.1 | 30.9 | 68 | 32 |
| Combination designs evaluated using reverse phase HPLC$^a$ ||||||||||
| 1.3.1 | K145A S188A | S131R S176I | WT | WT | 77.7 | 22.3 | 12.5 | 87.5 |
| 1.12.1 | K145A S188A | S131R S176I | S188I | S176G | 72.3 | 27.7 | 36.3 | 63.7 |
| 1.18.1 | K145A S188A | S131R S176I | S188I | S176A | 70.1 | 29.9 | 40 | 60 |
| 14.1.2 | K145A K221E | S131R E123K | WT | WT | 100$^b$ | 0$^b$ | 4.5$^b$ | 95.5$^b$ |

TABLE 4-continued

| Design | HC_A C$_H$1 | LC_a C$_K$ | HC_B C$_H$1 | LC_b C$_K$ | % Aa | % Ab | % Ba | % Bb |
|---|---|---|---|---|---|---|---|---|
| 14.3.1.1 | S188A K145A | S176I S131R | K221E | E123K | 94.7 | 5.3 | 0 | 100 |
| 14.3.1.2 | S188G K145A | S176I S131R | K221E | E123K | 100 | 0 | 0 | 100 |
| 15.1 | K145A K221E S188A | S131R E123K S176I | WT | WT | 97.3 | 2.7 | 5.8 | 94.2 |
| 15.2 | K145A K221E S188G | S131R E123K S176I | WT | WT | 95.7 | 4.3 | 6.1 | 93.9 |
| Combination designs evaluated by LCMS$^c$ | | | | | | | | |
| 14.1.2 | K145A K221E | S131R E123K | WT | WT | 99.8 ± 0.1 | 0.2 ± 0.04 | 0/0 | 100/100 |
| 14.3.1.1 | S188A K145A | S176I S131R | K221E | E123K | 98.2 ± 0.6 | 1.8 ± 0.6 | 0.2 ± 0.2 | 99.8 ± 0.2 |
| 14.3.1.2 | S188G K145A | S176I S131R | K221E | E123K | 99.8 | 0.2 | 0.1 | 99.0 |

$^a$Values are calculated based on area for each C$_K$ species, 'a' or 'b', as observed using denaturing, reverse phase chromatography with protein G purified samples that are reduced prior to injection onto the reverse phase column. Values with error (±) were run 3 or more times. The mean value is listed followed by the standard deviation. Cells with 2 values were run in duplicate and the values listed are from each replicate.
$^b$Peak overlap in the HPLC method made these values difficult to quantify.
$^c$Values are calculated based on the deconvoluted peak areas for each of the species from the LCMS evaluation. Values with error (±) were run 3 or more times. The mean value is listed followed by the standard deviation. Cells with 2 values were run in duplicate and the values listed are from each replicate.

The Wild-Type (WT) 'b' C$_K$ with the 8XHistag expresses slightly poorer than the WT 'a' C$_K$ without the tag resulting in a roughly 75/25 ratio in the absence of any designs (Table 4). Many of the initial designs show modest increases in "Aa" and/or "Bb" assembly but are not considered further due to decreases in expression, likely due to destabilization of the interface. However, certain designs express well and improve the percent of "Aa" and/or "Bb" assembly. These include designs 1.3, 1.18, 2.3, and 12.1. A second round of designs combining the best mutations from the initial screen are generated in the same C$_K$/C$_H$1-Fc constructs. Combining certain designs results in modest increases in specificity of assembly over the initial designs. Many combination designs again result in reduced protein expression and are not considered further. Certain designs, however, result in near complete specificity of pairing with 'A' C$_H$1-Fc assembling with near complete specificity to 'a' C$_K$, and 'B' C$_H$1-Fc assembling with near complete specificity to 'b' C$_K$. These designs include 14.1.2, 14.3.1.1, 14.3.1.2, 15.1, and 15.2 (Table 4). To provide a secondary method for quantitating the assembly of the C$_K$/C$_H$1-Fc proteins, a subset of the designs (14.1.2, 14.3.1.1, and 14.3.1.2) are submitted for LCMS analyses. Based on the mass spectrometry results, each of these designs show near complete specificity of assembly of "Aa" and "Bb" relative to the mis-paired "Ab" and "Ba" species, similar to the data produced using the reverse phase HPLC method (Table 4).

Species of select combination designs in the C$_K$/C$_H$1-Fc constructs lacking variable domains (i.e. "Aa" or "Bb" dimers) are evaluated for thermal stability using DSC according to procedures essentially as described above. Results of thermal stability characterizations are provided in the Table 5 below.

TABLE 5

| C$_H$1-Fc/C$_K$ Heterodimer (WT or Design) | Midpoint of thermal denaturation (T$_m$) in ° C. |
|---|---|
| WT | 71.9 |
| 14.1.2Aa | 70.3 |
| 14.3.1.1Aa | 78.5 |
| 14.3.1.1Bb | 71.1 |
| 15.1Aa | 78.8 |
| 15.2Aa | 77.4 |

The 14.1.2, 14.3.1.1, 15.1, and 15.2 design constructs do not result in reduced stability compared to the wild-type C$_H$1/C$_K$ domains (Table 5). C$_H$1/C$_K$ domains containing either C$_H$1_S188A/C$_K$_S176I or C$_H$1_S188I/C$_K$_S176A are found to be stabilized over WT C$_H$1/C$_K$ based on their midpoints of thermal denaturation (T$_m$) measured using DSC. 14.3.1.1 and 15.1 both contain C$_H$1_S188A/C$_K$_S176I and are significantly more stable than the WT C$_H$1/C$_K$ heterodimer (Table 5). In summary, the data in Table 5 demonstrates that the indicated designs, which each enable specific C$_H$1/C$_K$ assembly, are essentially as stable, or more stable than the WT heterodimer.

Example 3: Bispecific Antibodies

A. Cloning of IgG BsAbs Harboring Novel C$_H$1/C$_K$ Designs Human IgG1 bispecific antibodies containing select C$_H$1/C$_K$ design mutations or WT C$_H$1/C$_K$ are constructed using pEHG1 (HC) and pEHK (LC) vectors, as generally described above. Variable domains from parental mAbs Pertuzumab (Franklin, M. C. et al. (2004), Cancer Cell; 5; 317-328), MetMAb (Merchant, M., et al. (2013), Proc. Nat'l. Acad. Sci. USA; 110; E2987-E2996), Matuzumab (Schmiedel, J., et al. (2008), Cancer Cell; 13; 365-373) and BHA10 (Jordan, J. L., et al. (2009), Proteins; 77; 832-841) are used in preparation of test articles (fully IgG bispecific antibodies). The Pertuzumab and MetMAb parental mAb constructs are chosen as the receptacles for the HC_"A" and LC_"a" design sequences for each of the C$_H$1/C$_K$ designs tested, while the BHA10 and Matuzumab parental mAb constructs are chosen as the receptacles for the HC_"B" and LC_"b" design sequence for each of the $C_H1/C\kappa$ designs tested. Design mutations are introduced using either the site-directed mutagenesis or gBlock recombinase cloning methods, also as described above. Each bispecific antibody is further engineered to contain select $C_H3$ domain design mutations (e.g., Design 7.8.60 as described in Leaver-Fay A., et al. (2016), Structure; 24; 641-651 and WO 2016/118742 (A1)) to improve HC heterodimerization, as well as an N297Q mutation in each HC to reduce N-linked glycosylation. Additionally, select variable domain design mutations (e.g. Designs "AB" or "H4DR", each as described in WO2014/150973) are each separately and individually introduced into one of the $V_H/V_L$ interfacse of each bispecific antibody to evaluate the impact of specificity designs in both the variable and constant domains of the Fabs. Plasmid isolation, sequencing and scale-up are essentially as described above for constructs lacking variable domains B. Protein Expression For IgG bispecific antibody production, four plasmids (two that contain one of the two HC encoding sequences (i.e., HC_"A" or HC_"B") and two that contain one of the two LC encoding sequences (i.e., LC_"a" and LC_"b")) are co-transfected in HEK293F cells (using 1:3 HC:LC plasmid ratios) or CHO cells (using 1:1 HC:LC plasmid ratios). Transfected cells are grown at 37° C. in an 8% $CO_2$ incubator while shaking at 125 rpm for 5 days (HEK293F cells) or 6 days (CHO cells). For both HEK293 and CHO, secreted protein material is harvested by centrifugation at 5 K rpm for 5 min at the end of the culture period. Supernatants are passed through 0.22 μm filters (small scale) for either large or small scale purification.

Table 6 below provides the parental mAb components and Sequence Identification Numbers (SEQ ID NOs.) of the complete HCs and LCs of the fully IgG bispecific antibodies constructed with, and without, select $C_H1/C\kappa$ designs as described herein.

TABLE 6

| $C_H1/C\kappa$ design | HC_A (SEQ ID NO.) | LC_a (SEQ ID NO.) | HC_B (SEQ ID NO.) | LC_b (SEQ ID NO.) |
|---|---|---|---|---|
| MetMab[a] × BHA10[b] | | | | |
| Wild-Type | 4 | 10 | 28 | 30 |
| 14.1.2 | 5 | 11 | 28 | 30 |

TABLE 6-continued

| $C_H1/C\kappa$ design | HC_A (SEQ ID NO.) | LC_a (SEQ ID NO.) | HC_B (SEQ ID NO.) | LC_b (SEQ ID NO.) |
|---|---|---|---|---|
| 14.3.1.1 | 6 | 12 | 29 | 31 |
| 14.3.1.2 | 7 | 12 | 29 | 31 |
| 15.1 | 8 | 13 | 28 | 30 |
| 15.2 | 9 | 13 | 28 | 30 |
| Pertuzumab[a] × BHA10[b] | | | | |
| Wild-Type | 14 | 20 | 28 | 30 |
| 14.1.2 | 15 | 21 | 28 | 30 |
| 14.3.1.1 | 16 | 22 | 29 | 31 |
| 14.3.1.2 | 17 | 22 | 29 | 31 |
| 15.1 | 18 | 23 | 28 | 30 |
| 15.2 | 19 | 23 | 28 | 30 |
| MetMAb[a] × Matuzumab[b] | | | | |
| Wild-Type | 4 | 10 | 24 | 26 |
| 14.1.2 | 5 | 11 | 24 | 26 |
| 14.3.1.1 | 6 | 12 | 25 | 27 |
| 14.3.1.2 | 7 | 12 | 25 | 27 |
| 15.1 | 8 | 13 | 24 | 26 |
| 15.2 | 9 | 13 | 24 | 26 |
| Pertuzumab[a] × Matuzumab[b] | | | | |
| Wild-Type | 14 | 20 | 24 | 26 |
| 14.1.2 | 15 | 21 | 24 | 26 |
| 14.3.1.1 | 16 | 22 | 25 | 27 |
| 14.3.1.2 | 17 | 22 | 25 | 27 |
| 15.1 | 18 | 23 | 24 | 26 |
| 15.2 | 19 | 23 | 24 | 26 |

[a]MetMAb and Pertuzumab HCs and LCs contain the HC_"A" and LC_"a" design sequences for each of the $C_H1/C\kappa$ designs, the AB variable domain designs described previously (WO2014/150973 A1) and 7.8.60A $C_H3$ domain heterodimerization designs also described previously (WO 2016/118742 (A1)).
[b]BHA10 and Matuzumab HCs and LCs contain the HC_"B" and LC_"b" design sequence for each of the $C_H1/C\kappa$ designs, the H4DR variable domain designs described previously (WO2014/150973 A1) and 7.8.60B $C_H3$ domain heterodimerization designs also described previously (WO 2016/118742 (A1)).

C. Specificity (Correct Assembly) Screening of Fully IgG Bispecfic Antibodies

The IgG BsAb HC and LC constructs are generated and expressed as described above. Secreted supernatants are purified using the HPLC protein G method as described above for purifying the $C\kappa/C_H1$-Fc proteins, however, the purified proteins are not reduced and submitted for reverse phase chromatography but rather are collected and submitted for LCMS analysis essentially as described in Lewis et al., 2014 *Nature* Biotechnol; 32; 191-198. Table 7 below provides the percent assembly of the correctly paired BsAb as well as the mis-paired species containing two LC_"a" or two LC_"b" light chains as well as those containing HC_"A"/HC_"A" and HC_"B"/HC_"B" homodimers. All values in the table represent the mean and standard deviation of at least three separate experiments.

TABLE 7

| $C_H1/C\kappa$ design | % BsAb (correct) | % 2x LC_a (mis-pair) | % 2x LC_b (mis-pair) | % HC_A/HC_A (homodimer) | % HC_B/HC_B (homodimer) |
|---|---|---|---|---|---|
| MetMAb[a] × BHA10[b] | | | | | |
| Wild-Type | 91.9 ± 3.8 | 0.8 ± 2.0 | 4.7 ± 4.7 | 1.2 ± 1.3 | 1.5 ± 2.8 |
| 14.1.2 | 95.4 ± 0.4 | 0.0 ± 0.0 | 3.9 ± 0.3 | 0.7 ± 0.7 | 0.0 ± 0.0 |
| 14.3.1.1 | 93.2 ± 1.6 | 0.0 ± 0.0 | 4.6 ± 0.9 | 2.5 ± 0.9 | 0.0 ± 0.0 |
| 14.3.1.2 | 85.6 ± 4.6 | 0.0 ± 0.0 | 7.2 ± 2.3 | 8.4 ± 3.1 | 0.0 ± 0.0 |
| 15.1 | 87.4 ± 2.5 | 2.3 ± 4.0 | 8.3 ± 2.1 | 0.0 ± 0.0 | 1.9 ± 1.7 |
| 15.2 | 91.4 ± 0.5 | 0.0 ± 0.0 | 7.2 ± 0.5 | 1.6 ± 0.1 | 0.0 ± 0.0 |
| Pertuzumab[a] × BHA10[b] | | | | | |
| Wild-Type | 58.9 ± 2.8 | 39.9 ± 2.7 | 0.4 ± 0.4 | 0.0 ± 0.0 | 0.8 ± 0.9 |
| 14.1.2 | 95.9 ± 2.0 | 0.0 ± 0.0 | 0.0 ± 0.0 | 0.0 ± 0.0 | 4.1 ± 2.0 |
| 14.3.1.1 | 88.3 ± 7.5 | 1.0 ± 0.1 | 0.0 ± 0.0 | 9.2 ± 8.0 | 1.7 ± 0.3 |
| 14.3.1.2 | 84.0 ± 1.7 | 0.9 ± 0.3 | 0.0 ± 0.0 | 14.1 ± 0.8 | 1.3 ± 1.2 |

TABLE 7-continued

| $C_H1$/Cκ design | % BsAb (correct) | % 2x LC_a (mis-pair) | % 2x LC_b (mis-pair) | % HC_A/HC_A (homodimer) | % HC_B/HC_B (homodimer) |
|---|---|---|---|---|---|
| 15.1 | 96.8 ± 5.5 | 0.0 ± 0.0 | 0.8 ± 1.4 | 0.8 ± 1.4 | 1.6 ± 2.8 |
| 15.2 | 94.6 ± 3.7 | 0.0 ± 0.0 | 2.1 ± 0.9 | 1.7 ± 2.9 | 1.8 ± 3.1 |
| MetMAb[a] × Matuzumab[b] | | | | | |
| Wild-Type | 91.0 ± 2.6 | 3.2 ± 2.3 | 1.2 ± 1.3 | 1.1 ± 1.2 | 3.7 ± 2.5 |
| 14.1.2 | 94.8 ± 0.3 | 0.0 ± 0.0 | 1.4 ± 0.3 | 2.3 ± 0.3 | 1.7 ± 0.1 |
| 14.3.1.1 | 93.7 ± 0.3 | 0.8 ± 0.1 | 1.4 ± 0.1 | 3.4 ± 0.1 | 0.6 ± 0.3 |
| 14.3.1.2 | 92.6 ± 0.5 | 0.9 ± 0.2 | 1.3 ± 0.2 | 5.4 ± 0.3 | 0.0 ± 0.0 |
| 15.1 | 92.3 ± 2.2 | 0.0 ± 0.0 | 4.3 ± 1.3 | 3.1 ± 1.9 | 0.6 ± 0.7 |
| 15.2 | 96.3 ± 2.6 | 0.0 ± 0.0 | 1.2 ± 0.6 | 0.3 ± 0.5 | 2.2 ± 2.5 |
| Pertuzumab[a] × Matuzumab[b] | | | | | |
| Wild-Type | 70.0 ± 11.0 | 21.6 ± 8.0 | 0.0 ± 0.0 | 0.0 ± 0.0 | 8.5 ± 4.0 |
| 14.1.2 | 97.3 ± 2.0 | 0.0 ± 0.0 | 0.0 ± 0.0 | 0.1 ± 0.2 | 2.6 ± 1.9 |
| 14.3.1.1 | 96.3 ± 1.5 | 0.0 ± 0.0 | 0.0 ± 0.0 | 2.6 ± 0.6 | 1.1 ± 1.0 |
| 14.3.1.2 | 96.2 ± 0.9 | 0.0 ± 0.0 | 0.2 ± 0.3 | 3.7 ± 1.2 | 0.0 ± 0.0 |
| 15.1 | 99.5 ± 0.9 | 0.0 ± 0.0 | 0.0 ± 0.0 | 0.5 ± 0.9 | 0.0 ± 0.0 |
| 15.2 | 99.1 ± 0.1 | 0.0 ± 0.0 | 0.0 ± 0.0 | 1.0 ± 0.1 | 0.0 ± 0.0 |

[a]MetMAb and Pertuzumab HCs and LCs contain the HC_"A" and LC_"a" design sequences for each of the $C_H1$/Cκ designs, the AB variable domain designs described previously (WO2014/150973 A1) and 7.8.60A $C_H3$ domain heterodimerization designs also described previously (WO 2016/118742 (A1)).
[b]BHA10 and Matuzumab HCs and LCs contain the HC_"B" and LC_"b" design sequence for each of the $C_H1$/Cκ designs, the H4DR variable domain designs described previously (WO2014/150973 A1) and 7.8.60B $C_H3$ domain heterodimerization designs also described previously (WO 2016/118742 (A1)).

The data in Table 7 indicates that all of the indicated designs resulted in >80% correctly paired BsAb assembly for each of the constructs prepared. Further, for the Pertuzumab component-containing constructs, all of the tested $C_H1$/Cκ designs displayed large and significant increases in percent correct assembly of BsAb compared to their WT $C_H1$/Cκ domain counterparts. (Table 7).

D. Bispecific Antibody Binding Activity Assay

The dual-binding activity of the same synthesized IgG BsAbs is assessed using a sandwich ELISA. Two Sandwich ELISAs are developed for detecting the four different BsAb test articles; one for detecting anti-HER-2/anti-EGFR BsAb activity, one for detecting anti-HER-2/anti-LTβR BsAb activity, one for detecting anti-cMET/anti-EGFR BsAb activity and one for detecting anti-cMET/anti-LTβR BsAb activity. For all ELISAs, clear 96-well round bottom high binding Immulon microtiter plates (Greiner bio-one, cat #650061) are coated overnight at 2-8° C. with 50 µL/well 1 µg/mL hHER-2-Fc or 1 µg/mL hHGFR(cMet)-Fc (both from R&D systems) in a 50 mM Na2CO3 pH 8.3 buffer. The plates are washed 4 times with PBST and blocked with 200 µL/well casein buffer (Pierce) for 1 hr at room temperature. The plates are then washed 4 times with PBST and the parental IgG controls or BsAb IgG test articles are added at 50 µL/well and 5 µg/mL and serially diluted 1:3 down the plate. The controls and test articles are incubated on the plate for 1 hr at room temperature. The plates are then washed 4 times with PBST and 50 µL/well 1 µg/mL hEGFR-Fc-biotin or hLTβR-Fc-biotin (both from R&D systems) is added for 1 hr at room temperature. The plates are then washed 4 times with PBST followed by the addition of a 50 µL/well streptavidin-AP (Jackson Immunoresearch Labs Cat. #016-050-084) diluted 1:1000 in casein buffer. The streptavidin-AP is incubated in each well for 1 hr at room temperature. The plates are then washed 4 times with PBST and 100 L/well 1-step PNPP substrate is added (Thermo Scientific Cat. #37621). After approximately 5-15 minutes, plates are read for Absorbance (405 nm) using a SPECTRAMAX® UV plate reader (Molecular Devices). Biotin-labeling of the hEGFR-Fc and hLTβR-Fc proteins is performed using EZ-LINK™ Sulfo-NHS-LC-Biotin (Thermo Scientific Cat. #21327) according to the manufacturer's protocol. The BsAb titrations are fit to yield $EC_{50}$ values that are listed in Table 8 below.

TABLE 8

| $C_H1$/Cκ design | Dual Antigen Binding EC50 (µg/mL) |
|---|---|
| MetMAb[a] × BHA10[b] | |
| Wild-Type | 0.05 |
| 14.1.2 | 0.05 |
| 14.3.1.1 | 0.070 |
| 14.3.1.2 | 0.11 |
| 15.1 | n.d. |
| 15.2 | n.d. |
| Pertuzumab[a] × BHA10[b] | |
| Wild-Type | 0.06 |
| 14.1.2 | 0.03 |
| 14.3.1.1 | 0.04 |
| 14.3.1.2 | 0.04 |
| 15.1 | n.d. |
| 15.2 | n.d. |
| MetMAb[a] × Matuzumab[b] | |
| Wild-Type | 0.12 |
| 14.1.2 | 0.10 |
| 14.3.1.1 | 0.20 |
| 14.3.1.2 | 0.25 |
| 15.1 | n.d. |
| 15.2 | n.d. |
| Pertuzumab[a] × Matuzumab[b] | |
| Wild-Type | 0.17 |
| 14.1.2 | 0.19 |
| 14.3.1.1 | 0.15 |
| 14.3.1.2 | 0.10 |
| 15.1 | n.d. |
| 15.2 | n.d. |

[a]MetMAb and Pertuzumab HCs and LCs contain the HC_"A" and LC_"a" design sequences for each of the $C_H1$/Cκ designs, the AB variable domain designs described previously (WO2014/150973 A1) and 7.8.60A $C_H3$ domain heterodimerization designs also described previously (WO 2016/118742 (A1)).
[b]BHA10 and Matuzumab HCs and LCs contain the HC_"B" and LC_"b" design sequence for each of the $C_H1$/Cκ designs, the H4DR variable domain designs described previously (WO2014/150973 A1) and 7.8.60B $C_H3$ domain heterodimerization designs also described previously (WO 2016/118742 (A1)).

All of the IgG BsAbs proteins showed strong bispecific binding activity towards their target antigens, but not towards the mis-matched antigen sandwich pairs. Some of the EC$_{50}$s for the BsAbs are lower than what is observed for others (Table 8). This seems to track closely with the level of half-antibody (non-covalently bound single HC/LC species) generation that occurs when one HC/LC pair expresses at a higher level than than the other HC/LC pair in solution.

E. Fully Igg Bispecfic Antibodies without Variable Domain Designs.

To assess the impact of the C$_H$1/Cκ designs to improve IgG BsAb assembly in the absence of variable domain designs (e.g., Design "AB" and "H4DR" as described in WO2014/150973 A1), fully IgG BsAbs are constructed incorporating a subset of the C$_H$1/Cκ designs described herein (i.e., Designs 14.1.2, 14.3.1.1, and 14.3.1.2). In addition to the C$_H$1/Cκ designs, each of the constructs also contains C$_H$3 domain design mutations to improve HC heterodimerization (i.e., Design 7.8.60 as described in Leaver-Fay et al (2016) and WO 2016/118742 A1), as well as an N297Q mutation in each HC to reduce N-linked glycosylation. Cloning, expression, and purification of the test articles is performed essentially as described above. Also as described above, the Pertuzumab and MetMAb parental mAb constructs are chosen as the receptacles for the HC_"A" and LC_"a" design sequences for each of the C$_H$1/Cκ designs tested, while the BHA10 and Matuzumab parental mAb constructs are chosen as the receptacles for the HC_"B" and LC_"b" design sequence for each of the C$_H$1/Cκ designs tested.

Table 9 below provides the parental mAb components and Sequence Identification Numbers (SEQ ID NOs.) of the complete HCs and LCs of the fully IgG bispecific antibodies constructed with, and without, select C$_H$1/Cκ designs as described herein (but without any variable domain designs).

TABLE 9

| C$_H$1/Cκ design | HC_A (SEQ ID NO.) | LC_a (SEQ ID NO.) | HC_B (SEQ ID NO.) | LC_b (SEQ ID NO.) |
| --- | --- | --- | --- | --- |
| MetMAb × BHA10 | | | | |
| Wild-Type | 32 | 36 | 50 | 52 |
| 14.1.2 | 33 | 37 | 50 | 52 |
| 14.3.1.1 | 34 | 38 | 51 | 53 |
| 14.3.1.2 | 35 | 38 | 51 | 53 |
| Pertuzumab × BHA10 | | | | |
| Wild-Type | 39 | 43 | 50 | 52 |
| 14.1.2 | 40 | 44 | 50 | 52 |
| 14.3.1.1 | 41 | 45 | 51 | 53 |
| 14.3.1.2 | 42 | 45 | 51 | 53 |
| MetMAb × Matuzumab | | | | |
| Wild-Type | 32 | 36 | 46 | 48 |
| 14.1.2 | 33 | 37 | 46 | 48 |
| 14.3.1.1 | 34 | 38 | 47 | 49 |
| 14.3.1.2 | 35 | 38 | 47 | 49 |
| Pertuzumab × Matuzumab | | | | |
| Wild-Type | 39 | 43 | 46 | 48 |
| 14.1.2 | 40 | 44 | 46 | 48 |
| 14.3.1.1 | 41 | 45 | 47 | 49 |
| 14.3.1.2 | 42 | 45 | 47 | 49 |

The fully IgG BsAbs containing the C$_H$1/Cκ Designs 14.1.2, 14.3.1.1, and 14.3.1.2 and the CH3 Design 7.8.60 (but lacking variable domain designs) are similarly characterized for specificity of assembly using LCMS as described above and in Lewis et al., 2014 Nature Biotechnol. 32: 191-198. Table 10 below provides the percent assembly of the correctly paired BsAb as well and the mis-paired species containing two LC_"a" or two LC_"b" light chains as well as those containing HC_"A"/HC_"A" and HC_"B"/HC_"B" homodimers. All values in the table represent the mean and standard deviation of at least three separate experiments.

TABLE 10

| C$_H$1/Cκ design | % BsAb (correct) | % 2x LC_a (mis-pair) | % 2x LC_b (mis-pair) | % HC_A/HC_A (homodimer) | % HC_B/HC_B (homodimer) |
| --- | --- | --- | --- | --- | --- |
| MetMAb[a] × BHA10[b] | | | | | |
| Wild-Type | 61.0 ± 1.0 | 14.6 ± 1.2 | 24.4 ± 0.4 | 0.0 ± 0.0 | 0.0 ± 0.0 |
| 14.1.2 | 71.9 ± 2.1 | 2.7 ± 0.5 | 25.4 ± 1.8 | 0.0 ± 0.0 | 0.0 ± 0.0 |
| 14.3.1.1 | 65.5 ± 1.2 | 2.7 ± 0.1 | 31.8 ± 1.2 | 0.0 ± 0.0 | 0.0 ± 0.0 |
| 14.3.1.2 | 68.5 ± 2.3 | 2.8 ± 1.0 | 28.8 ± 1.5 | 0.0 ± 0.0 | 0.0 ± 0.0 |
| Pertuzumab[a] × BHA10[b] | | | | | |
| Wild-Type | 59.0 ± 5.3 | 33.9 ± 7.8 | 7.1 ± 2.6 | 0.0 ± 0.0 | 0.0 ± 0.0 |
| 14.1.2 | 57.5 ± 1.7 | 36.0 ± 1.8 | 6.5 ± 0.4 | 0.0 ± 0.0 | 0.0 ± 0.0 |
| 14.3.1.1 | 68.2 ± 0.3 | 28.3 ± 0.2 | 3.6 ± 0.2 | 0.0 ± 0.0 | 0.0 ± 0.0 |
| 14.3.1.2 | 71.3 ± 2.6 | 26.9 ± 1.3 | 1.8 ± 1.5 | 0.0 ± 0.0 | 0.0 ± 0.0 |
| MetMab[a] × Matuzumab[b] | | | | | |
| Wild-Type | 78.6 ± 0.5 | 12.3 ± 0.7 | 9.0 ± 0.9 | 0.0 ± 0.0 | 0.3 ± 0.3 |
| 14.1.2 | 92.3 ± 0.4 | 1.5 ± 0.4 | 5.6 ± 0.2 | 0.0 ± 0.0 | 0.5 ± 0.2 |
| 14.3.1.1 | 80.7 ± 2.2 | 0.0 ± 0.0 | 19.1 ± 2.3 | 0.0 ± 0.0 | 0.0 ± 0.0 |
| 14.3.1.2 | n.d.[c] | n.d.[c] | n.d.[c] | n.d.[c] | n.d.[c] |

TABLE 10-continued

| $C_H1$/Cκ design | % BsAb (correct) | % 2x LC_a (mis-pair) | % 2x LC_b (mis-pair) | % HC_A/HC_A (homodimer) | % HC_B/HC_B (homodimer) |
|---|---|---|---|---|---|
| Pertuzumab[a] × Matuzumab[b] | | | | | |
| Wild-Type | 64.1 ± 5.1 | 29.1 ± 7.2 | 5.1 ± 1.8 | 2.9 ± 0.5 | 0.0 ± 0.0 |
| 14.1.2 | 81.3 ± 0.8 | 18.1 ± 1.7 | 0.0 ± 0.0 | 0.7 ± 1.2 | 0.0 ± 0.0 |
| 14.3.1.1 | 80.0 ± 2.0 | 11.5 ± 0.5 | 8.5 ± 2.3 | 0.0 ± 0.0 | 0.0 ± 0.0 |
| 14.3.1.2 | 78.6 ± 1.0 | 12.4 ± 0.2 | 9.0 ± 1.2 | 0.0 ± 0.0 | 0.0 ± 0.0 |

[a]MetMAb and Pertuzumab HCs and LCs contain the HC_"A" and LC_"a" design sequences for each of the $C_H1$/Cκ designs, and 7.8.60A $C_H3$ domain heterodimerization designs also described previously (WO 2016/118742 (A1)).
[b]BHA10 and Matuzumab HCs and LCs contain the HC_"B" and LC_"b" design sequence for each of the $C_H1$/Cκ designs and 7.8.60B $C_H3$ domain heterodimerization designs also described previously (WO 2016/118742 (A1)).
n.d. = not done.

The data in Table 10 indicates that the $C_H1$/Cκ domains generally improve correct HC/LC pairing within fully IgG BsAb even in the absence of variable domain designs in the Fab regions. In the majority of cases, incorporating the $C_H1$/Cκ designs alone in the Fab improves correct HC/LC pairing, though some increases are small and the percent correct assembly levels for the full IgG BsAb do not generally achieve the levels observed when the variable domain designs are also included in the Fab regions.

```
                                                         Sequences
SEQ ID. NO. 1. pEHG1_C_H1-Fc
ASTKGPSVFPLAPSSKSTSGGTAALGCLVKDYFPEPVTVSWNSGALTSGVHTFPAVLQSSGLYSLSSVVTVPSSSLGTQTYIC
NVNHKPSNTKVDKKVEPKSCDKGSIEGRGSTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCSVMHEALHNHYTQKSL
SLSPG SEQ ID. NO. 2. pEHK_Cκ
RTVAAPSVFIFPPSDEQLKSGTASVVCLLNNFYPREAKVQWKVDNALQSGNSQESVTEQDSKDSTYSLSSTLTLSKADYEKHK
VYACEVTHQGLSSPVTKSFNRGEC SEQ ID. NO. 3. pEHK_8XHIS_Cκ
HHHHHHHHGGGGSTGRTVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC SEQ. ID. NO. 4. MetMAb VH AB, CH1 WT, N297Q, 7.8.60A
EVQLVESGGGLVQPGGSLRLSCAASGYTFTSYWLHWVRKAPGKGLEWVGMIDPSNSDTRFNPEFKDRFTISADTSKNTAYLQM
NSLRAEDTAVYYCATYRSYVTPLDYWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 5. MetMAb VH AB, CH1 14.1.2 (K145A K221E), N297Q, 7.8.60A
EVQLVESGGGLVQPGGSLRLSCAASGYTFTSYWLHWVRKAPGKGLEWVGMIDPSNSDTRFNPEFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLSSVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 6. MetMAb VH AB, CH1 14.3.1.1A (K145A S188A), N297Q, 7.8.60A
EVQLVESGGGLVQPGGSLRLSCAASGYTFTSYWLHWVRKAPGKGLEWVGMIDPSNSDTRFNPEFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLASVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 7. MetMAb VH AB, CH1 14.3.1.2A (K145A S188G), N297Q, 7.8.60A
EVQLVESGGGLVQPGGSLRLSCAASGYTFTSYWLHWVRKAPGKGLEWVGMIDPSNSDTRFNPEFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLGSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 8. MetMAb VH AB, CH1 15.1 (K145A S188A K221E), N297Q, 7.8.60A
EVQLVESGGGLVQPGGSLRLSCAASGYTFTSYWLHWVRKAPGKGLEWVGMIDPSNSDTRFNPEFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLASVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG
```

| Sequences |
| --- |

SEQ. ID. NO. 9. MetMAb VH AB, CH1 15.2 (K145A S188G K221E), N297Q, 7.8.60A
EVQLVESGGGLVQPGGSLRLSCAASGYTFTSYWLHWVRKAPGKGLEWVGMIDPSNSDTRFNPEFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLGSVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG

SEQ. ID. NO. 10. MetMAb VL AB, CK WT
RIQMTQSPSSLSASVGDRVTITCKSSQSLLYTSSQKNYLAWYQDKPGKAPKLLIYWASTRESGVPSRFSGSGSGTDFTLTISS
LQPEDFATYYCQQYYAYPWTFGQGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC

SEQ. ID. NO. 11. MetMAb VL AB, CK 14.1.2 (E123K S131R)
RIQMTQSPSSLSASVGDRVTITCKSSQSLLYTSSQKNYLAWYQDKPGKAPKLLIYWASTRESGVPSRFSGSGSGTDFTLTISS
LQPEDFATYYCQQYYAYPWTFGQGTKVEIKRTVAAPSVFIFPPSDKQLKSGTARVVCLLNNFYPREAKVQWKVDNALQSGNSQ
ESVTEQDSKDSTYSLSSTLTLSKADYEKHKVYACEVTHQGLSSPVTKSFNRGEC

SEQ. ID. NO. 12. MetMAb VL AB, CK 14.3.1.1A and 14.3.1.2A (S131R S176I)
RIQMTQSPSSLSASVGDRVTITCKSSQSLLYTSSQKNYLAWYQDKPGKAPKLLIYWASTRESGVPSRFSGSGSGTDFTLTISS
LQPEDFATYYCQQYYAYPWTFGQGTKVEIKRTVAAPSVFIFPPSDEQLKSGTARVVCLLNNFYPREAKVQWKVDNALQSGNSQ
ESVTEQDSKDSTYSLISTLTLSKADYEKHKVYACEVTHQGLSSPVTKSFNRGEC SEQ. ID. NO. 13. MetMAb VL AB, CK 15.1 and 15.2 (E123K S131R S176I)
RIQMTQSPSSLSASVGDRVTITCKSSQSLLYTSSQKNYLAWYQDKPGKAPKLLIYWASTRESGVPSRFSGSGSGTDFTLTISS
LQPEDFATYYCQQYYAYPWTFGQGTKVEIKRTVAAPSVFIFPPSDKQLKSGTARVVCLLNNFYPREAKVQWKVDNALQSGNSQ
ESVTEQDSKDSTYSLISTLTLSKADYEKHKVYACEVTHQGLSSPVTKSFNRGEC SEQ. ID. NO. 14. Pertuzumab VH AB, CH1 WT, N297Q, 7.8.60A
EVQLVESGGGLVQPGGSLRLSCAASGFTFTDYTMDWVRKAPGKGLEWVADVNPNSGGSIYNQEFKGRFTLSVDRSKNTLYLQM
NSLRAEDTAVYYCARNLGPSFYFDYWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 15. Pertuzumab VH AB, CH1 14.1.2 (K145A K221E), N297Q, 7.8.60A
EVQLVESGGGLVQPGGSLRLSCAASGFTFTDYTMDWVRKAPGKGLEWVADVNPNSGGSIYNQEFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLSSVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 16. Pertuzumab VH AB, CH1 14.3.1.1A (K145A S188A), N297Q, 7.8.60A
EVQLVESGGGLVQPGGSLRLSCAASGFTFTDYTMDWVRKAPGKGLEWVADVNPNSGGSIYNQEFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLASVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 17. Pertuzumab VH AB, CH1 14.3.1.2A (K145A S188G), N297Q, 7.8.60A
EVQLVESGGGLVQPGGSLRLSCAASGFTFTDYTMDWVRKAPGKGLEWVADVNPNSGGSIYNQEFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLGSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 18. Pertuzumab VH AB, CH1 15.1 (K145A S188A K221E), N297Q, 7.8.60A
EVQLVESGGGLVQPGGSLRLSCAASGFTFTDYTMDWVRKAPGKGLEWVADVNPNSGGSIYNQEFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLASVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 19. Pertutumab VH AB, CH1 15.2 (K145A S188G K221E), N297Q, 7.8.60A
EVQLVESGGGLVQPGGSLRLSCAASGFTFTDYTMDWVRKAPGKGLEWVADVNPNSGGSIYNQEFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLGSVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG

| Sequences |
| --- |

SEQ. ID. NO. 20. Pertuzumab VL AB, CK WT
RIQMTQSPSSLSASVGDRVTITCKASQDVSIGVAWYQDKPGKAPKLLIYSASYRYTGVPSRFSGSGSGTDFTLTISSLQPEDF
ATYYCQQYYIYPYTFGQGTKVEIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ. ID. NO. 21. Pertuzumab VL AB, CK 14.1.2 (E123K S131R)
RIQMTQSPSSLSASVGDRVTITCKASQDVSIGVAWYQDKPGKAPKLLIYSASYRYTGVPSRFSGSGSGTDFTLTISSLQPEDF
ATYYCQQYYIYPYTFGQGTKVEIKRTVAAPSVFIFPPSDKQLKSGTARVVCLLNNFYPREAKVQWKVDNALQSGNSQESVTEQ
DSKDSTYSLSSTLTLSKADYEKHKVYACEVTHQGLSSPVTKSFNRGEC SEQ. ID. NO. 22. Pertuzumab VL AB, CK 14.3.1.1A and 14.3.1.2A (S131R S176I)
RIQMTQSPSSLSASVGDRVTITCKASQDVSIGVAWYQDKPGKAPKLLIYSASYRYTGVPSRFSGSGSGTDFTLTISSLQPEDF
ATYYCQQYYIYPYTFGQGTKVEIKRTVAAPSVFIFPPSDEQLKSGTARVVCLLNNFYPREAKVQWKVDNALQSGNSQESVTEQ
DSKDSTYSLISTLTLSKADYEKHKVYACEVTHQGLSSPVTKSFNRGEC SEQ. ID. NO. 23. Pertuzumab VL AB, CK 15.1 and 15.2 (E123K S131R S176I)
RIQMTQSPSSLSASVGDRVTITCKASQDVSIGVAWYQDKPGKAPKLLIYSASYRYTGVPSRFSGSGSGTDFTLTISSLQPEDF
ATYYCQQYYIYPYTFGQGTKVEIKRTVAAPSVFIFPPSDKQLKSGTARVVCLLNNFYPREAKVQWKVDNALQSGNSQESVTEQ
DSKDSTYSLISTLTLSKADYEKHKVYACEVTHQGLSSPVTKSFNRGEC SEQ. ID. NO. 24. Matuzumab VH H4DR, CH1 WT, N297Q, 7.8.60B
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYQSTYRVVSVLTVLHQDWLNGKEYKCKVSNKAL
PAPIEKTISKAKGQPRRPRVYTLPPSREEMTKNQVSLVCLVKGFYPSDIAVEWESNGQPENNYKTTPPVLDSDGSFFLYSVLT
VDKSRWQQGNVFSCSVMHEALHNHYTQKSLSLSPG SEQ. ID. NO. 25. Matuzumab VH H4DR, CH1 14.3.1.1B and 14.3.1.2B (K221E), N297Q, 7.8.60B
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDEKVEPKSCDKTHTCPPCPAPELLGGPSVFLFPP
KPKDTLMISRTPEVTCVVVDVSHEDPEVKFNWYVDGVEVHNAKTKPREEQYQSTYRVVSVLTVLHQDWLNGKEYKCKVSNKAL
PAPIEKTISKAKGQPRRPRVYTLPPSREEMTKNQVSLVCLVKGFYPSDIAVEWESNGQPENNYKTTPPVLDSDGSFFLYSVLT
VDKSRWQQGNVFSCSVMHEALHNHYTQKSLSLSPG SEQ. ID. NO. 26. Matuzumab VL H4DR, CK WT
DIQMTQSPSSLSASVGDRVTITCSASSSVTYMYWYQRKPGDAPKLLIYDTSNLASGVPSRFSGSGSGTDYTFTISSLQPEDIA
TYYCQQWSSHIFTFGQGTKVEIKRTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC SEQ. ID. NO. 27. Matuzumab VL H4DR, CK 14.3.1.1B and 14.3.1.2B (E123K)
DIQMTQSPSSLSASVGDRVTITCSASSSVTYMYWYQRKPGDAPKLLIYDTSNLASGVPSRFSGSGSGTDYTFTISSLQPEDIA
TYYCQQWSSHIFTFGQGTKVEIKRTVAAPSVFIFPPSDKQLKSGTASVVCLLNNFYPREAKVQWKVDNALQSGNSQESVTEQD
SKDSTYSLSSTLTLSKADYEKHKVYACEVTHQGLSSPVTKSFNRGEC SEQ. ID. NO. 28. BHA10 VH H4DR, CH1 WT, N297Q, 7.8.60B
QVQLVQSGAEVKKPGSSVKVSCKASGYTFTTYYLHWVRYAPGQGLEWMGWIYPGNVHAQYNEKFKGRVTITADKSTSTAYMEL
SSLRSEDTAVYYCARSWEGFPYWGRGTTVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYQSTYRVVSVLTVLHQDWLNGKEYKCKVSNKALPAPIE
KTISKAKGQPRRPRVYTLPPSREEMTKNQVSLVCLVKGFYPSDIAVEWESNGQPENNYKTTPPVLDSDGSFFLYSVLTVDKSR
WQQGNVFSCSVMHEALHNHYTQKSLSLSPG SEQ. ID. NO. 29. BHA10 VH H4DR, CH1 14.3.1.1B and 14.3.1.2B (K221E), N297Q, 7.8.60B
QVQLVQSGAEVKKPGSSVKVSCKASGYTFTTYYLHWVRYAPGQGLEWMGWIYPGNVHAQYNEKFKGRVTITADKSTSTAYMEL
SSLRSEDTAVYYCARSWEGFPYWGRGTTVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDEKVEPKSCDKTHTCPPCPAPELLGGPSVFLFPPKPKDT
LMISRTPEVTCVVVDVSHEDPEVKFNWYVDGVEVHNAKTKPREEQYQSTYRVVSVLTVLHQDWLNGKEYKCKVSNKALPAPIE
KTISKAKGQPRRPRVYTLPPSREEMTKNQVSLVCLVKGFYPSDIAVEWESNGQPENNYKTTPPVLDSDGSFFLYSVLTVDKSR
WQQGNVFSCSVMHEALHNHYTQKSLSLSPG SEQ. ID. NO. 30. BHA10 VL H4DR, CK WT
DIQMTQSPSSLSASVGDRVTITCKASQNVGINVAWYQRKPGDAPKSLISSASYRYSGVPSRFSGSGSGTDFTLTISSLQPEDF
ATYFCQQYDTYPFTFGQGTKVEIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ. ID. NO. 31. BHA10 VL H4DR, CK 14.3.1.1B and 14.3.1.2B (E123K)
DIQMTQSPSSLSASVGDRVTITCKASQNVGINVAWYQRKPGDAPKSLISSASYRYSGVPSRFSGSGSGTDFTLTISSLQPEDF
ATYFCQQYDTYPFTFGQGTKVEIKRTVAAPSVFIFPPSDKQLKSGTASVVCLLNNFYPREAKVQWKVDNALQSGNSQESVTEQ
DSKDSTYSLSSTLTLSKADYEKHKVYACEVTHQGLSSPVTKSFNRGEC -continued

| Sequences |
|---|

SEQ. ID. NO. 32. MetMAb VH WT, CH1 WT, N297Q, 7.8.60A
EVQLVESGGGLVQPGGSLRLSCAASGYTFTSYWLHWVRQAPGKGLEWVGMIDPSNSDTRFNPNFKDRFTISADTSKNTAYLQM
NSLRAEDTAVYYCATYRSYVTPLDYWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG

SEQ. ID. NO. 33. MetMAb VH WT, CH1 14.1.2 (K145A K221E), N297Q, 7.8.60A
EVQLVESGGGLVQPGGSLRLSCAASGYTFTSYWLHWVRQAPGKGLEWVGMIDPSNSDTRFNPNFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLSSVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG

SEQ. ID. NO. 34. MetMAb VH WT, CH1 14.3.1.1A (K145A S188A), N297Q, 7.8.60A
EVQLVESGGGLVQPGGSLRLSCAASGYTFTSYWLHWVRQAPGKGLEWVGMIDPSNSDTRFNPNFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLASVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG

SEQ. ID. NO. 35. MetMAb VH WT, CH1 14.3.1.2A (K145A S188G), N297Q, 7.8.60A
EVQLVESGGGLVQPGGSLRLSCAASGYTFTSYWLHWVRQAPGKGLEWVGMIDPSNSDTRFNPNFKDRFTISADTSKNTAYLQM
NSLRAEDTAVYYCATYRSYVTPLDYWGQGTLVTVSSASTKGPSVFPLAPSSKSTSGGTAALGCLVADYFPEPVTVSWNSGALT
SGVHTFPAVLQSSGLYSLGSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG

SEQ. ID. NO. 36. MetMAb VL WT, CK WT
DIQMTQSPSSLSASVGDRVTITCKSSQSLLYTSSQKNYLAWYQQKPGKAPKLLIYWASTRESGVPSRFSGSGSGTDFTLTISS
LQPEDFATYYCQQYYAYPWTFGQGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC

SEQ. ID. NO. 37. MetMAb VL WT, CK 14.1.2 (E123K S131R)
DIQMTQSPSSLSASVGDRVTITCKSSQSLLYTSSQKNYLAWYQQKPGKAPKLLIYWASTRESGVPSRFSGSGSGTDFTLTISS
LQPEDFATYYCQQYYAYPWTFGQGTKVEIKRTVAAPSVFIFPPSDKQLKSGTARVVCLLNNFYPREAKVQWKVDNALQSGNSQ
ESVTEQDSKDSTYSLSSTLTLSKADYEKHKVYACEVTHQGLSSPVTKSFNRGEC

SEQ. ID. NO. 38. MetMAb VL WT, CK 14.3.1.1A and 14.3.1.2B (S131R S176I)
DIQMTQSPSSLSASVGDRVTITCKSSQSLLYTSSQKNYLAWYQQKPGKAPKLLIYWASTRESGVPSRFSGSGSGTDFTLTISS
LQPEDFATYYCQQYYAYPWTFGQGTKVEIKRTVAAPSVFIFPPSDEQLKSGTARVVCLLNNFYPREAKVQWKVDNALQSGNSQ
ESVTEQDSKDSTYSLISTLTLSKADYEKHKVYACEVTHQGLSSPVTKSFNRGEC SEQ. ID. NO. 39. Pertuzumab VH, CH1 WT, N297Q, 7.8.60A
EVQLVESGGGLVQPGGSLRLSCAASGFTFTDYTMDWVRQAPGKGLEWVADVNPNSGGSIYNQRFKGRFTLSVDRSKNTLYLQM
NSLRAEDTAVYYCARNLGPSFYFDYWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 40. Pertuzumab VH WT, CH1 14.1.2 (K145A K221E), N297Q, 7.8.60A
EVQLVESGGGLVQPGGSLRLSCAASGFTFTDYTMDWVRQAPGKGLEWVADVNPNSGGSIYNQRFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLSSVVTVPSSSLGTQTYICNVNHKPSNTKVDEKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 41. Pertuzumab VH WT, CH1 14.3.1.1A (K145A S188A), N297Q, 7.8.60A
EVQLVESGGGLVQPGGSLRLSCAASGFTFTDYTMDWVRQAPGKGLEWVADVNPNSGGSIYNQRFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLASVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG -continued

| Sequences |
|---|

SEQ. ID. NO. 42. Pertuzumab VH WT, CH1 14.3.1.2A (K145A S188G), N297Q, 7.8.60A
EVQLVESGGGLVQPGGSLRLSCAASGFTFTDYTMDWVRQAPGKGLEWVADVNPNSGGSIYNQRFKGRFTLSVDRSKNTLYLQM
NSLRAEDTAVYYCARNLGPSFYFDYWGQGTLVTVSSASTKGPSVFPLAPSSKSTSGGTAALGCLVADYFPEPVTVSWNSGALT
SGVHTFPAVLQSSGLYSLGSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQSTYRVVSVLTVLHQDWLNGKEYKCKVSNKALPA
PIEKTISKAKGQPREPQVYTLPPSREEMTDNQVSLTCLVKGFYPSDIAVEWESNGQPENNYKTTPPVLMSDGSFFLASKLTVD
KSRWQQGNVFSCSVMHEALHNHYTQKSLSLSPG SEQ. ID. NO. 43. Pertuzumab VL WT, CK WT
DIQMTQSPSSLSASVGDRVTITCKASQDVSIGVAWYQQKPGKAPKLLIYSASYRYTGVPSRFSGSGSGTDFTLTISSLQPEDF
ATYYCQQYYIYPYTFGQGTKVEIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ. ID. NO. 44. Pertuzumab VL WT, CK 14.1.2 (E123K S131R)
DIQMTQSPSSLSASVGDRVTITCKASQDVSIGVAWYQQKPGKAPKLLIYSASYRYTGVPSRFSGSGSGTDFTLTISSLQPEDF
ATYYCQQYYIYPYTFGQGTKVEIKRTVAAPSVFIFPPSDKQLKSGTARVVCLLNNFYPREAKVQWKVDNALQSGNSQESVTEQ
DSKDSTYSLSSTLTLSKADYEKHKVYACEVTHQGLSSPVTKSFNRGEC SEQ. ID. NO. 45. Pertuzumab VL WT, CK 14.3.1.1A and 14.3.1.2A (S131R S176I)
DIQMTQSPSSLSASVGDRVTITCKASQDVSIGVAWYQQKPGKAPKLLIYSASYRYTGVPSRFSGSGSGTDFTLTISSLQPEDF
ATYYCQQYYIYPYTFGQGTKVEIKRTVAAPSVFIFPPSDEQLKSGTARVVCLLNNFYPREAKVQWKVDNALQSGNSQESVTEQ
DSKDSTYSLISTLTLSKADYEKHKVYACEVTHQGLSSPVTKSFNRGEC SEQ. ID. NO. 46. pEHG1 Matuzumab VH WT, CH1 WT, N297Q, 7.8.60B
QVQLVQSGAEVKKPGASVKVSCKASGYTFTSHWMHWVRQAPGQGLEWIGEFNPSNGRTNYNEKFKSKATMTVDTSTNTAYMEL
SSLRSEDTAVYYCASRDYDYDGRYFDYWGQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYQSTYRVVSVLTVLHQDWLNGKEYKCKVSNKAL
PAPIEKTISKAKGQPRRPRVYTLPPSREEMTKNQVSLVCLVKGFYPSDIAVEWESNGQPENNYKTTPPVLDSDGSFFLYSVLT
VDKSRWQQGNVFSCSVMHEALHNHYTQKSLSLSPG SEQ. ID. NO. 47. Matuzumab VH WT, CH1 14.3.1.1B and 14.3.1.2B (K221E), N297Q, 7.8.60B
QVQLVQSGAEVKKPGASVKVSCKASGYTFTSHWMHWVRQAPGQGLEWIGEFNPSNGRTNYNEKFKSKATMTVDTSTNTAYMEL
SSLRSEDTAVYYCASRDYDYDGRYFDYWGQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDEKVEPKSCDKTHTCPPCPAPELLGGPSVFLFPP
KPKDTLMISRTPEVTCVVVDVSHEDPEVKFNWYVDGVEVHNAKTKPREEQYQSTYRVVSVLTVLHQDWLNGKEYKCKVSNKAL
PAPIEKTISKAKGQPRRPRVYTLPPSREEMTKNQVSLVCLVKGFYPSDIAVEWESNGQPENNYKTTPPVLDSDGSFFLYSVLT
VDKSRWQQGNVFSCSVMHEALHNHYTQKSLSLSPG SEQ. ID. NO. 48. Matuzumab VL WT, CK WT
DIQMTQSPSSLSASVGDRVTITCSASSSVTYMYWYQQKPGKAPKLLIYDTSNLASGVPSRFSGSGSGTDYTFTISSLQPEDIA
TYYCQQWSSHIFTFGQGTKVEIKRTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC SEQ. ID. NO. 49. Matuzumab VL WT, CK 14.3.1.1B and 14.3.1.2B (E123K)
DIQMTQSPSSLSASVGDRVTITCSASSSVTYMYWYQQKPGKAPKLLIYDTSNLASGVPSRFSGSGSGTDYTFTISSLQPEDIA
TYYCQQWSSHIFTFGQGTKVEIKRTVAAPSVFIFPPSDKQLKSGTASVVCLLNNFYPREAKVQWKVDNALQSGNSQESVTEQD
SKDSTYSLSSTLTLSKADYEKHKVYACEVTHQGLSSPVTKSFNRGEC SEQ. ID. NO. 50. BHA10 VH WT, CH1 WT, N297Q, 7.8.60B
QVQLVQSGAEVKKPGSSVKVSCKASGYTFTTYYLHWVRQAPGQGLEWMGWIYPGNVHAQYNEKFKGRVTITADKSTSTAYMEL
SSLRSEDTAVYYCARSWEGFPYWGQGTTVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYQSTYRVVSVLTVLHQDWLNGKEYKCKVSNKALPAPIE
KTISKAKGQPRRPRVYTLPPSREEMTKNQVSLVCLVKGFYPSDIAVEWESNGQPENNYKTTPPVLDSDGSFFLYSVLTVDKSR
WQQGNVFSCSVMHEALHNHYTQKSLSLSPG SEQ. ID. NO. 51. BHA10 VH WT, CH1 14.3.1.1B and 14.3.1.2B (K221E), N297Q 7.8.60B
QVQLVQSGAEVKKPGSSVKVSCKASGYTFTTYYLHWVRQAPGQGLEWMGWIYPGNVHAQYNEKFKGRVTITADKSTSTAYMEL
SSLRSEDTAVYYCARSWEGFPYWGQGTTVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDEKVEPKSCDKTHTCPPCPAPELLGGPSVFLFPPKPKDT
LMISRTPEVTCVVVDVSHEDPEVKFNWYVDGVEVHNAKTKPREEQYQSTYRVVSVLTVLHQDWLNGKEYKCKVSNKALPAPIE
KTISKAKGQPRRPRVYTLPPSREEMTKNQVSLVCLVKGFYPSDIAVEWESNGQPENNYKTTPPVLDSDGSFFLYSVLTVDKSR
WQQGNVFSCSVMHEALHNHYTQKSLSLSPG SEQ. ID. NO. 52. BHA10 VL WT, CK WT
DIQMTQSPSSLSASVGDRVTITCKASQNVGINVAWYQQKPGKAPKSLISSASYRYSGVPSRFSGSGSGTDFTLTISSLQPEDF
ATYFCQQYDTYPFTFGQGTKVEIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ. ID. NO. 53. BHA10 VL WT, CK 14.3.1.1B and 14.3.1.2B (E123K)
DIQMTQSPSSLSASVGDRVTITCKASQNVGINVAWYQQKPGKAPKSLISSASYRYSGVPSRFSGSGSGTDFTLTISSLQPEDF
ATYFCQQYDTYPFTFGQGTKVEIKRTVAAPSVFIFPPSDKQLKSGTASVVCLLNNFYPREAKVQWKVDNALQSGNSQESVTEQ
DSKDSTYSLSSTLTLSKADYEKHKVYACEVTHQGLSSPVTKSFNRGEC

| Sequences |
| --- |
| SEQ. ID. NO. 54: WT IgG1_V(-)<br>ASTKGPSVFPLAPSSKSTSGGTAALGCLVKDYFPEPVTVSWNSGALTSGVHTFPAVLQSSGLYSLSSVVTVPSSSLGTQTYIC<br>NVNHKPSNTKVDKKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 55: WT Ckappa_V(-)<br>RTVAAPSVFIFPPSDEQLKSGTASVVCLLNNFYPREAKVQWKVDNALQSGNSQESVTEQDSKDSTYSLSSTLTLSKADYEKHK<br>VYACEVTHQGLSSPVTKSFNRGEC |
| SEQ. ID. NO. 56: 14.1.2A IgG1_V(-)<br>ASTKGPSVFPLAPSSKSTSGGTAALGCLVADYFPEPVTVSWNSGALTSGVHTFPAVLQSSGLYSLSSVVTVPSSSLGTQTYIC<br>NVNHKPSNTKVDEKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 57: 14.1.2a Ckappa<br>RTVAAPSVFIFPPSDKQLKSGTARVVCLLNNFYPREAKVQWKVDNALQSGNSQESVTEQDSKDSTYSLSSTLTLSKADYEKHK<br>VYACEVTHQGLSSPVTKSFNRGEC |
| SEQ. ID. NO. 58: 14.3.1.1A IgG1_V(-)<br>ASTKGPSVFPLAPSSKSTSGGTAALGCLVADYFPEPVTVSWNSGALTSGVHTFPAVLQSSGLYSLASVVTVPSSSLGTQTYIC<br>NVNHKPSNTKVDKKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 59: 14.3.1.1a and 14.3.1.2a Ckappa<br>RTVAAPSVFIFPPSDEQLKSGTARVVCLLNNFYPREAKVQWKVDNALQSGNSQESVTEQDSKDSTYSLISTLTLSKADYEKHK<br>VYACEVTHQGLSSPVTKSFNRGEC |
| SEQ. ID. NO. 60: 14.3.1.1B and 14.3.1.2B IgG1_V(-)<br>ASTKGPSVFPLAPSSKSTSGGTAALGCLVKDYFPEPVTVSWNSGALTSGVHTFPAVLQSSGLYSLSSVVTVPSSSLGTQTYIC<br>NVNHKPSNTKVDEKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 61: 14.3.1.16 and 14.3.1.26 Ckappa<br>RTVAAPSVFIFPPSDKQLKSGTASVVCLLNNFYPREAKVQWKVDNALQSGNSQESVTEQDSKDSTYSLSSTLTLSKADYEKHK<br>VYACEVTHQGLSSPVTKSFNRGEC |
| SEQ IDNO: 62 14.3.1.2A IgG1_V(-)<br>ASTKGPSVFPLAPSSKSTSGGTAALGCLVADYFPEPVTVSWNSGALTSGVHTFPAVLQSSGLYSLGSVVTVPSSSLGTQTYIC<br>NVNHKPSNTKVDKKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 63: 15.1A IgG1_V(-)<br>ASTKGPSVFPLAPSSKSTSGGTAALGCLVADYFPEPVTVSWNSGALTSGVHTFPAVLQSSGLYSLASVVTVPSSSLGTQTYIC<br>NVNHKPSNTKVDEKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 64: 15.1a and 15.2a Ckappa<br>RTVAAPSVFIFPPSDKQLKSGTARVVCLLNNFYPREAKVQWKVDNALQSGNSQESVTEQDSKDSTYSLISTLTLSKADYEKHK<br>VYACEVTHQGLSSPVTKSFNRGEC |
| SEQ. ID. NO. 65: 15.2A IgG1_V(-)<br>ASTKGPSVFPLAPSSKSTSGGTAALGCLVADYFPEPVTVSWNSGALTSGVHTFPAVLQSSGLYSLGSVVTVPSSSLGTQTYIC<br>NVNHKPSNTKVDEKVEPKSCDKGSIEGRGSTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQQGNVFSCSVMHEALHNHYTQKSL<br>SLSPG |
| SEQ. ID. NO. 66: WT IgG1_CH1<br>ASTKGPSVFPLAPSSKSTSGGTAALGCLVKDYFPEPVTVSWNSGALTSGVHTFPAVLQSSGLYSLSSVVTVPSSSLGTQTYIC<br>NVNHKPSNTKVDKKV |
| SEQ. ID. NO. 67: 14.1.2A IgG1_ CH1<br>ASTKGPSVFPLAPSSKSTSGGTAALGCLVADYFPEPVTVSWNSGALTSGVHTFPAVLQSSGLYSLSSVVTVPSSSLGTQTYIC<br>NVNHKPSNTKVDEKV |

| Sequences |
|---|
| SEQ. ID. NO. 68: 14.3.1.1A IgG1_ CH1<br>ASTKGPSVFPLAPSSKSTSGGTAALGCLVADYFPEPVTVSWNSGALTSGVHTFPAVLQSSGLYSLASVVTVPSSSLGTQTYIC<br>NVNHKPSNTKVDKKV<br><br>SEQ. ID. NO. 69: 14.3.1.1B and 14.3.1.2B IgG1_ CH1<br>ASTKGPSVFPLAPSSKSTSGGTAALGCLVKDYFPEPVTVSWNSGALTSGVHTFPAVLQSSGLYSLSSVVTVPSSSLGTQTYIC<br>NVNHKPSNTKVDEKV<br><br>SEQ IDNO: 70 14.3.1.2A IgG1_ CH1<br>ASTKGPSVFPLAPSSKSTSGGTAALGCLVADYFPEPVTVSWNSGALTSGVHTFPAVLQSSGLYSLGSVVTVPSSSLGTQTYIC<br>NVNHKPSNTKVDKKV<br><br>SEQ. ID. NO. 71: 15.1A IgG1_ CH1<br>ASTKGPSVFPLAPSSKSTSGGTAALGCLVADYFPEPVTVSWNSGALTSGVHTFPAVLQSSGLYSLASVVTVPSSSLGTQTYIC<br>NVNHKPSNTKVDEKV<br><br>SEQ. ID. NO. 72: 15.2A IgG1_ CH1<br>ASTKGPSVFPLAPSSKSTSGGTAALGCLVADYFPEPVTVSWNSGALTSGVHTFPAVLQSSGLYSLGSVVTVPSSSLGTQTYIC<br>NVNHKPSNTKVDEKV<br><br>SEQ ID NO. 73. Human IgG1 Fc_(WT)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK<br><br>SEQ ID NO. 74. Human IgG1 Fc_(7.8_A CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQVSLTCLVKGFYPSDIAVEWESNGQPENNYKTTPP<br>VLMSDGSFFLASKLTVDKSRWQQGNVFSCSVMHEALHNHYTQKSLSLSPGK<br><br>SEQ ID NO. 75. Human IgG1 Fc _(7.8.60_A CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTDNQVSLTCLVKGFYPSDIAVEWESNGQPENNYKTTPP<br>VLMSDGSFFLASKLTVDKSRWQQGNVFSCSVMHEALHNHYTQKSLSLSPGK<br><br>SEQ ID NO. 76. Human IgG1 FC _(20.8_A, 20.8.31_A or 20.8.33_A CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVSTLPPSREEMTKNQVSLVCLVYGFYPSDIAVEWESNGQPENNYKTTPP<br>VLDSDGSFFLYSVLTVDKSRWQQGNVFSCSVMHEALHNHYTQKSLSLSPGK<br><br>SEQ ID NO. 77. Human IgG1 Fc _(20.8.26_A, 20.8.34_A or 20.8.37_A CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVSTLPPSREEMTKNQVSLMCLVYGFYPSDIAVEWESNGQPENNYKTTPP<br>VLDSDGSFFLYSVLTVDKSRWQQGNVFSCSVMHEALHNHYTQKSLSLSPGK<br><br>SEQ ID NO. 78. Human IgG1 FC _(7.8B or 7.4_B CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQVSLVCLVKGFYPSDIAVEWESNGQPENNYKTTPP<br>VLDSDGSFFLYSVLTVDKSRWQQGNVFSCSVMHEALHNHYTQKSLSLSPGK<br><br>SEQ ID NO. 79. Human IgG1 Fc _(7.8.60_B CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPRRPRVYTLPPSREEMTKNQVSLVCLVKGFYPSDIAVEWESNGQPENNYKTTPP<br>VLDSDGSFFLYSVLTVDKSRWQQGNVFSCSVMHEALHNHYTQKSLSLSPGK<br><br>SEQ ID NO. 80. Human IgG1 Fc _(7.8.60_B or 20.8.26_B CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREDMTKNQVQLTCLVKGFYPSDIAVEWESNGQPENNYKTTPP<br>VLDSDGSFFLASKLTVDKSRWQQGNVFSCSVMHEALHNHYTQKSLSLSPGK<br><br>SEQ ID NO. 81. Human IgG1 Fc _(20.8.33_B or 20.8.34_B CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSRGDMTKNQVQLTCLVKGFYPSDIAVEWESNGQPENNYKTTPP<br>VLDSDGSFFLASKLTVDKSRWQQGNVFSCSVMHEALHNHYTQKSLSLSPGK<br><br>SEQ ID NO. 82. Human IgG1 Fc _(20.8.31_B or 20.8.37_B CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREDMTKNQVRLTCLVKGFYPSDIAVEWESNGQPENNYKTTPP<br>VLDSDGSFFLASKLTVDKSRWQQGNVFSCSVMHEALHNHYTQKSLSLSPGK<br><br>SEQ ID NO. 83. Human IgG1 Fc _(7.4_A CH3)<br>APELLGGPSVFLFPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQVSLTCLVKGFYPSDIAVEWESNGQPENNYKTTPP<br>VLDSDGSFFLASKLTVDKSRWQQGNVFSCSVMHEALHNHYTQKSLSLSPGK |

| Sequences |
| --- |

SEQ ID NO. 84. Human IgG1 Fc _(7.4_B + 366M CH3)
APELLGGPSVFLFPPKPKDTLMISRTPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLMCLVKGFYPSDIAVEWESNGQPENNYKTTPP
VLDSDGSFFLYSVLTVDKSRWQQGNVFSCSVMHEALHNHYTQKSLSLSPGK (Bold underlined residues represent mutations to parental mAb or WT sequence)

We claim:

1. A method for producing a first and second fragment, antigen binding (Fab) comprising:
   (1) co-expressing in a host cell:
      (a) a first nucleic acid sequence encoding both a first heavy chain variable domain ($V_H$) and a first human IgG heavy chain constant $C_H1$ ($C_H1$) domain, wherein said first human $C_H1$ domain comprises an alanine at residue 145 according to Kabat Numbering and an alanine or a glycine at residue 188 according to Kabat Numbering;
      (b) a second nucleic acid sequence encoding both a first light chain variable domain ($V_L$) and a first human light chain kappa constant (Ck) domain, wherein said first human Ck domain comprises an arginine at residue 131 according to Kabat Numbering and an isoleucine at residue 176 according to Kabat Numbering;
      (c) a third nucleic acid encoding both a second $V_H$ domain and a second human $C_H1$ domain; and
      (d) a fourth nucleic acid encoding both a second $V_L$ domain and a second human Ck domain, and
   wherein:
      (i) said second human $C_H1$ domain has the wild-type human IgG $C_H1$ sequence and said second human Ck domain has the wild type human Ck sequence;
      (ii) said second human $C_H1$ domain comprises an isoleucine at residue 188 according to Kabat Numbering and said second human Ck domain has an alanine or a glycine at residue 176 according to Kabat Numbering; or
      (iii) said second human $C_H1$ domain comprises a glutamic acid at residue 221 according to Kabat Numbering and said second human Ck domain has lysine at residue 123 according to Kabat Numbering;
   wherein each of said first $V_H$ and $V_L$ domains comprise three complementarity determining regions (CDRs) which direct binding to a first antigen and further wherein each of said second $V_H$ and $V_L$ domains comprise three CDRs which direct binding to a second antigen that differs from said first antigen;
   (2) cultivating said host cell under conditions such that said first and second $V_H$ and human $C_H1$ domains and said first and second $V_L$ and human Ck domains are produced; and
   (3) recovering from said host cell a first and second Fabs wherein said first Fab comprises said first $V_H$ and first human $C_H1$ domains and said first $V_L$ and first human Ck domains, and said second Fab comprises said second $V_H$ and second human $C_H1$ domains and said second $V_L$ and second human Ck domains.

2. The method according to claim 1, wherein said first human $C_H1$ domain further comprises a glutamic acid at residue 221 according to Kabat Numbering and said first human Ck domain further comprises a lysine at residue 123 according to Kabat Numbering and wherein said second human $C_H1$ domain has the wild-type human IgG $C_H1$ sequence and said second human Ck domain has the wild-type human Ck sequence.

3. The method according to claim 1 wherein,
   (a) said first $V_H$ domain comprises a glutamic acid at residue 62 and a lysine at residue 39 according to Kabat Numbering;
   (b) said first $V_L$ domain is kappa isotype and comprises an arginine at residue 1 and an aspartic acid at residue 38 according to Kabat Numbering;
   (c) said second $V_H$ domain comprises a tyrosine at residue 39 and an arginine at residue 105 according to Kabat Numbering; and
   (d) said second $V_L$ domain is kappa isotype and comprises an arginine at residue 38 and an aspartic acid at residue 42 according to Kabat Numbering.

4. The method according to claim 1, wherein,
   (a) said first $V_H$ domain comprises a tyrosine at residue 39 and an arginine at residue 105 according to Kabat Numbering;
   (b) said first $V_L$ domain is kappa isotype and comprises an arginine at residue 38 and an aspartic acid at residue 42 according to Kabat Numbering;
   (c) said second $V_H$ domain comprises a glutamic acid at residue 62 and a lysine at residue 39 according to Kabat Numbering; and
   (d) said second $V_L$ domain is kappa isotype and comprises an arginine at residue 1 and an aspartic acid at residue 38 according to Kabat Numbering.

5. The method according to claim 1, wherein each of said first and second human $C_H1$ domains are individually IgG1 or IgG4 isotype.

6. The method according to claim 5, wherein each of said first and second human $C_H1$ domains are IgG1 isotype.

7. The method according to claim 5, wherein each of said first and second human $C_H1$ domains are IgG4 isotype.

8. A method for producing a bispecific antibody comprising:
   (1) co-expressing in a host cell:
      (a) a first nucleic acid sequence encoding, in order,
         i) a first $V_H$ domain and a first human IgG heavy chain constant region, wherein said first human IgG heavy chain constant region comprises a first human $C_H1$ domain comprising an alanine at residue 145 according to Kabat Numbering and an alanine or a glycine at residue 188 according to Kabat Numbering and,
         (ii) a hinge region;
      (b) a second nucleic acid sequence encoding both a first $V_L$ domain and a first human Ck domain, wherein said first human Ck domain comprises an arginine at residue 131 according to Kabat Numbering and an isoleucine at residue 176 according to Kabat Numbering;

(c) a third nucleic acid encoding, in order,
   i) a second $V_H$ and a second human IgG heavy chain constant region; and
   (ii) a hinge region; and
(d) a fourth nucleic acid encoding both a second $V_L$ and a second human Ck domain,
wherein:
   (i) said second human IgG heavy chain constant region comprises a second human $C_H1$ domain that has the wild-type human IgG $C_H1$ sequence and said second human Ck domain has the wild type human Ck sequence;
   (ii) said second human IgG heavy chain constant region comprises a second human $C_H1$ domain that comprises an isoleucine at residue 188 according to Kabat Numbering and said second human Ck domain has an alanine or a glycine at residue 176 according to Kabat Numbering; or
   (iii) said second human IgG heavy chain constant region comprises a second human $C_H1$ domain that comprises a glutamic acid at residue 221 according to Kabat Numbering and said second human Ck domain has lysine at residue 123 according to Kabat Numbering;
wherein each of said first $V_H$ and $V_L$ domains comprise three CDRs which direct binding to a first antigen and further wherein each of said second heavy chain and light chain variable domains comprise three CDRs which direct binding to a second antigen that differs from said first antigen;
(2) cultivating said host cell under conditions such that said first and second $V_H$ and human $C_H1$ domains and said first and second $V_L$ and human Ck domains are produced; and
(3) recovering from said host cell an IgG bispecific antibody comprising a first and second Fabs wherein said first Fab comprises said first $V_H$ and first human $C_H1$ domains and said first $V_L$ and first human Ck domains, and said second Fab comprises said second $V_H$ and second human $C_H1$ domains and said second $V_L$ and second human Ck domains.

9. The method according to claim 8, wherein said first human $C_H1$ domain further comprises glutamic acid at residue 221 according to Kabat Numbering and said first human Ck domain further comprises a lysine at residue 123 according to Kabat Numbering and wherein said second human $C_H1$ domain has the wild-type human IgG $C_H1$ sequence and said second human Ck domain has the wild-type human Ck sequence.

10. The method according to claim 8, wherein,
(a) said first $V_H$ domain comprises a glutamic acid at residue 62 and a lysine at residue 39 according to Kabat Numbering;
(b) said first $V_L$ domain is kappa isotype and comprises an arginine at residue 1 and an aspartic acid at residue 38 according to Kabat Numbering;
(c) said second $V_H$ domain comprises a tyrosine at residue 39 and an arginine at residue 105 according to Kabat Numbering; and
(d) said second $V_L$ domain is kappa isotype and comprises an arginine at residue 38 and an aspartic acid at residue 42 according to Kabat Numbering.

11. The method according to claim 8, wherein,
(a) said first $V_H$ domain comprises a tyrosine at residue 39 and an arginine at residue 105 according to Kabat Numbering;
(b) said first $V_L$ domain is kappa isotype and comprises an arginine at residue 38 and an aspartic acid at residue 42 according to Kabat Numbering;
(c) said second $V_H$ domain comprises a glutamic acid at residue 62 and a lysine at residue 39 according to Kabat Numbering; and
(d) said second $V_L$ domain is kappa isotype and comprises an arginine at residue 1 and an aspartic acid at residue 38 according to Kabat Numbering.

12. The method according to claim 8, wherein one of said first or second human IgG constant regions comprises a CH3 domain comprising an alanine at residue 407 according to EU Index Numbering; and the other of said first or second human IgG constant regions comprises a CH3 domain comprising a valine or methionine at residue 366 and a valine at residue 409 according to EU Index Numbering.

13. The method according to claim 8, wherein one of said first or second human IgG constant regions comprises a $C_H3$ domain comprising an alanine at residue 407, a methionine at residue 399, and an aspartic acid at residue 360 according to EU Index Numbering; and the other of said first or second human IgG constant regions comprises a CH3 domain comprising a valine at residue 366, a valine at residue 409, and an arginine at residues 345 and 347 according to EU Index Numbering.

14. The method according to claim 8, wherein one of said first or second human IgG constant regions comprises a $C_H3$ domain comprising an alanine at residue 407, a glycine at residue 356, an aspartic acid at residue 357, and a glutamine at residue 364 according to EU Index Numbering; and the other of said first or second human IgG constant regions comprises a $C_H3$ domain comprising a methionine at residue 366, a valine at residue 409, a serine at residue 349, and a tyrosine at residue 370 according to EU Index Numbering.

15. The method according to claim 8, wherein each of said first and second human $C_Hi$ domains are IgG1 or IgG4 isotype.

16. The method according to claim 15, wherein each of said first and second human $C_H1$ domains are IgG1 isotype.

17. The method according to claim 15, wherein each of said first and second human $C_Hi$ domains are IgG4 isotype.

18. The method according to claim 8, wherein each of said first and second $V_L$ domains is human kappa isotype.

19. A method for producing a first and second fragment, antigen binding (Fab) comprising:
(1) co-expressing in a host cell:
   (a) a first nucleic acid sequence encoding both a first heavy chain variable domain ($V_H$) and a first human IgG heavy chain constant $C_H1$ ($C_H1$) domain, wherein said first human $C_H1$ domain comprises an alanine at residue 145 according to Kabat Numbering and a glutamic acid at residue 221 according to Kabat Numbering;
   (b) a second nucleic acid sequence encoding both a first light chain variable domain ($V_L$) and a first human light chain kappa constant (Ck) domain, wherein said first human Ck domain comprises an arginine at residue 131 according to Kabat Numbering and a lysine at residue 123 according to Kabat Numbering;
   (c) a third nucleic acid encoding both a second $V_H$ domain and a second human $C_H1$ domain, wherein said second human $C_H1$ domain has the wild type human IgG $C_H1$ sequence; and
   (d) a fourth nucleic acid encoding both a second $V_L$ domain and a second human Ck domain, wherein said second human Ck domain has the wild type human Ck sequence, wherein each of said first $V_H$ and $V_L$ domains comprise three complementarity determining regions (CDRs) which direct binding to a first antigen and further wherein each of said second $V_H$ and $V_L$ domains comprise three CDRs which direct binding to a second antigen that differs from said first antigen;

(2) cultivating said host cell under conditions such that said first and second $V_H$ and human $C_H1$ domains and said first and second $V_L$ and human Ck domains are produced; and (3) recovering from said host cell a first and second Fabs wherein said first Fab comprises said first $V_H$ and first human $C_H1$ domains and said first $V_L$ and first human Ck domains, and said second Fab comprises said second $V_H$ and second human $C_H1$ domains and said second $V_L$ and second human Ck domains.

20. The method according to claim 19 wherein,
(a) said first $V_H$ domain comprises a glutamic acid at residue 62 and a lysine at residue 39 according to Kabat Numbering;
(b) said first $V_L$ domain is kappa isotype and comprises an arginine at residue 1 and an aspartic acid at residue 38 according to Kabat Numbering;
(c) said second $V_H$ domain comprises a tyrosine at residue 39 and an arginine at residue 105 according to Kabat Numbering; and
(d) said second $V_L$ domain is kappa isotype and comprises an arginine at residue 38 and an aspartic acid at residue 42 according to Kabat Numbering.

21. The method according to claim 19, wherein,
(a) said first $V_H$ domain comprises a tyrosine at residue 39 and an arginine at residue 105 according to Kabat Numbering;
(b) said first $V_L$ domain is kappa isotype and comprises an arginine at residue 38 and an aspartic acid at residue 42 according to Kabat Numbering;
(c) said second $V_H$ domain comprises a glutamic acid at residue 62 and a lysine at residue 39 according to Kabat Numbering; and
(d) said second $V_L$ domain is kappa isotype and comprises an arginine at residue 1 and an aspartic acid at residue 38 according to Kabat Numbering.

22. The method according to claim 19, wherein each of said first and second human $C_H1$ domains are individually IgG1 or IgG4 isotype.

23. The method according to claim 22, wherein each of said first and second human $C_H1$ domains are IgG1 isotype.

24. The method according to claim 22, wherein each of said first and second human $C_H1$ domains are IgG4 isotype.

25. A method for producing a bispecific antibody comprising:
(1) co-expressing in a host cell:
(a) a first nucleic acid sequence encoding, in order,
i) a first $V_H$ domain and a first human IgG heavy chain constant region, wherein said first human IgG heavy chain constant region comprises a first human $C_H1$ domain comprising an alanine at residue 145 according to Kabat Numbering and a glutamic acid at residue 221 according to Kabat Numbering and,
(ii) a hinge region;
(b) a second nucleic acid sequence encoding both a first $V_L$ domain and a first human Ck domain, wherein said first human Ck domain comprises an arginine at residue 131 according to Kabat Numbering and a lysine at residue 123 according to Kabat Numbering;

(c) a third nucleic acid encoding, in order,
i) a second $V_H$ and a second human IgG heavy chain constant region, wherein said second human IgG heavy chain constant region comprises a second human $C_H1$ domain that has the wild type human IgG $C_H1$ sequence; and
(ii) a hinge region; and
(d) a fourth nucleic acid encoding both a second $V_L$ and a second human Ck domain, wherein said second human Ck domain has the wild type human Ck sequence, wherein each of said first $V_H$ and $V_L$ domains comprise three CDRs which direct binding to a first antigen and further wherein each of said second heavy chain and light chain variable domains comprise three CDRs which direct binding to a second antigen that differs from said first antigen;

(2) cultivating said host cell under conditions such that said first and second $V_H$ and human $C_H1$ domains and said first and second $V_L$ and human Ck domains are produced; and (3) recovering from said host cell an IgG bispecific antibody comprising first and second Fabs wherein said first Fab comprises said first $V_H$ and first human $C_H1$ domains and said first $V_L$ and first human Ck domains, and said second Fab comprises said second $V_H$ and second human $C_H1$ domains and said second $V_L$ and second human Ck domains.

26. The method according to claim 25, wherein,
(a) said first $V_H$ domain comprises a glutamic acid at residue 62 and a lysine at residue 39 according to Kabat Numbering;
(b) said first $V_L$ domain is kappa isotype and comprises an arginine at residue 1 and an aspartic acid at residue 38 according to Kabat Numbering;
(c) said second $V_H$ domain comprises a tyrosine at residue 39 and an arginine at residue 105 according to Kabat Numbering; and
(d) said second $V_L$ domain is kappa isotype and comprises an arginine at residue 38 and an aspartic acid at residue 42 according to Kabat Numbering.

27. The method according to claim 25, wherein,
(a) said first $V_H$ domain comprises a tyrosine at residue 39 and an arginine at residue 105 according to Kabat Numbering;
(b) said first $V_L$ domain is kappa isotype and comprises an arginine at residue 38 and an aspartic acid at residue 42 according to Kabat Numbering;
(c) said second $V_H$ domain comprises a glutamic acid at residue 62 and a lysine at residue 39 according to Kabat Numbering; and
(d) said second $V_L$ domain is kappa isotype and comprises an arginine at residue 1 and an aspartic acid at residue 38 according to Kabat Numbering.

28. The method according to claim 25, wherein one of said first or second human IgG constant regions comprises a $C_H3$ domain comprising an alanine at residue 407 with residue according to EU Index Numbering; and the other of said first or second human IgG constant regions comprises a $C_H3$ domain comprising a valine or methionine at residue 366 and a valine at residue 409 according to EU Index Numbering.

29. The method according to claim 25, wherein one of said first or second human IgG constant regions comprises a $C_H3$ domain comprising an alanine at residue 407, a methionine at residue 399, and an aspartic acid at residue 360 according to EU Index Numbering; and the other of said first or second human IgG constant regions comprises a $C_H3$ domain comprising a valine at residue 366, a valine at residue 409, and an arginine at residues 345 and 347 according to EU Index Numbering.

30. The method according to claim 25, wherein one of said first or second human IgG constant regions comprises a $C_H3$ domain comprising an alanine at residue 407, a glycine at residue 356, an aspartic acid at residue 357, and a glutamine at residue 364 according to EU Index Numbering; and the other of said first or second human IgG constant regions comprises a $C_H3$ domain comprising a methionine at residue 366, a valine at residue 409, a serine at residue 349, and a tyrosine at residue 370 according to EU Index Numbering.

31. The method according to claim 25, wherein each of said first and second human $C_H1$ domains are IgG1 or IgG4 isotype.

32. The method according to claim 31, wherein each of said first and second human $C_H1$ domains are IgG1 isotype.

33. The method according to claim 31, wherein each of said first and second human $C_H1$ domains are IgG4 isotype.

34. The method according to claim 25, wherein each of said first and second $V_L$ domains is human kappa isotype.

* * * * *

UNITED STATES PATENT AND TRADEMARK OFFICE
CERTIFICATE OF CORRECTION

PATENT NO. : 11,820,828 B2
APPLICATION NO. : 16/465689
DATED : November 21, 2023
INVENTOR(S) : Stephen John Demarest et al.

Page 1 of 1

It is certified that error appears in the above-identified patent and that said Letters Patent is hereby corrected as shown below:

In the Claims

Claim 15, Column 190, Line 36, delete: "$C_H i$" and insert --$C_H 1$--

Claim 17, Column 190, Line 41, delete: "$C_H i$" and insert --$C_H 1$--

Signed and Sealed this
Sixteenth Day of April, 2024

Katherine Kelly Vidal
*Director of the United States Patent and Trademark Office*

SEQUENCE LISTING

<160> NUMBER OF SEQ ID NOS: 84

<210> SEQ ID NO 1
<211> LENGTH: 337
<212> TYPE: PRT
<213> ORGANISM: Artificial Sequence
<220> FEATURE:
<223> OTHER INFORMATION: Synthetic Construct

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285
```

```
Leu Asp Ser Asp Gly Ser Phe Phe Leu Tyr Ser Lys Leu Thr Val Asp
        290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly

<210> SEQ ID NO 2
<211> LENGTH: 107
<212> TYPE: PRT
<213> ORGANISM: Artificial Sequence
<220> FEATURE:
<223> OTHER INFORMATION: Synthetic Construct

<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 3
<211> LENGTH: 122
<212> TYPE: PRT
<213> ORGANISM: Artificial Sequence
<220> FEATURE:
<223> OTHER INFORMATION: Synthetic Construct

<400> SEQUENCE: 3

His His His His His His His Gly Gly Gly Gly Ser Thr Gly Arg
1               5                   10                  15

Thr Val Ala Ala Pro Ser Val Phe Ile Phe Pro Pro Ser Asp Glu Gln
            20                  25                  30

Leu Lys Ser Gly Thr Ala Ser Val Val Cys Leu Leu Asn Asn Phe Tyr
        35                  40                  45

Pro Arg Glu Ala Lys Val Gln Trp Lys Val Asp Asn Ala Leu Gln Ser
    50                  55                  60

Gly Asn Ser Gln Glu Ser Val Thr Glu Gln Asp Ser Lys Asp Ser Thr
65                  70                  75                  80

Tyr Ser Leu Ser Ser Thr Leu Thr Leu Ser Lys Ala Asp Tyr Glu Lys
                85                  90                  95

His Lys Val Tyr Ala Cys Glu Val Thr His Gln Gly Leu Ser Ser Pro
            100                 105                 110

Val Thr Lys Ser Phe Asn Arg Gly Glu Cys
        115                 120

<210> SEQ ID NO 4
```

<211> LENGTH: 448
<212> TYPE: PRT
<213> ORGANISM: Artificial Sequence
<220> FEATURE:
<223> OTHER INFORMATION: Synthetic Construct

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Tyr Lys Thr Thr Pro Val Leu
385                 390                 395                 400

Met Ser Asp Gly Ser Phe Phe Leu Ala Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

<210> SEQ ID NO 5
<211> LENGTH: 448
<212> TYPE: PRT
<213> ORGANISM: Artificial Sequence
<220> FEATURE:
<223> OTHER INFORMATION: Synthetic Construct

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 6
<211> LENGTH: 448
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ala Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 7
<211> LENGTH: 448
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Gly Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Asp Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 8
<211> LENGTH: 448
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ala Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 9
<211> LENGTH: 448
<212> TYPE: PRT
<213> ORGANISM: Artificial Sequence
<220> FEATURE:

<223> OTHER INFORMATION: Synthetic Construct

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Gly Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400
```

-continued

```
Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 10
<211> LENGTH: 220
<212> TYPE: PRT
<213> ORGANISM: Artificial Sequence
<220> FEATURE:
<223> OTHER INFORMATION: Synthetic Construct

<400> SEQUENCE: 10

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 11
<211> LENGTH: 220
<212> TYPE: PRT
<213> ORGANISM: Artificial Sequence
<220> FEATURE:
<223> OTHER INFORMATION: Synthetic Construct

<400> SEQUENCE: 11

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45
```

```
Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Ala Tyr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Lys Gln Leu Lys Ser Gly Thr Ala Arg Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 12
<211> LENGTH: 220
<212> TYPE: PRT
<213> ORGANISM: Artificial Sequence
<220> FEATURE:
<223> OTHER INFORMATION: Synthetic Construct

<400> SEQUENCE: 12

Arg Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Tyr Thr
                 20                  25                  30

Ser Ser Gln Lys Asn Tyr Leu Ala Trp Tyr Gln Asp Lys Pro Gly Lys
             35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Ala Tyr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Arg Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ile Ser Thr Leu Thr Leu Ser Lys Ala Asp Tyr
                180                 185                 190
```

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 13
<211> LENGTH: 220
<212> TYPE: PRT
<213> ORGANISM: Artificial Sequence
<220> FEATURE:
<223> OTHER INFORMATION: Synthetic Construct

<400> SEQUENCE: 13

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Lys Gln Leu Lys Ser Gly Thr Ala Arg Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ile Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 14
<211> LENGTH: 448
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
```

```
            50                  55                  60
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asn Leu Gly Pro Ser Phe Tyr Phe Asp Tyr Trp Gly Gln Gly
                    100                 105                 110

Thr Leu Val Thr Val Ser Ser Ala Ser Thr Lys Gly Pro Ser Val Phe
                    115                 120                 125

Pro Leu Ala Pro Ser Ser Lys Ser Thr Ser Gly Gly Thr Ala Ala Leu
                    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
                    195                 200                 205

Ser Asn Thr Lys Val Asp Lys Lys Val Glu Pro Lys Ser Cys Asp Lys
                    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Gln Ser Thr Tyr Arg Val
                    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Glu Glu Met Thr Asp Asn Gln Val Ser Leu Thr
                    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

<210> SEQ ID NO 15
<211> LENGTH: 448
<212> TYPE: PRT
<213> ORGANISM: Artificial Sequence
```

<220> FEATURE:
<223> OTHER INFORMATION: Synthetic Construct

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Met Ser Asp Gly Ser Phe Phe Leu Ala Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 16
<211> LENGTH: 448
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
            35                  40                  45

Ala Asp Val Asn Pro Asn Ser Gly Gly Ser Ile Tyr Asn Gln Glu Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ala Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
            290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 17
<211> LENGTH: 448
<212> TYPE: PRT
<213> ORGANISM: Artificial Sequence
<220> FEATURE:
<223> OTHER INFORMATION: Synthetic Construct

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Gly Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 18
<211> LENGTH: 448
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ala Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 19
<211> LENGTH: 448
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
            35                  40                  45

Ala Asp Val Asn Pro Asn Ser Gly Gly Ser Ile Tyr Asn Gln Glu Phe
        50                  55                  60

Lys Gly Arg Phe Thr Leu Ser Val Asp Arg Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Gly Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 20
<211> LENGTH: 214
<212> TYPE: PRT
<213> ORGANISM: Artificial Sequence
<220> FEATURE:
<223> OTHER INFORMATION: Synthetic Construct

<400> SEQUENCE: 20
```

```
Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 214
<212> TYPE: PRT
<213> ORGANISM: Artificial Sequence
<220> FEATURE:
<223> OTHER INFORMATION: Synthetic Construct

<400> SEQUENCE: 21

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Lys Gln Leu Lys Ser Gly
        115                 120                 125

Thr Ala Arg Val Val Cys Leu Leu Asn Asn Phe Tyr Pro Arg Glu Ala
130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ile
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 214
<212> TYPE: PRT
<213> ORGANISM: Artificial Sequence
<220> FEATURE:
<223> OTHER INFORMATION: Synthetic Construct

<400> SEQUENCE: 23

Arg Ile Gln Met Thr Gln Ser Pro Ser Ser Leu Ser Ala Ser Val Gly

```
1               5                   10                  15
Asp Arg Val Thr Ile Thr Cys Lys Ala Ser Gln Asp Val Ser Ile Gly
                20                  25                  30

Val Ala Trp Tyr Gln Asp Lys Pro Gly Lys Ala Pro Lys Leu Leu Ile
                35                  40                  45

Tyr Ser Ala Ser Tyr Arg Tyr Thr Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Lys Gln Leu Lys Ser Gly
                115                 120                 125

Thr Ala Arg Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ile
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 24
<211> LENGTH: 450
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Tyr Ala Pro Gly Gln Gly Leu Glu Trp Ile
                35                  40                  45

Gly Glu Phe Asn Pro Ser Asn Gly Arg Thr Asn Tyr Asn Glu Lys Phe
                50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
```

```
                145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Gln Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Arg Val
                340                 345                 350

Tyr Thr Leu Pro Pro Ser Arg Glu Glu Met Thr Lys Asn Gln Val Ser
        355                 360                 365

Leu Val Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Val Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly
    450

<210> SEQ ID NO 25
<211> LENGTH: 450
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Tyr Ala Pro Gly Gln Gly Leu Glu Trp Ile
                35                  40                  45

Gly Glu Phe Asn Pro Ser Asn Gly Arg Thr Asn Tyr Asn Glu Lys Phe
```

```
            50                  55                  60
Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Arg Pro Arg Val
            340                 345                 350

Tyr Thr Leu Pro Pro Ser Arg Glu Glu Met Thr Lys Asn Gln Val Ser
        355                 360                 365

Leu Val Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Val Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 26
```

```
<211> LENGTH: 213
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Arg Lys Pro Gly Asp Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 27
<211> LENGTH: 213
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Arg Lys Pro Gly Asp Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
```

```
                 100                 105                 110
Ser Val Phe Ile Phe Pro Pro Ser Asp Lys Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 28
<211> LENGTH: 445
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
            35                  40                  45

Gly Trp Ile Tyr Pro Gly Asn Val His Ala Gln Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
```

```
                    245                 250                 255
Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Gln Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Arg Pro Arg Val Tyr Thr Leu Pro Pro
            340                 345                 350

Ser Arg Glu Glu Met Thr Lys Asn Gln Val Ser Leu Val Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 29
<211> LENGTH: 445
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                165                 170                 175
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Arg Val Tyr Thr Leu Pro Pro
            340                 345                 350

Ser Arg Glu Glu Met Thr Lys Asn Gln Val Ser Leu Val Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 30
<211> LENGTH: 214
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Asp Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
```

```
                  85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 214
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Asp Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Lys Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 32
<211> LENGTH: 448
<212> TYPE: PRT
<213> ORGANISM: Artificial Sequence
<220> FEATURE:
<223> OTHER INFORMATION: Synthetic Construct

<400> SEQUENCE: 32
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | Ser | Leu | Arg | Leu | Ser | Cys | Ala | Ala | Ser | Gly | Tyr | Thr | Phe | Thr |
| | | | 20 | | | | | 25 | | | | | 30 | |
| Ser | Tyr | Trp | Leu | His | Trp | Val | Arg | Gln | Ala | Pro | Gly | Lys | Gly | Leu |
| | | | 35 | | | | | 40 | | | | | 45 | |
| Glu | Trp | Val | Gly | Met | Ile | Asp | Pro | Ser | Asn | Ser | Asp | Thr | Arg | Phe |
| | | | 50 | | | | | 55 | | | | | 60 | |
| Asn | Pro | Asn | Phe | Lys | Asp | Arg | Phe | Thr | Ile | Ser | Ala | Asp | Thr | Ser |
| 65 | | | | | 70 | | | | | 75 | | | | 80 |
| Lys | Asn | Thr | Ala | Tyr | Leu | Gln | Met | Asn | Ser | Leu | Arg | Ala | Glu | Asp |
| | | | | 85 | | | | | 90 | | | | | 95 |
| Thr | Ala | Val | Tyr | Tyr | Cys | Ala | Thr | Tyr | Arg | Ser | Tyr | Val | Thr | Pro |
| | | | | 100 | | | | | 105 | | | | | 110 |
| Leu | Asp | Tyr | Trp | Gly | Gln | Gly | Thr | Leu | Val | Thr | Val | Ser | Ser | Ala |
| | | | | 115 | | | | | 120 | | | | | 125 |
| Ser | Thr | Lys | Gly | Pro | Ser | Val | Phe | Pro | Leu | Ala | Pro | Ser | Ser | Lys |
| | | 130 | | | | | 135 | | | | | 140 | | |
| Ser | Thr | Ser | Gly | Gly | Thr | Ala | Ala | Leu | Gly | Cys | Leu | Val | Lys | Asp |
| 145 | | | | | 150 | | | | | 155 | | | | 160 |
| Tyr | Phe | Pro | Glu | Pro | Val | Thr | Val | Ser | Trp | Asn | Ser | Gly | Ala | Leu |
| | | | | 165 | | | | | 170 | | | | | 175 |
| Thr | Ser | Gly | Val | His | Thr | Phe | Pro | Ala | Val | Leu | Gln | Ser | Ser | Gly |
| | | | | 180 | | | | | 185 | | | | | 190 |
| Leu | Tyr | Ser | Leu | Ser | Ser | Val | Val | Thr | Val | Pro | Ser | Ser | Ser | Leu |
| | | | | 195 | | | | | 200 | | | | | 205 |
| Gly | Thr | Gln | Thr | Tyr | Ile | Cys | Asn | Val | Asn | His | Lys | Pro | Ser | Asn |
| | | 210 | | | | | 215 | | | | | 220 | | |
| Thr | Lys | Val | Asp | Lys | Lys | Val | Glu | Pro | Lys | Ser | Cys | Asp | Lys | Thr |
| 225 | | | | | 230 | | | | | 235 | | | | 240 |
| His | Thr | Cys | Pro | Pro | Cys | Pro | Ala | Pro | Glu | Leu | Leu | Gly | Gly | Pro |
| | | | | 245 | | | | | 250 | | | | | 255 |
| Ser | Val | Phe | Leu | Phe | Pro | Pro | Lys | Pro | Lys | Asp | Thr | Leu | Met | Ile |
| | | | | 260 | | | | | 265 | | | | | 270 |
| Ser | Arg | Thr | Pro | Glu | Val | Thr | Cys | Val | Val | Val | Asp | Val | Ser | His |
| | | | | 275 | | | | | 280 | | | | | 285 |
| Glu | Asp | Pro | Glu | Val | Lys | Phe | Asn | Trp | Tyr | Val | Asp | Gly | Val | Glu |
| | | 290 | | | | | 295 | | | | | 300 | | |
| Val | His | Asn | Ala | Lys | Thr | Lys | Pro | Arg | Glu | Glu | Gln | Tyr | Gln | Ser |
| 305 | | | | | 310 | | | | | 315 | | | | 320 |
| Thr | Tyr | Arg | Val | Val | Ser | Val | Leu | Thr | Val | Leu | His | Gln | Asp | Trp |
| | | | | 325 | | | | | 330 | | | | | 335 |
| Leu | Asn | Gly | Lys | Glu | Tyr | Lys | Cys | Lys | Val | Ser | Asn | Lys | Ala | Leu |
| | | | | 340 | | | | | 345 | | | | | 350 |
| Pro | Ala | Pro | Ile | Glu | Lys | Thr | Ile | Ser | Lys | Ala | Lys | Gly | Gln | Pro |
| | | | | 355 | | | | | 360 | | | | | 365 |
| Arg | Glu | Pro | Gln | Val | Tyr | Thr | Leu | Pro | Pro | Ser | Arg | Glu | Glu | Met |
| | | | | | | | | | | | | | | |
| Cys | Leu | Val | Lys | Gly | Phe | Tyr | Pro | Ser | Asp | Ile | Ala | Val | Glu | Trp | Glu |

```
                    370                 375                 380
Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 33
<211> LENGTH: 448
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Trp Leu His Trp Val Arg Gln Ala Pro Gly Lys Gly Leu Glu Trp Val
            35                  40                  45

Gly Met Ile Asp Pro Ser Asn Ser Asp Thr Arg Phe Asn Pro Asn Phe
        50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Asp Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 34
<211> LENGTH: 448
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Trp Leu His Trp Val Arg Gln Ala Pro Gly Lys Gly Leu Glu Trp Val
                35                  40                  45

Gly Met Ile Asp Pro Ser Asn Ser Asp Thr Arg Phe Asn Pro Asn Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ala Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
```

```
                    210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 35
<211> LENGTH: 448
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
               130                 135                 140
Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Gly Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 36
<211> LENGTH: 220
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
                20                  25                  30

Ser Ser Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
```

```
                    50                  55                  60
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                     85                  90                  95

Tyr Tyr Ala Tyr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
                210                 215                 220

<210> SEQ ID NO 37
<211> LENGTH: 220
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Tyr Thr
                20                  25                  30

Ser Ser Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                     85                  90                  95

Tyr Tyr Ala Tyr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Lys Gln Leu Lys Ser Gly Thr Ala Arg Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
```

```
                195                 200                 205
Ser Pro Val Thr Lys Ser Phe Asn Arg Gly Glu Cys
    210                 215                 220

<210> SEQ ID NO 38
<211> LENGTH: 220
<212> TYPE: PRT
<213> ORGANISM: Artificial Sequence
<220> FEATURE:
<223> OTHER INFORMATION: Synthetic Construct

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Arg Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ile Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 39
<211> LENGTH: 448
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60
```

```
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 40
<211> LENGTH: 448
<212> TYPE: PRT
<213> ORGANISM: Artificial Sequence
<220> FEATURE:
<223> OTHER INFORMATION: Synthetic Construct
```

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Asp Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
```

```
                    405                 410                 415
Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 41
<211> LENGTH: 448
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ala Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                    325                 330                 335
Thr Ile Ser Lys Ala Lys Gly Gln Pro Arg Glu Pro Gln Val Tyr Thr
                340                 345                 350

Leu Pro Pro Ser Arg Glu Glu Met Thr Asp Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 42
<211> LENGTH: 448
<212> TYPE: PRT
<213> ORGANISM: Artificial Sequence
<220> FEATURE:
<223> OTHER INFORMATION: Synthetic Construct

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Ala Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Gly Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                245                 250                 255
Arg Thr Pro Glu Val Thr Cys Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Gln Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Asp Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Met Ser Asp Gly Ser Phe Phe Leu Ala Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

<210> SEQ ID NO 43
<211> LENGTH: 214
<212> TYPE: PRT
<213> ORGANISM: Artificial Sequence
<220> FEATURE:
<223> OTHER INFORMATION: Synthetic Construct

<400> SEQUENCE: 43

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 44
<211> LENGTH: 214
<212> TYPE: PRT
<213> ORGANISM: Artificial Sequence
<220> FEATURE:
<223> OTHER INFORMATION: Synthetic Construct

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Lys Gln Leu Lys Ser Gly
        115                 120                 125

Thr Ala Arg Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 45
<211> LENGTH: 214
<212> TYPE: PRT
<213> ORGANISM: Artificial Sequence
<220> FEATURE:
<223> OTHER INFORMATION: Synthetic Construct

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ile
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 450
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ala
1                5                  10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
 50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Arg Pro Arg Val
            340                 345                 350

Tyr Thr Leu Pro Pro Ser Arg Glu Glu Met Thr Lys Asn Gln Val Ser
        355                 360                 365

Leu Val Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Val Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 47
<211> LENGTH: 450
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80
```

```
Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Arg Pro Arg Val
            340                 345                 350

Tyr Thr Leu Pro Pro Ser Arg Glu Glu Met Thr Lys Asn Gln Val Ser
        355                 360                 365

Leu Val Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Val Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 48
<211> LENGTH: 213
<212> TYPE: PRT
<213> ORGANISM: Artificial Sequence
<220> FEATURE:
<223> OTHER INFORMATION: Synthetic Construct
```

-continued

```
<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 49
<211> LENGTH: 213
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Lys Gln Leu Lys Ser Gly Thr
        115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 50
<211> LENGTH: 445
<212> TYPE: PRT
<213> ORGANISM: Artificial Sequence
<220> FEATURE:
<223> OTHER INFORMATION: Synthetic Construct

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

-continued

```
Lys Phe Asn Trp Tyr Val Asp Gly Val Glu Val His Asn Ala Lys Thr
                275                 280                 285
Lys Pro Arg Glu Glu Gln Tyr Gln Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Arg Val Tyr Thr Leu Pro Pro
            340                 345                 350
Ser Arg Glu Glu Met Thr Lys Asn Gln Val Ser Leu Val Cys Leu Val
            355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Val Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445

<210> SEQ ID NO 51
<211> LENGTH: 445
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Thr Tyr
                20                  25                  30
Tyr Leu His Trp Val Arg Gln Ala Pro Gly Gln Gly Leu Glu Trp Met
            35                  40                  45
Gly Trp Ile Tyr Pro Gly Asn Val His Ala Gln Tyr Asn Glu Lys Phe
        50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Trp Glu Gly Phe Pro Tyr Trp Gly Gln Gly Thr Thr Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Val Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 52
<211> LENGTH: 214
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Lys Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 53
<211> LENGTH: 214
<212> TYPE: PRT
<213> ORGANISM: Artificial Sequence
<220> FEATURE:
<223> OTHER INFORMATION: Synthetic Construct

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Lys Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Lys Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 54
<211> LENGTH: 337
<212> TYPE: PRT
<213> ORGANISM: Artificial Sequence
<220> FEATURE:

<223> OTHER INFORMATION: Synthetic Construct

<400> SEQUENCE: 54

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
            115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly
```

<210> SEQ ID NO 55
<211> LENGTH: 107
<212> TYPE: PRT
<213> ORGANISM: Artificial Sequence
<220> FEATURE:
<223> OTHER INFORMATION: Synthetic Construct

<400> SEQUENCE: 55

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 56
<211> LENGTH: 337
<212> TYPE: PRT
<213> ORGANISM: Artificial Sequence
<220> FEATURE:
<223> OTHER INFORMATION: Synthetic Construct

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
            115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
            195                 200                 205

Glu Tyr Lys Cys Lys Val Ser Asn Lys Ala Leu Pro Ala Pro Ile Glu
210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255
```

Thr Cys Leu Val Lys Gly Phe Tyr Pro Ser Asp Ile Ala Val Glu Trp
                260                 265                 270

Glu Ser Asn Gly Gln Pro Glu Asn Asn Tyr Lys Thr Thr Pro Pro Val
            275                 280                 285

Leu Asp Ser Asp Gly Ser Phe Phe Leu Tyr Ser Lys Leu Thr Val Asp
        290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Arg Thr Val Ala Ala Pro Ser Val Phe Ile Phe Pro Pro Ser Asp Lys
1               5                   10                  15

Gln Leu Lys Ser Gly Thr Ala Arg Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 337
<212> TYPE: PRT
<213> ORGANISM: Artificial Sequence
<220> FEATURE:
<223> OTHER INFORMATION: Synthetic Construct

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ala Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Gly Ser Ile Glu Gly Arg Gly
            100                 105                 110

```
Ser Thr His Thr Cys Pro Pro Cys Pro Ala Pro Glu Leu Leu Gly Gly
            115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Arg Thr Val Ala Ala Pro Ser Val Phe Ile Phe Pro Pro Ser Asp Glu
1               5                   10                  15

Gln Leu Lys Ser Gly Thr Ala Arg Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ile Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 60
<211> LENGTH: 337
<212> TYPE: PRT
```

<213> ORGANISM: Artificial Sequence
<220> FEATURE:
<223> OTHER INFORMATION: Synthetic Construct

<400> SEQUENCE: 60

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly
```

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

```
<400> SEQUENCE: 61

Arg Thr Val Ala Ala Pro Ser Val Phe Ile Phe Pro Pro Ser Asp Lys
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 62
<211> LENGTH: 337
<212> TYPE: PRT
<213> ORGANISM: Artificial Sequence
<220> FEATURE:
<223> OTHER INFORMATION: Synthetic Construct

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gly Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
            115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
```

```
                    245                 250                 255

Thr Cys Leu Val Lys Gly Phe Tyr Pro Ser Asp Ile Ala Val Glu Trp
                260                 265                 270

Glu Ser Asn Gly Gln Pro Glu Asn Asn Tyr Lys Thr Thr Pro Pro Val
            275                 280                 285

Leu Asp Ser Asp Gly Ser Phe Phe Leu Tyr Ser Lys Leu Thr Val Asp
        290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly

<210> SEQ ID NO 63
<211> LENGTH: 337
<212> TYPE: PRT
<213> ORGANISM: Artificial Sequence
<220> FEATURE:
<223> OTHER INFORMATION: Synthetic Construct

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ala Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270
```

Glu Ser Asn Gly Gln Pro Glu Asn Asn Tyr Lys Thr Thr Pro Pro Val
            275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly

<210> SEQ ID NO 64
<211> LENGTH: 107
<212> TYPE: PRT
<213> ORGANISM: Artificial Sequence
<220> FEATURE:
<223> OTHER INFORMATION: Synthetic Construct

<400> SEQUENCE: 64

Arg Thr Val Ala Ala Pro Ser Val Phe Ile Phe Pro Pro Ser Asp Lys
1               5                   10                  15

Gln Leu Lys Ser Gly Thr Ala Arg Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ile Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 337
<212> TYPE: PRT
<213> ORGANISM: Artificial Sequence
<220> FEATURE:
<223> OTHER INFORMATION: Synthetic Construct

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gly Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys Asp Lys Gly Ser Ile Glu Gly Arg Gly
            100                 105                 110

Ser Thr His Thr Cys Pro Pro Cys Pro Ala Pro Glu Leu Leu Gly Gly
        115                 120                 125

```
Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly

<210> SEQ ID NO 66
<211> LENGTH: 98
<212> TYPE: PRT
<213> ORGANISM: Artificial Sequence
<220> FEATURE:
<223> OTHER INFORMATION: Synthetic Construct

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 67
<211> LENGTH: 98
<212> TYPE: PRT
<213> ORGANISM: Artificial Sequence
<220> FEATURE:
<223> OTHER INFORMATION: Synthetic Construct
```

<400> SEQUENCE: 67

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Ala Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Glu
                85                  90                  95
Lys Val

<210> SEQ ID NO 68
<211> LENGTH: 98
<212> TYPE: PRT
<213> ORGANISM: Artificial Sequence
<220> FEATURE:
<223> OTHER INFORMATION: Synthetic Construct

<400> SEQUENCE: 68

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Ala Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ala Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val

<210> SEQ ID NO 69
<211> LENGTH: 98
<212> TYPE: PRT
<213> ORGANISM: Artificial Sequence
<220> FEATURE:
<223> OTHER INFORMATION: Synthetic Construct

<400> SEQUENCE: 69

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Glu

Lys Val

<210> SEQ ID NO 70
<211> LENGTH: 98
<212> TYPE: PRT
<213> ORGANISM: Artificial Sequence
<220> FEATURE:
<223> OTHER INFORMATION: Synthetic Construct

<400> SEQUENCE: 70

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gly Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 71
<211> LENGTH: 98
<212> TYPE: PRT
<213> ORGANISM: Artificial Sequence
<220> FEATURE:
<223> OTHER INFORMATION: Synthetic Construct

<400> SEQUENCE: 71

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ala Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val
```

<210> SEQ ID NO 72
<211> LENGTH: 98
<212> TYPE: PRT
<213> ORGANISM: Artificial Sequence
<220> FEATURE:
<223> OTHER INFORMATION: Synthetic Construct

<400> SEQUENCE: 72

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ala Asp Tyr
            20                  25                  30
```

-continued

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Gly Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val

<210> SEQ ID NO 73
<211> LENGTH: 217
<212> TYPE: PRT
<213> ORGANISM: Artificial Sequence
<220> FEATURE:
<223> OTHER INFORMATION: Synthetic Construct

<400> SEQUENCE: 73

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 74
<211> LENGTH: 217
<212> TYPE: PRT
<213> ORGANISM: Artificial Sequence
<220> FEATURE:
<223> OTHER INFORMATION: Synthetic Construct

<400> SEQUENCE: 74

Ala Pro Glu Leu Leu Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                      55                  60

Gln Tyr Asn Ser Thr Tyr Arg Val Val Ser Val Leu Thr Val Leu His
65                   70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Glu Glu Met
         115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Met Ser Asp Gly Ser Phe Phe Leu
                 165                 170                 175

Ala Ser Lys Leu Thr Val Asp Lys Ser Arg Trp Gln Gln Gly Asn Val
             180                 185                 190

Phe Ser Cys Ser Val Met His Glu Ala Leu His Asn His Tyr Thr Gln
         195                 200                 205

Lys Ser Leu Ser Leu Ser Pro Gly Lys
    210                 215

<210> SEQ ID NO 75
<211> LENGTH: 217
<212> TYPE: PRT
<213> ORGANISM: Artificial Sequence
<220> FEATURE:
<223> OTHER INFORMATION: Synthetic Construct

<400> SEQUENCE: 75

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                      55                  60

Gln Tyr Asn Ser Thr Tyr Arg Val Val Ser Val Leu Thr Val Leu His
65                   70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Glu Glu Met
         115                 120                 125

Thr Asp Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160
```

```
Tyr Lys Thr Thr Pro Val Leu Met Ser Asp Gly Ser Phe Phe Leu
            165                 170                 175

Ala Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 76
<211> LENGTH: 217
<212> TYPE: PRT
<213> ORGANISM: Artificial Sequence
<220> FEATURE:
<223> OTHER INFORMATION: Synthetic Construct

<400> SEQUENCE: 76

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Ser Thr Leu Pro Pro Ser Arg Glu Glu Met
        115                 120                 125

Thr Lys Asn Gln Val Ser Leu Val Cys Leu Val Tyr Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Val Leu Thr Val Asp Lys Ser Arg Trp Gln Gln Gly Asn Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 77
<211> LENGTH: 217
<212> TYPE: PRT
<213> ORGANISM: Artificial Sequence
<220> FEATURE:
<223> OTHER INFORMATION: Synthetic Construct

<400> SEQUENCE: 77

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
            20                  25                  30
Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
             100                 105                 110

Pro Arg Glu Pro Gln Val Ser Thr Leu Pro Pro Ser Arg Glu Glu Met
         115                 120                 125

Thr Lys Asn Gln Val Ser Leu Met Cys Leu Val Tyr Gly Phe Tyr Pro
     130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 78
<211> LENGTH: 217
<212> TYPE: PRT
<213> ORGANISM: Artificial Sequence
<220> FEATURE:
<223> OTHER INFORMATION: Synthetic Construct

<400> SEQUENCE: 78

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Glu Glu Met
         115                 120                 125

Thr Lys Asn Gln Val Ser Leu Val Cys Leu Val Lys Gly Phe Tyr Pro
     130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

165                 170                 175
Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 79
<211> LENGTH: 217
<212> TYPE: PRT
<213> ORGANISM: Artificial Sequence
<220> FEATURE:
<223> OTHER INFORMATION: Synthetic Construct

<400> SEQUENCE: 79

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Arg Pro Arg Val Tyr Thr Leu Pro Pro Ser Arg Glu Glu Met
        115                 120                 125

Thr Lys Asn Gln Val Ser Leu Val Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 80
<211> LENGTH: 217
<212> TYPE: PRT
<213> ORGANISM: Artificial Sequence
<220> FEATURE:
<223> OTHER INFORMATION: Synthetic Construct

<400> SEQUENCE: 80

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Asp Met
            115                 120                 125

Thr Lys Asn Gln Val Gln Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 81
<211> LENGTH: 217
<212> TYPE: PRT
<213> ORGANISM: Artificial Sequence
<220> FEATURE:
<223> OTHER INFORMATION: Synthetic Construct

<400> SEQUENCE: 81

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Gly Asp Met
            115                 120                 125

Thr Lys Asn Gln Val Gln Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 82
<211> LENGTH: 217
<212> TYPE: PRT
<213> ORGANISM: Artificial Sequence
<220> FEATURE:
<223> OTHER INFORMATION: Synthetic Construct

<400> SEQUENCE: 82

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Asp Met
        115                 120                 125

Thr Lys Asn Gln Val Arg Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 83
<211> LENGTH: 217
<212> TYPE: PRT
<213> ORGANISM: Artificial Sequence
<220> FEATURE:
<223> OTHER INFORMATION: Synthetic Construct

<400> SEQUENCE: 83

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

```
Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 84
<211> LENGTH: 217
<212> TYPE: PRT
<213> ORGANISM: Artificial Sequence
<220> FEATURE:
<223> OTHER INFORMATION: Synthetic Construct

<400> SEQUENCE: 84

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Met Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205
Lys Ser Leu Ser Leu Ser Pro Gly Lys
    210                 215
```